US008084436B2

(12) United States Patent
Freier et al.

(10) Patent No.: US 8,084,436 B2
(45) Date of Patent: Dec. 27, 2011

(54) MODULATION OF SGLT2 EXPRESSION

(75) Inventors: Susan M. Freier, San Diego, CA (US); Edward Wancewicz, Poway, CA (US); Brett P. Monia, Encinitas, CA (US); Andrew M. Siwkowski, Carlsbad, CA (US); Lynnetta Watts, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 607 days.

(21) Appl. No.: 12/145,470

(22) Filed: Jun. 24, 2008

(65) Prior Publication Data
US 2010/0324122 A1    Dec. 23, 2010

Related U.S. Application Data

(63) Continuation of application No. 10/980,002, filed on Nov. 2, 2004, which is a continuation-in-part of application No. 10/946,498, filed on Sep. 21, 2004.

(60) Provisional application No. 60/517,334, filed on Nov. 3, 2003.

(51) Int. Cl.
A01N 43/04    (2006.01)
A61K 31/70    (2006.01)
C07H 21/04    (2006.01)

(52) U.S. Cl. .................................. 514/44 A; 536/24.5
(58) Field of Classification Search ............... 514/44 A; 536/24.5
See application file for complete search history.

(56) References Cited

U.S. PATENT DOCUMENTS

| | | | |
|---|---|---|---|
| 5,240,847 A | 8/1993 | Heckl et al. | |
| 5,366,878 A | 11/1994 | Pederson et al. | |
| 5,998,148 A | 12/1999 | Bennett et al. | |
| 6,133,246 A | 10/2000 | McKay et al. | |
| 6,150,101 A | 11/2000 | Grotendorst et al. | |
| 6,162,616 A * | 12/2000 | Shyjan | 435/69.1 |
| 6,211,440 B1 * | 4/2001 | Briggs et al. | 800/301 |
| 6,284,538 B1 | 9/2001 | Monia et al. | |
| 6,414,126 B1 | 7/2002 | Ellsworth et al. | |
| 6,506,559 B1 | 1/2003 | Fire et al. | |
| 6,537,751 B1 | 3/2003 | Cohen et al. | |
| 6,582,908 B2 | 6/2003 | Fodor et al. | |
| 6,809,193 B2 | 10/2004 | McKay et al. | |
| 6,875,747 B1 | 4/2005 | Iversen et al. | |
| 6,965,025 B2 | 11/2005 | Gaarde et al. | |
| 7,273,932 B1 | 9/2007 | LaBarbera et al. | |
| 7,507,810 B2 | 3/2009 | Karras et al. | |
| 2002/0052326 A1 | 5/2002 | Washburn | |
| 2002/0137708 A1 | 9/2002 | Bennett et al. | |
| 2003/0040497 A1 | 2/2003 | Teng et al. | |
| 2003/0055019 A1 | 3/2003 | Shimkets et al. | |
| 2003/0083280 A1 | 5/2003 | Crooke et al. | |
| 2003/0087411 A1 | 5/2003 | Bird et al. | |
| 2003/0223975 A1 | 12/2003 | Tonks et al. | |
| 2003/0232336 A1 | 12/2003 | Curtis et al. | |
| 2004/0162249 A1 | 8/2004 | Liang et al. | |
| 2005/0032693 A1 | 2/2005 | Gerritsen et al. | |
| 2005/0053981 A1 | 3/2005 | Swayze et al. | |
| 2005/0059629 A1 | 3/2005 | Gaarde et al. | |
| 2005/0107325 A1 | 5/2005 | Manoharan et al. | |
| 2005/0191653 A1 | 9/2005 | Freier et al. | |
| 2006/0063722 A1 | 3/2006 | Washburn et al. | |
| 2007/0238866 A1 | 10/2007 | Deshpande et al. | |
| 2007/0299028 A1 | 12/2007 | Siwokowski et al. | |

FOREIGN PATENT DOCUMENTS

| | | |
|---|---|---|
| EP | 1293569 | 3/2003 |
| EP | 1308459 | 5/2003 |
| WO | WO 97/29780 | 8/1997 |
| WO | WO 99/60012 | 11/1999 |
| WO | WO 99/66959 | 12/1999 |
| WO | WO 00/13706 | 3/2000 |
| WO | WO 00/18918 | 4/2000 |
| WO | WO 00/27868 | 5/2000 |
| WO | WO 00/35936 | 6/2000 |
| WO | WO 01/29217 | 4/2001 |
| WO | WO 02/096927 | 12/2002 |
| WO | WO 2004/016754 | 2/2004 |
| WO | WO 2005/038013 | 4/2005 |
| WO | WO 2005/042552 | 5/2005 |

OTHER PUBLICATIONS

Agrawal et al., "Pharmacokinetics, Biodistrubution, and Stability of Oligodexynucleotide Phosphorothioates in Mice" PNAS (1991) 88:7595-7599.
Arakawa et al., "Improved Diabetic Syndrome in C57BL/KsJ-db/db Mice by Oral Administration of the Na-Glucose Cotransporter Inhibitor T-1095" Br. J. Pharmacol. (2001) 132:578-586.
Brown et al., "Glucose Transporters: Structure, Function, and Consequences of Deficiency" J. Inherit. Metab. Dis. (2000) 23:237-246.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Dang et al., "Oncogenic Alterations of Metabolism" TIBS (1999) 24:68-72. European Supplementary Search Report for Application No. EP 04800679.5 dated Mar. 6, 2008.
Garay et al., "Inhibition of hypoxia/reoxygenation-induced apoptosis by an antisense oligonucleotide targeted to JNK1 in human kidney cells" Biochemical Pharmacology (2000) 59:1033-1043.
Geary et al., "Pharmacokinetics of Phosphorothioate Antisense Oligodeoxynucleotides" curr. Opin. Investig. Drugs (2001) 2:562-573.
Geary et al., "Pharmacokinetic Properties of 2'-O-(2-Methoxyethyl)-Modified Oligonucleotide Analogs in Rats" J. Pharm. Exp. Therap. (2001) 296:890-897.
Hediger te al., "Molecular Genetics of the Human Na/Glucose Cotransporter" Klin. Wochenschr. (1989) 67:843-846. from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

*Primary Examiner* — Brian Whiteman
(74) *Attorney, Agent, or Firm* — Isis Pharmaceuticals, Inc. Patent Dept.

(57) ABSTRACT

Compounds, compositions and methods are provided for modulating the expression of SGLT2. The compositions comprise oligonucleotides, targeted to nucleic acid encoding SGLT2. Methods of using these compounds for modulation of SGLT2 expression and for diagnosis and treatment of diseases and conditions associated with expression of SGLT2 are provided.

54 Claims, No Drawings

OTHER PUBLICATIONS

International Search Report for Application No. PCT/US04/36620 dated Nov. 23, 2005.
Ishikawa et al., "SGLT Gene Expression in Primary Lung Cancers and their Metastatic Lesions" Jpn. J. Cancer Res. (2001) 92:874-879.
Kanai et al., "The Human Kidney Low Affinity Na/Glucose Cotransporter SGLT2" J. Clin. Invest. (1994) 93:397-404.
Kong et al., "Cloning and Expression of a Mammalian Na/Amino Acid Cotransporter with Sequence Similarity to Na/Glucose Cotransporters" J. Biol. Chem. (1993) 268:1509-1512.
Ma et al., "Synthetic oligonucleotides as therapeutics: the coming of age" Biotechnology Annual Review (2000) 5:155-196.
MacKenzie et al., "Biophysical Characteristics of the Pig Kidney Na/Glucose Cotransporter SGLT2 Reveal a Common Mechanism for SGLT1 and SGLT2" J. Biol. Chem. (1996) 271:32678-32683.
MacKenzie et al., "SAAT1 is a Low Affinity Na/Glucose Cotransporter and not an Amino Acid Transporter" J. Biol. Chem. (1994) 269:22488-22491.
Maier et al., "Enzymatic Degradation of Varius Antisense Oligonucleotides: Monitoring and Fragment Identification by MECC and ES-MS" Biomed. Pept. Proteins Nucleic Acids (1995) Vik, 1, 235-242.
Nawano et al., "Hyperglycemia Contributes Insulin Resistance in Hepatic and Adipose Tissue but not Skeletal Muscle of ZDF Rats" Am. J. Physiol. Endocrinol. Metab. (2000) 278:E535-E543.
New England Biolabs, 1998/1999 Catalog, pp. 121 and 284.
Oku et al., "T-1095, An Inhibitor of Renal Na/Glucose Cotransporters, May Provide a Novel Approach to Trating Diabetes" Diabetes (1999) 48:1794-1800.
Oku et al., "Antidiabetic Effect of T-1095, An Inhibitor of Na-Glucose Cotransporter, In Neonatally Streptozotocin-Trated Rats" Eur. J. Pharmacol. (2000) 391:183-192.
Pontoglio et al., "HNF-1a Controls Renal Glucose Reabsorption in Mouse and Man" EMBO Reports (2000) 1:359-365.
Reynolds et al., "Rational siRNA design for RNA interference" Nature Biotechnology (2004) 22(3):326-330.
Shaw et al., "Modified Deoxyoligonucleotides Stable to Exonuclease Degradation in Serum" Nucleic Acids Res. (1991) 19:747-750.
Tabatabai et al., "Differential Regulation of Mouse Kidney Sodium-Dependent Transporters mRNA by Cadmium" Toxicol. Appl. Pharmacol. (2001) 177:163-173.
Tsujihara et al., "Na/Glucose Cotransporter (SGLT) Inhibitors as Antidiabetic Agents. 4. Synthesis and Pharmacological Properties of 4'-Dehydroxyphlorizin Derivatives Substitutes on the B Ring" J. Med. Chem. (1999) 42:5311-5324.
Turner et al., "Heterogeneity of Sodiu,-Dependent D-Glucose Transport Sites Along the Proximal Tubule: Evidence from Vesicle Studies" Am. J. Physiol. (1982) 242:F406-F414.
Turner et al., "Stoichiometric Studies of the Rental Outer Cortical Brush Border Membrane p-Glucose Transporter" J. Membrane Biol. (1982) 67:73-80.
Van Den Heuvel et al., "Autosomal Recessive Renal Glucosuria Attributable to a Mutation in the Sodium Glucose Cotransporter (SGLT2)" Hum. Genet. (2002) 111:544-547.
Vestri et al., "Changes in Sodium or Glucose Filtration Rate Modulate Expression of Glucose Transporters in Renal Proximal Tubular Cells of Rat" J. Membrane Biol. (2001) 182:105-112.
Wells et al., "Cloning of a Human Kidney cDNA with Similarity to the Sodium-Glucose Cotransporter" Am. J. Physiol. (1992) 263:F459-F465.
Wells et al., "Localization of the Na/Glucose Cotransporter Gene SGLT-2 to Human Chromosome 16 Close to the Centromere" Genomics (1993) 17:787-789.
Woolf et al., "The Stability, Toxicity and Effectiveness of Unmodified and Phosphorothioate Antisense Oligodeoxynucleotides in Xenopus Oocytes and Embryos" Nucleic Acids Res. (1990) 18:1763-1769.
Wright, "Renal NA-Glucose Cotransporters" Am. J. Physiol. Renal Physiol (2001) 280:F10-F18.
You et al., "Molecular Characteristics of Na-Coupled Glucose Transporters in Adult and Embryonic Rat Kidney" J. Biol. Chem. (1995) 270:29365-29371.

Adler et al., "Glomerular mRNAs in human type 1 diabetes: Biochemical evidence for microalbuminuria as a manifestation of diabetic nephropathy" Kidney International (2001) 60:2330-2336.
Agrawal et al., "Antisense therapeutics: is it as simple as complementary base recognition?" Molecular Medicine Today (2000) 61:72-81.
Balboa et al., "Protein Kinase C alpha Mediates Phospholipase D Activation by Nucleotides and Phorbol Ester in Madin-Darby Canine Kidney Cells" Journal of Biological Chemistry (1994) 269(14):10511-10516.
Branch et al., "A good antisense molecule is hard to find" TIBS (1998) 23:45-50.
Crooke et al., "Basic Principles of Antisense Therapeutics" Antisense Research and Application (1998) Chapter 1:1-50.
El-Din et al., "Connective Tissue Growth Factor: What's in a Name?" Molecular Genetics and Metabolism (2000) 71:276-292.
European Supplementary Search Report for Application No. EP 04788853.2 dated Mar. 6, 2008.
Final Rejection for U.S. Appl. No. 1-/980,002 dated Oct. 25, 2007.
Final Rejection for U.S. Appl. No. 10/946,498 dated Aug. 20, 2007.
Final Rejection for U.S. Appl. No. 10/946,498 dated Nov. 18, 2008.
Gewirtz et al., "Facilitating Oligonucleotide Delivery: Helping Antisense Deliver on its Promise" PNAS (1996) 93:3161-3163.
Godson et al., "Inhibition of Expression of Protein Kinase C alpha by Antisense cDNA Inhibits Phorbol Ester-mediated Arachindonate Release" Journal of Biological Chemistry (1993) 286(16):11946-11950.
Hishikawa et al., "Connective Tissue Growth Factor Induces Apoptosis in Human Breast Cancer Cell Line MCF-7" J. Biol. Chem. (1999) 274(52):37461-37466.
Hishikawa et al., "Transforming growth factor-B1 induces apoptosis via connective tissue growth factor in human aortic smooth muscle cells" European Journal of Pharmacology (1999) 385:287-290.
Hishikawa et al., "Static Pressure Regulates Connective Tissue Growth Factor Expression in Human Mesangial Cells" J. Biol. Chem. (2001) 276(20):16797-16803.
International Search Report for Application No. PCT/US04/30785 dated Jan. 31, 2005.
International Search Report for Application No. PCT/US07/68406 dated Mar. 13, 2008.
Lau et al., "The CNN Family of Angiogenic Regulators: The Integrin Connection" Experimental Cell Research (1999) 248:44-57.
Monia et al., "Evaluation of 2'-Modified Oligonucleotides Containing 2'-Deoxy Gaps as Antisense Inhibitors of Gene Expression" The Journal of Biological Chemistry (1993) 268:14514-14522.
Office Action for U.S. Appl. No. 10/980,002 dated May 15, 2007.
Office Action for U.S. Appl. No. 10/980,002 dated Oct. 15, 2008.
Office Action for U.S. Appl. No. 10/946,498 dated Dec. 8, 2006.
Office Action for U.S. Appl. No. 10/946,498 dated Mar. 3, 2008.
Riser et al., "Urinary CCN2 (CTGF) as a possible predictor of diabetic nephropathy: Preliminary report" Kidney International (2003) 64:451-458.
Sanghvi et al., "Heterocyclic Base Modifications in Nucleic Acids and Their Applications in Antisense Oligonucleotides" Antisense Research and Applications (1993) pp. 273-288.
Shimo et al., "Inhibition of Endogenous Expression of Connective Tissue Growth Factor by Its Antisense Oligonucleotide and Antisense RNA Suppresses Proliferation and Migration of Vascular Endothelial Cells" J. Biochem. (1998) 124:130-140.
Tuschl et al., The siRNA user guide, 2001.
Twigg et al., "Advanced Glycosylation End Products Up-Regulate Connective Tissue Growth Factor (Insulin-Like Growth Factor-Binding Protein Related Protein 2) in Human Fibroblasts: A Potential Mechanism for Expansion of Extracellular Matrix in Diabetes Mellitus" Endocrinology (2001) 142(5):1760-1769.
Zhou et al., Human Cardiomyocytes Express High Level of NA+/Glucose Cotransporter 1 (SGLT), Journal of Cellular Biochemistry (2003) 90:339-346.
Chirila et al., "The use of synthetic polymers for delivery of therapeutic antisense oligodeoxynucleotides" Biomaterials (2002) 23:321-342.
Crooke et al. "Progress in Antisense Technology" Ann. Rev. Medicine (2004) 55:61-95.
Office Action for U.S. Appl. No. 12/299,611 dated May 3, 2010.
Opalinska et al., "Nucleic-acid therapetuics: basic principles and recent applications" Nature Rev. (2002) 1:503-514.
Peracchi et al., "Prospects for antiviral ribozymes and deoxyribozymes" Rev. Med. Virol. (2004) 14:47-64.

* cited by examiner

MODULATION OF SGLT2 EXPRESSION

CROSS-REFERENCE TO RELATED APPLICATIONS

This application is a continuation of U.S. application Ser. No. 10/980,002, filed Nov. 2, 2004, which is a continuation-in-part of U.S. application Ser. No. 10/946,498, filed Sep. 21, 2004, and which claims the benefit of priority to U.S. provisional patent application Ser. No. 60/517,334, filed Nov. 3, 2003, each of which is incorporated herein by reference in its entirety.

FIELD OF THE INVENTION

The present invention provides compositions and methods for modulating the expression of SGLT2. In particular, this invention relates to antisense compounds, particularly oligonucleotide compounds, which, in some embodiments, hybridize with nucleic acid molecules encoding SGLT2. Such compounds are shown herein to modulate the expression of SGLT2.

BACKGROUND OF THE INVENTION

A fundamental component of energy metabolism is glucose transport. The transport of glucose across cell membranes is essential to metabolic processes, including the maintenance of a relatively constant blood glucose concentration and the delivery of glucose to peripheral tissues for storage and utilization. As cell membranes are essentially impermeable to glucose, the movement of glucose across membranes must be accomplished by protein transporters (Brown, *J. Inherit. Metab. Dis.*, 2000, 23, 237-246).

Mediated glucose transport occurs in two forms, secondary active transport and facilitated transport. In cells where glucose is rapidly metabolized, the concentration gradient across the plasma membrane is used to drive facilitated transport, and an active mechanism is not required. Secondary active transport of glucose enables cells to transport glucose against a concentration gradient. This mechanism involves cotransport of glucose and sodium ions across the apical surface of the cells and the energy is provided by the sodium gradient maintained by the sodium/potassium ATPase in the basolateral membrane. Efflux of glucose from the cells into the circulation is then mediated by a facilitative transporter (Brown, *J. Inherit. Metab. Dis.*, 2000, 23, 237-246; Wright, *Am. J. Physiol. Renal Physiol.*, 2001, 280, F10-18).

Secondary active transport of glucose operates in the mucosal cells of the intestine and the proximal tubular cells of the kidney and functions to ensure efficient uptake of dietary glucose and minimal urinary loss. Plasma glucose is normally filtered in the kidney in the glomerulus and actively reabsorbed in the proximal tubule. Glucose is essentially completely reabsorbed from the urine in the proximal tubule of the kidney through the action of the sodium-glucose cotransporters (SGLTs) located in the brush border membrane (BBM). Comparison of the glucose transport properties of proximal tubule BBM vesicles prepared from the outer cortex and the outer medulla of rabbit kidney revealed the presence of two distinct sodium-coupled D-glucose transport systems. The outer cortex preparation exhibited a low-affinity/high-capacity activity ($K_m$=6 mM), whereas the outer medulla displayed a high-affinity/low-capacity activity ($K_m$=0.35 mM) (Turner and Moran, *Am. J. Physiol. Endocrinol. Metab.*, 1982, 242, F406-414; Wright, *Am. J. Physiol. Renal Physiol.*, 2001, 280, F10-18). Further characterization of the renal outer cortical BBM transport system revealed a glucose to sodium coupling ratio of 1:1, whereas the ratio is 2:1 in vesicles isolated from the outer medullary tissue (Turner and Moran, *J. Membr. Biol.*, 1982, 67, 73-80).

Isolation of nucleic acid molecules encoding SGLTs confirmed the presence of multiple transport systems. A cDNA encoding human SGLT2 (also known as solute carrier family 2, member 5, Na-dependent glucose cotransporter 2 or SLC2A5) was identified in a screen for sodium cotransporter-like sequences in a cDNA library prepared from human kidney (Kanai et al., *J. Clin. Invest.*, 1994, 93, 397-404; Wells et al., *Am. J. Physiol. Endocrinol. Metab.*, 1992, 263, F459-465). Human SGLT2 localizes to chromosome 16p11.2 (Wells et al., *Genomics*, 1993, 17, 787-789). Subsequent investigations of human SGLT2 revealed that has functional properties characteristic of a low-affinity, sodium-dependent glucose cotransporter.

Studies of human SGLT2 injected into *Xenopus* oocytes demonstrated that this protein mediates sodium-dependent transport of D-glucose and α-methyl-D-glucopyranoside (α-MeGlc; a glucose analog) with a $K_m$ value of 1.6 mM for α-MeGlc and a sodium to glucose coupling ratio of 1:1 (Kanai et al., *J. Clin. Invest.*, 1994, 93, 397-404; You et al., *J. Biol. Chem.*, 1995, 270, 29365-29371). This transport activity was suppressed by phlorizin, a plant glycoside that binds to the glucose site but is not transported and thus inhibits SGLTs (You et al., *J. Biol. Chem.*, 1995, 270, 29365-29371). These findings indicated that SGLT2 is responsible for the low-affinity transport observed in BBM vesicle preparations from rabbit kidney outer cortex.

The tissue distribution of SGLT2 further suggested that this cotransporter is the kidney low-affinity glucose transporter. Northern blotting revealed that human SGLT2 is primarily expressed in kidney, and in situ hybridization of a human SGLT2 probe to rat kidney tissue demonstrated that SGLT2 is expressed in the proximal tubule S1 segments in the outer cortex (Kanai et al., *J. Clin. Invest.*, 1994, 93, 397-404; Wells et al., *Am. J. Physiol. Endocrinol. Metab.*, 1992, 263, F459-465). This localization pattern distinguishes SGLT2 from SGLT1, the high-affinity/low-capacity sodium/glucose transporter that is expressed in the proximal tubule S3 segments of the outer medulla, where it is appropriately positioned to reabsorb the remainder of filtered glucose not reabsorbed by SGLT2 in the proximal tubule S1 segments.

Rat SGLT2, like human SGLT2, is strongly expressed in proximal S1 segments and this expression is developmentally regulated, with expression appearing on embryonic day 17, gradually increasing until day 19 and subsequently decreasing between day 19 and birth. Interestingly, rat SGLT2 mRNA is 2.6 kb before birth and 2.2 kb after birth, suggesting the presence of a different splice variant in embryonic kidney compared to the adult (You et al., *J. Biol. Chem.*, 1995, 270, 29365-29371).

The transport properties of rat SGLT2, i.e $K_m$ of 3.0 mM and sodium to glucose coupling of 1:1, are also characteristic of a kidney cortical low-affinity transport system. Hybrid depletion studies in which rat kidney superficial cortex mRNA was mixed with an antisense oligonucleotide corresponding to the 5' portion of the rat SGLT2 coding region completely suppressed the uptake of α-MeGlc in *Xenopus* oocytes into which the mRNA/oligonucleotide mix was injected. An antisense oligonucleotide targeted to SGLT1 had no effect on the uptake of α-MeGlc. These data demonstrate that the α-MeGlc uptake was entirely due to the expression of rat SGLT2 and support the proposal that SGLT2 is the major kidney cortical low affinity glucose transporter (You et al., *J. Biol. Chem.*, 1995, 270, 29365-29371).

A second low-affinity SGLT, named SAAT-pSGLT2, was isolated from porcine kidney cells and was initially proposed to be the main low-affinity glucose transporter. However, further studies have revealed that the molecular characteristics of SAAT-pSGLT2 differ from those of SGLT2 and consequently SAAT-pSGLT2 has been renamed SGLT3 (Kong et al., *J. Biol. Chem.*, 1993, 268, 1509-1512; Mackenzie et al., *J. Biol. Chem.*, 1996, 271, 32678-32683; Mackenzie et al., *J. Biol. Chem.*, 1994, 269, 22488-22491; You et al., *J. Biol. Chem.*, 1995, 270, 29365-29371). Whether SGLT3 contributes to glucose reabsorption in a physiologically relevant manner is unclear.

The importance of SGLT2 function was demonstrated in hepatocyte nuclear factor 1α (HNF 1α)-deficient animals, which are diabetic and also suffer from a renal Fanconi syndrome characterized by urinary glucose loss. HNF 1α is a transcriptional activator expressed in liver, kidney, pancreas and intestine. The renal defect in these mice is due to an 80-90% reduction in SGLT2 expression. Thus, HNF1α is one gene product that controls SGLT2 expression, which is essential to proper glucose reabsorption in vivo (Pontoglio et al., *EMBO Rep.*, 2000, 1, 359-365).

Reduction of SGLT2 mRNA was also observed upon exposure of mouse kidney cortical cells to cadmium, along with inhibition of sodium-dependent uptake of the glucose analog α-MeGlc. Interestingly, while both SGLT1 and SGLT2 mRNA were decreased in mouse kidney cortical cells exposed to cadmium, SGLT3 mRNA was upregulated, suggesting that individual SGLT species are not regulated in a similar manner (Tabatabai et al., *Toxicol. Appl. Pharmacol.*, 2001, 177, 163-173). Changes in glucose or sodium filtrated rate also modulate the expression of sodium-glucose transporter mRNA. Diabetic rats with glycosuria and rats fed a high sodium diet exhibited increased SGLT2 expression in the renal proximal tubule. The finding that SGLT1 levels in these rats were not altered to the same extent as SGLT2 levels further supports the hypothesis that the cotransporters are differentially regulated (Vestri et al., *J. Membr. Biol.*, 2001, 182, 105-112).

Although studies of SGLT function and localization in multiple mammalian species, including rat, mouse, pig, rabbit and dog, indicated that SGLT2 is the low-affinity renal SGLT, the identity of the human SGLT responsible for glucose reabsorption across the brush border of the human proximal tubule remained unclear. The lack of information describing SGLT protein localization in renal brush border further hindered the identification of the human low-affinity SGLT. Molecular genetic analysis of SGLT1 and SGLT2 indicated that a genetic alteration in the SGLT2 gene is a likely cause of renal glycosuria, a condition characterized by elevated excretion of glucose in the urine (Hediger et al., *Klin. Wochenschr.*, 1989, 67, 843-846). Direct evidence of SGLT function in the reabsorption of glucose came from analysis of the SGLT2 gene in a patient with congenital isolated renal glucosuria. Sequence analysis revealed a homozygous nonsense mutation in exon 11 of the SGLT2 gene leading to the formation of a truncated protein which is predicted to lack cotransport function (van den Heuvel et al., *Hum. Genet.*, 2002, 111, 544-547).

Whereas SGLT2 deficiency leads to inhibited reabsorption of glucose, SGLT2 elevation potentially allows for increased glucose uptake and is observed in metastatic lesions of lung cancer. Quantitation of SGLT2 gene expression revealed no significant difference between normal lung tissue and primary lung cancer. However, the metatstatic lesions of both the liver and lymph node exhibited significantly higher expression of SGLT2 (Ishikawa et al., *Jpn. J. Cancer Res.*, 2001, 92, 874-879). This finding is significant in light of evidence that different clinical tumors show significantly increased glucose uptake in vivo compared to normal tissue. Such a change in metabolism confers an advantage to tumor cells which allows them to survive and invade. Furthermore, glucose uptake correlates with tumor aggressiveness and prognosis (Dang and Semenza, *Trends Biochem. Sci.*, 1999, 24, 68-72).

Diabetes is a disorder characterized by hyperglycemia due to deficient insulin action. Chronic hyperglycemia is a major risk factor for diabetes-associated complications, including heart disease, retinopathy, nephropathy and neuropathy. As the kidneys play a major role in the regulation of plasma glucose levels, renal glucose transporters are becoming attractive drug targets (Wright, *Am. J. Physiol. Renal Physiol.*, 2001, 280, F10-18). Synthetic agents that are derived from phlorizin, a specific inhibitor of sodium/glucose transporters, have been designed and include T-1095, and its metabolically active form T-1095A (Tsujihara et al., *J. Med. Chem.*, 1999, 42, 5311-5324). Phlorizin, T-1095 and T-1095A all inhibited sodium-dependent glucose uptake in brush border membranes prepared from normal and diabetic rat kidney, rat small intestine, mouse kidney and dog kidney, as well as in *Xenopus* oocytes injected with human SGLT mRNA (Oku et al., *Diabetes*, 1999, 48, 1794-1800; Oku et al., *Eur. J. Pharmacol.*, 2000, 391, 183-192). These agents have been tested as antidiabetic compounds in laboratory animals with genetic and streptozotocin-induced diabetes. In these models, administration of these compounds inhibited renal SGLT activity, increased urinary glucose excretion and improved glucose tolerance, hyperglycemia and hypoinsulemia (Arakawa et al., *Br. J. Pharmacol.*, 2001, 132, 578-586; Oku et al., *Diabetes*, 1999, 48, 1794-1800; Oku et al., *Eur. J. Pharmacol.*, 2000, 391, 183-192). Prolonged treatment of db/db mice with T-1095 yielded similar results and also almost completely suppressed the increase of urinary albumin and improved renal glomeruli pathology, indicating a beneficial influence on renal disfunction and a protective effect against nephropathy, respectively (Arakawa et al., *Br. J. Pharmacol.*, 2001, 132, 578-586). Diabetic nephropathy is the most common cause of end-stage renal disease that develops in many patients with diabetes. In Zucker diabetic fatty rats, long-term treatment with T-1095 lowered both fed and fasting glucose levels to near normal ranges. Also observed were recovered hepatic glucose production and glucose utilization rates without a significant improvement in skeletal muscle glucose utilization rate, indicating that hyperglycemia contributes to insulin resistance in hepatic and adipose tissue in this rat model of diabetes. These results further suggest that glucotoxicity, which results from long-term hyperglycemia, induces tissue-dependent insulin resistance in diabetic patients (Nawano et al., *Am. J. Physiol. Endocrinol. Metab.*, 2000, 278, E535-543).

Other SGLT2 inhibiting compounds are known in the art, such as the c-aryl glucosides disclosed in U.S. Pat. No. 6,414,126, which are inhibitors of sodium dependent glucose transporters found in the intestine and kidney and are proposed to treat diabetes, hyperglycemia and related diseases when used alone or in combination with other antidiabetic agents (Ellsworth et al., 2002).

The US pre-grant publication 20030055019 discloses isolated mutant proteins selected from a group which includes SGLT2, the corresponding nucleic acid molecules encoding said mutant proteins, isolated antisense derivatives of the nucleic acid sequences encoding said mutant proteins, as well as methods of delivering said antisense nucleic acid derivatives to treat or prevent hypertension, diabetes, insulin sensitivity, obesity, dyslipidemia and stroke. This application also discloses the antisense molecules may be DNA or RNA or a chimeric mixture, single-stranded or double-stranded or may comprise a ribozyme or catalytic RNA (Shimkets, 2003).

The European Patent Applications EP 1 293 569 and EP 1 308 459 disclose a polynucleotide comprising a protein-coding region of the nucleotide sequence of any one of a group of sequences which includes a nucleic acid sequence encoding human SGLT2, an oligonucleotide comprising at least 15 nucleotides complementary to the nucleotide sequence or to a complementary strand thereof and an antisense polynucleotide against the disclosed polynucleotide or a part thereof. These applications disclose the use of said antisense polynucleotides for suppressing the expression of a polypeptide of the invention and for gene therapy (Isogai et al., 2003; Isogai et al., 2003).

Although phlorizin and its derivatives are potent inhibitors of sodium-glucose cotransporters, these agents do not specifically inhibit a single species of SGLT, thus all SGLTs in all tissues are affected. Thus, there remains a need for therapeutic compounds that targets specific SGLT species. Antisense technology is an effective means for reducing the expression of specific gene products and may therefore prove to be uniquely useful in a number of therapeutic, diagnostic and research applications for the modulation of SGLT2 expression.

The present invention provides compounds and methods for modulating SGLT2 expression.

SUMMARY OF THE INVENTION

The present invention is directed to oligomeric compounds, especially nucleic acid and nucleic acid-like oligomers, such as antisense compounds, which are targeted to a nucleic acid encoding SGLT2, and which modulate the expression of SGLT2. Pharmaceutical and other compositions comprising the compounds of the invention are also provided. Further provided are methods of screening for modulators of SGLT2 and methods of modulating the expression of SGLT2 in cells, tissues or animals comprising contacting the cells, tissues or animals with one or more of the compounds or compositions of the invention. Further provided are diagnostic methods for identifying a disease state by identifying the presence of SGLT2 in a sample using one or more of the compounds of the invention. Methods of treating an animal, particularly a human, suspected of having or being prone to a disease or condition associated with expression of SGLT2 are also set forth herein. Such methods comprise administering a therapeutically or prophylactically effective amount of one or more of the compounds or compositions of the invention to the person, who may be in need of treatment.

Also provided are methods of enhancing inhibition of expression of preselected cellular RNA targets in kidney cells and kidney tissue using compounds, such as antisense compounds, of the invention. Further provided are methods of preventing or delaying the onset of a disease or condition in an animal, wherein the disease or condition is associated with expression of a preselected cellular RNA target expressed in the kidney, particularly SGLT2. Methods of lowering blood glucose levels in an animal and methods of delaying or preventing the onset of type 2 diabetes also are set forth herein. Such methods comprise administering a therapeutically or prophylactically effective amount of one or more of the compounds of the invention to the animal, which may be in need of treatment. Provided herein are methods of enhancing inhibition of expression of SGLT2 in kidney cells or kidney tissues, comprising contacting the cells or tissues with one or more of the compounds of the invention, such as antisense compounds.

DETAILED DESCRIPTION OF THE INVENTION

The present invention employs oligomeric compounds, preferably oligonucleotides and similar species, such as antisense compounds, for use in modulating the function or effect of nucleic acid molecules encoding SGLT2. This is accomplished by providing oligomeric compounds, such as oligonucleotides, which specifically hybridize with one or more nucleic acid molecules encoding SGLT2.

In one embodiment, the oligomeric compounds of the invention are chimeric oligonucleotides ("gapmers"), composed of a central "gap" region consisting of 2'-deoxynucleotides, which is flanked on both sides (5' and 3' directions) by "wings" composed of 2'-methoxyethyl (2'-MOE) nucleotides. In some embodiments, the internucleoside (backbone) linkages are phosphorothioate (P=S) throughout the oligonucleotide. In some embodiments, one or more cytidine residues are 5-methylcytidines.

In another embodiment, the oligomeric compounds of the invention are chimeric oligonucleotides having mixed phosphorothioate and phosphodiester backbones, referred to herein as "mixed backbone compounds." The mixed backbone compounds of the invention can have a central "gap" region consisting of at least 5 contiguous 2'-deoxy nucleosides flanked by two "wing" regions consisting of at least one 2'-O-methoxyethyl nucleoside in each region. The internucleoside linkages of the mixed backbone compounds can be phosphorothioate linkages in the central "gap" region and phosphodiester linkages in the two "wing" regions. In another embodiment, mixed backbone compounds have phosphodiester linkages in the "wing" regions except for one phosphodiester linkage at one or both of the extreme 5' and 3' ends of the oligonucleotide.

It is shown herein that mixed backbone compounds are efficiently delivered to the kidney and treatment with the mixed backbone compounds results in efficient modulation of target gene expression in the kidney without liver or kidney toxicity. It is further shown herein that treatment with mixed backbone compounds in animal models of type 2 diabetes reduces blood glucose levels in diabetic animals.

As used herein, the terms "target nucleic acid" and "nucleic acid molecule encoding SGLT2" have been used for convenience to encompass DNA encoding SGLT2, RNA (including pre-mRNA and mRNA or portions thereof) transcribed from such DNA, and also cDNA derived from such RNA. The hybridization of a compound of this invention with its target nucleic acid is generally referred to as "antisense." Consequently, one mechanism believed to be included in the practice of some embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, specific nucleic acid molecules and their functions can be targeted for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as, for example, translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. One result of such interference with target nucleic acid function is modulation of the expression of SGLT2. In the context of the present invention, "modulation" and "modulation of expression" mean either an increase (stimulation) or a decrease (inhibition) in the amount or levels of a nucleic acid molecule encoding the gene, e.g., DNA or RNA. Inhibition is often the desired form of modulation of expression and mRNA is often a desired target nucleic acid.

In the context of this invention, "hybridization" means the pairing of complementary strands of oligomeric compounds. In the present invention, one mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An oligomeric compound, such as an antisense compound, is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

In the present invention the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated.

"Complementary," as used herein, refers to the capacity for precise pairing between two nucleobases of an oligomeric compound. For example, if a nucleobase at a certain position of an oligonucleotide (an oligomeric compound), is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an oligomeric compound need not be 100% complementary to that of its target nucleic acid to be specifically hybridizable. Moreover, an oligomeric compound may hybridize over one or more segments such that intervening or adjacent segments are not involved in the hybridization event (e.g., a loop structure or hairpin structure). The antisense compounds of the present invention can comprise at least 70%, at least 75%, at least 80%, at least 85%, at least 90%, at least 95%, or at least 99% sequence complementarity to the target region within the target nucleic acid sequence to which they are targeted. For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.*, 1990, 215, 403-410; Zhang and Madden, *Genome Res.*, 1997, 7, 649-656).

Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). In some embodiments, homology, sequence identity or complementarity, between the oligomeric and target is from about 50% to about 60%, from about 60% to about 70%, from about 70% to about 80%, from about 80% to about 90%, about 90%, about 92%, about 94%, about 95%, about 96%, about 97%, about 98%, about 99%, or about 100%. As used herein, the term "about" means±5% of the value modified.

According to the present invention, oligomeric compounds, such as antisense compounds, include antisense oligomeric compounds, antisense oligonucleotides, ribozymes, external guide sequence (EGS) oligonucleotides, alternate splicers, and other oligomeric compounds which hybridize to at least a portion of the target nucleic acid. As such, these compounds may be introduced in the form of single-stranded, double-stranded, circular or hairpin oligomeric compounds and may contain structural elements such as internal or terminal bulges or loops. Once introduced to a system, the compounds of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While one form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, *Caenorhabditis elegans* (Guo and Kempheus, *Cell,* 1995, 81, 611-620). Montgomery et al. have shown that the primary interference effects of dsRNA are posttranscriptional (Montgomery et al., *Proc. Natl. Acad. Sci. USA,* 1998, 95, 15502-15507). The posttranscriptional antisense mechanism defined in *Caenorhabditis elegans* resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., *Nature,* 1998, 391, 806-811). Recently, it has been shown that it is, in fact, the single-stranded RNA oligomers of antisense polarity of the dsRNAs which are the potent inducers of RNAi (Tijsterman et al., *Science,* 2002, 295, 694-697).

The oligomeric compounds of the present invention also include modified compounds in which a different base is present at one or more of the nucleotide positions in the compound. For example, if the first nucleotide is an adenosine, modified compounds may be produced which contain thymidine, guanosine or cytidine at this position. This may be done at any of the positions of the antisense compound. These compounds are then tested using the methods described herein to determine their ability to inhibit expression of SGLT2 mRNA.

In the context of this invention, the term "oligomeric compound" refers to a polymer or oligomer comprising a plurality of monomeric units. In the context of this invention, the term "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often desired over native forms because of desirable properties such as, for example, enhanced cellular uptake, enhanced affinity for a target nucleic acid and increased stability in the presence of nucleases.

While oligonucleotides are one form of the antisense compounds of this invention, the present invention comprehends other families of antisense compounds as well, including but not limited to oligonucleotide analogs and mimetics such as those described herein.

The antisense compounds in accordance with this invention can comprise from about 8 to about 80 nucleobases (i.e. from about 8 to about 80 linked nucleosides). One of ordinary skill in the art will appreciate that the invention embodies compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length, or any range therewithin.

In one embodiment, the antisense compounds of the invention are 10 to 50 nucleobases in length. One having ordinary skill in the art will appreciate that this embodies compounds of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleobases in length, or any range therewithin.

In another embodiment, the antisense compounds of the invention are 13 to 30 nucleobases in length. One having ordinary skill in the art will appreciate that this embodies compounds of 13, 14, 15, 16, 17, 18, 19, 20, 21, 22, 23, 24, 25, 26, 27, 28, 29 or 30 nucleobases in length, or any range therewithin.

In another embodiment, the antisense compounds of the invention are 15 to 25 nucleobases in length. One having ordinary skill in the art will appreciate that this embodies compounds of 15, 16, 17, 18, 19, 20, 21, 22, 23, 24 or 25 nucleobases in length, or any range therewithin.

In another embodiment, the antisense compounds of the invention are 18 to 22 nucleobases in length. One having ordinary skill in the art will appreciate that this embodies compounds of 18, 19, 20, 21 or 22 nucleobases in length, or any range therewithin.

Particularly suitable compounds are oligonucleotides from about 10 to about 50 nucleobases, from about 13 to about 30 nucleobases, from about 15 to about 25, and from about 18 to about 22 nucleobases.

Antisense compounds 8 to 80 nucleobases in length comprising a stretch of at least eight (8) consecutive nucleobases selected from within the illustrative antisense compounds are considered to be suitable antisense compounds as well.

Exemplary antisense compounds include oligonucleotide sequences that comprise at least the 8 consecutive nucleobases from the 5'-terminus of one of the illustrative antisense compounds (the remaining nucleobases being a consecutive stretch of the same oligonucleotide beginning immediately upstream of the 5'-terminus of the antisense compound which is specifically hybridizable to the target nucleic acid and continuing until the oligonucleotide contains about 8 to about 80 nucleobases). Similarly suitable antisense compounds are represented by oligonucleotide sequences that comprise at least the 8 consecutive nucleobases from the 3'-terminus of one of the illustrative antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains about 8 to about 80 nucleobases). It is also understood that antisense compounds may be represented by oligonucleotide sequences that comprise at least 8 consecutive nucleobases from an internal portion of the sequence of an illustrative antisense compound, and may extend in either or both directions until the oligonucleotide contains about 8 to about 80 nucleobases.

One having skill in the art armed with the antisense compounds illustrated herein will be able, without undue experimentation, to identify additional antisense compounds.

"Targeting" an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes SGLT2.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding SGLT2, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a suitable region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. It is also suitable to target the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also suitable target sites. mRNA transcripts produced via the process of splicing of two (or more) mRNAs from different gene sources are known as "fusion transcripts." It is also known that introns can be effectively targeted using antisense compounds targeted to, for example, DNA or pre-mRNA.

It is also known in the art that alternative RNA transcripts can be produced from the same genomic region of DNA. These alternative transcripts are generally known as "variants." More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants." Consequently, mRNA variants are processed pre-mRNA variants and each unique pre-mRNA variant must always produce a unique mRNA variant as a result of splicing. These mRNA variants are also known as "alternative splice variants." If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also suitable target nucleic acids.

The locations on the target nucleic acid to which the antisense compounds hybridize are hereinbelow referred to as "suitable target segments." As used herein the term "suitable target segment" is defined as at least an 8-nucleobase portion of a target region to which an active antisense compound is targeted. While not wishing to be bound by theory, it is presently believed that these target segments represent portions of the target nucleic acid which are accessible for hybridization.

While the specific sequences of certain preferred target segments are set forth herein, one of skill in the art will recognize that these serve to illustrate and describe particular embodiments within the scope of the present invention. Additional target segments may be identified by one having ordinary skill.

Target segments 8-80 nucleobases in length comprising a stretch of at least eight (8) consecutive nucleobases selected from within the illustrative target segments are considered to be suitable for targeting as well.

Target segments can include DNA or RNA sequences that comprise at least the 8 consecutive nucleobases from the 5'-terminus of one of the illustrative target segments (the remaining nucleobases being a consecutive stretch of the same DNA or RNA beginning immediately upstream of the 5'-terminus of the target segment and continuing until the DNA or RNA contains about 8 to about 80 nucleobases).

Target segments are also represented by DNA or RNA sequences that comprise at least the 8 consecutive nucleobases from the 3'-terminus of one of the illustrative target segments (the remaining nucleobases being a consecutive stretch of the same DNA or RNA beginning immediately downstream of the 3'-terminus of the target segment and continuing until the DNA or RNA contains about 8 to about 80 nucleobases). It is also understood that antisense target segments may be represented by DNA or RNA sequences that comprise at least 8 consecutive nucleobases from an internal portion of the sequence of an illustrative target segment, and may extend in either or both directions until the oligonucleotide contains about 8 to about 80 nucleobases. One having skill in the art armed with the target segments illustrated herein will be able, without undue experimentation, to identify further target segments.

Once one or more target regions, segments or sites have been identified, antisense compounds are chosen which are sufficiently complementary to the target, i.e., hybridize sufficiently well and with sufficient specificity, to give the desired effect.

The oligomeric antisense compounds may also be targeted to regions of the target nucleobase sequence (e.g., such as those disclosed in Example 16) comprising nucleobases 1-80, 81-160, 161-240, 241-320, 321-400, 401-480, 481-560, 561-640, 641-720, 721-800, 801-880, 881-960, 961-1040, 1041-1120, 1121-1200, 1201-1280, 1281-1360, 1361-1440, 1441-1520, 1521-1600, 1601-1680, 1681-1760, 1761-1840, 1841-1920, 1921-2000, 2001-2080, 2081-2160, 2161-2240, 2241-2273, or any combination thereof.

In a further embodiment, the "suitable target segments" identified herein may be employed in a screen for additional compounds that modulate the expression of SGLT2. "Modulators" are those compounds that decrease or increase the expression of a nucleic acid molecule encoding SGLT2 and which comprise at least an 8-nucleobase portion which is complementary to a target segment. The screening method comprises the steps of contacting a target segment of a nucleic acid molecule encoding SGLT2 with one or more candidate modulators, and selecting for one or more candidate modulators which decrease or increase the expression of a nucleic acid molecule encoding SGLT2. Once it is shown that the candidate modulator or modulators are capable of modulating (e.g. either decreasing or increasing) the expression of a nucleic acid molecule encoding SGLT2, the modulator may then be employed in further investigative studies of the function of SGLT2, or for use as a research, diagnostic, or therapeutic agent in accordance with the present invention.

The target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processsing via an antisense mechanism. Moreover, the double-stranded moieties may be subject to chemical modifications (Fire et al., *Nature*, 1998, 391, 806-811; Timmons and Fire, *Nature* 1998, 395, 854; Timmons et al., *Gene*, 2001, 263, 103-112; Tabara et al., *Science*, 1998, 282, 430-431; Montgomery et al., *Proc. Natl. Acad. Sci. USA*, 1998, 95, 15502-15507; Tuschl et al., *Genes Dev.*, 1999, 13, 3191-3197; Elbashir et al., *Nature*, 2001, 411, 494-498; Elbashir et al., *Genes Dev.* 2001, 15, 188-200). For example, such double-stranded moieties have been shown to inhibit the target by the classical hybridization of antisense strand of the duplex to the target, thereby triggering enzymatic degradation of the target (Tijsterman et al., *Science,* 2002, 295, 694-697).

The antisense compounds of the present invention can also be applied in the areas of drug discovery and target validation. The present invention comprehends the use of the compounds and target segments identified herein in drug discovery efforts to elucidate relationships that exist between SGLT2 and a disease state, phenotype, or condition. These methods include detecting or modulating SGLT2 comprising contacting a sample, tissue, cell, or organism with the compounds of the present invention, measuring the nucleic acid or protein level of SGLT2 and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

The antisense compounds of the present invention can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics, the compounds of the present invention, either alone or in combination with other compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.,* 2000, 480, 17-24; Celis, et al., *FEBS Lett.,* 2000, 480, 2-16), SAGE (serial analysis of gene expression) (Madden, et al., *Drug Discov. Today,* 2000, 5, 415-425), READS (restriction enzyme amplification of digested cDNAs) (Prashar and Weissman, *Methods Enzymol.,* 1999, 303, 258-72), TOGA (total gene expression analysis) (Sutcliffe, et al., *Proc. Natl. Acad. Sci. U.S.A.,* 2000, 97, 1976-81), protein arrays and proteomics (Celis, et al., *FEBS Lett.,* 2000, 480, 2-16; Jungblut, et al., *Electrophoresis,* 1999, 20, 2100-10), expressed sequence tag (EST) sequencing (Celis, et al., *FEBS Lett.,* 2000, 480, 2-16; Larsson, et al., *J. Biotechnol.,* 2000, 80, 143-57), subtractive RNA fingerprinting (SuRF) (Fuchs, et al., *Anal. Biochem.,* 2000, 286, 91-98; Larson, et al., *Cytometry,* 2000, 41, 203-208), subtractive cloning, differential display (DD) (Jurecic and Belmont, *Curr. Opin. Microbiol.,* 2000, 3, 316-21), comparative genomic hybridization (Carulli, et al., *J. Cell Biochem. Suppl.,* 1998, 31, 286-96), FISH (fluorescent in situ hybridization) techniques (Going and Gusterson, *Eur. J. Cancer,* 1999, 35, 1895-904)

and mass spectrometry methods (To, *Comb. Chem. High Throughput Screen*, 2000, 3, 235-41).

The antisense compounds of the invention are useful for research and diagnostics, because these compounds hybridize to nucleic acids encoding SGLT2. For example, oligonucleotides that are shown to hybridize with such efficiency and under such conditions as disclosed herein as to be effective SGLT2 inhibitors will also be effective primers or probes under conditions favoring gene amplification or detection, respectively. These primers and probes are useful in methods requiring the specific detection of nucleic acid molecules encoding SGLT2 and in the amplification of said nucleic acid molecules for detection or for use in further studies of SGLT2. Hybridization of the antisense oligonucleotides, particularly the primers and probes, of the invention with a nucleic acid encoding SGLT2 can be detected by means known in the art. Such means may include conjugation of an enzyme to the oligonucleotide, radiolabelling of the oligonucleotide or any other suitable detection means. Kits using such detection means for detecting the level of SGLT2 in a sample may also be prepared.

The specificity and sensitivity of antisense is also harnessed by those of skill in the art for therapeutic uses. Antisense compounds have been employed as therapeutic moieties in the treatment of disease states in animals, including humans. Antisense oligonucleotide drugs, including ribozymes, have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an animal, such as a human, suspected of having a disease or disorder which can be treated by modulating the expression of SGLT2 is treated by administering antisense compounds in accordance with this invention. For example, in one non-limiting embodiment, the methods comprise the step of administering to the animal a therapeutically effective amount of a SGLT2 inhibitor. The animal may or may not have already been identifies as being in need of treatment. That is, the animal may or may not have been diagnosed with a particular disease or disorder. The SGLT2 inhibitors of the present invention effectively inhibit the activity of the SGLT2 protein or inhibit the expression of the SGLT2 protein. In some embodiments, the activity or expression of SGLT2 in an animal or cell is inhibited by at least about 10%, by at least about 20%, by at least about 30%, by at least about 40%, by at least about 50%, by at least about 60%, by at least about 70%, by at least about 75%, by at least about 80%, by at least about 85%, by at least about 90%, by at least about 95%, by at least about 97%, by at least about 99%, or by 100%.

For example, the reduction of the expression of SGLT2 may be measured in serum, adipose tissue, liver or any other body fluid, tissue or organ of the animal. The cells contained within the fluids, tissues or organs being analyzed can contain a nucleic acid molecule encoding SGLT2 protein and/or the SGLT2 protein itself.

The antisense compounds of the invention can be utilized in pharmaceutical compositions by adding an effective amount of a compound to a suitable pharmaceutically acceptable diluent or carrier. Use of the compounds and methods of the invention may also be useful prophylactically.

As is known in the art, a nucleoside is a base-sugar combination. The base portion of the nucleoside is normally a heterocyclic base sometimes referred to as a "nucleobase" or simply a "base." The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally desired. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Internucleoside Linkages (Backbones)

Specific examples of antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Modified oligonucleotide backbones containing a phosphorus atom therein include, for example, phosphorothioates, chiral phosphorothioates, phosphorodithioates, phosphotriesters, aminoalkylphosphotriaminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity can comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050.

Modified oligonucleotide backbones that do not include a phosphorus atom therein can have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones;

riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439.

Modified Sugar and Internucleoside Linkages-Mimetics

In other antisense compounds, e.g., oligonucleotide mimetics, both the sugar and the internucleoside linkage (i.e. the backbone), of the nucleotide units are replaced with novel groups. The nucleobase units are maintained for hybridization with an appropriate target nucleic acid. One such compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719, 262. Further teaching of PNA compounds can be found in Nielsen et al., *Science,* 1991, 254, 1497-1500.

Some embodiments of the invention include oligonucleotides with phosphorothioate backbones and oligonucleosides with heteroatom backbones, and in particular —$CH_2$—NH—O—$CH_2$—, —$CH_2$—N($CH_3$)—O—$CH_2$— (known as a methylene (methylimino) or MMI backbone), —$CH_2$—O—N($CH_3$)—$CH_2$—, —$CH_2$—N($CH_3$)—N($CH_3$)—$CH_2$— and —O—N($CH_3$)—$CH_2$—$CH_2$— (wherein the native phosphodiester backbone is represented as —O—P—O—$CH_2$—) of the above referenced U.S. Pat. No. 5,489,677, and the amide backbones of the above referenced U.S. Pat. No. 5,602,240. Also suitable are oligonucleotides having morpholino backbone structures of the above-referenced U.S. Pat. No. 5,034,506.

Modified Sugars

Modified antisense compounds may also contain one or more substituted sugar moieties. Antisense compounds, such as antisense oligonucleotides, can comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Also suitable are O(($CH_2$)$_n$O)$_m$$CH_3$, O($CH_2$)$_n$$OCH_3$, O($CH_2$)$_n$$NH_2$, O($CH_2$)$_n$$CH_3$, O($CH_2$)$_n$$ONH_2$, and O($CH_2$)$_n$ON(($CH_2$)$_n$$CH_3$)$_2$, where n and m are from 1 to about 10. Other oligonucleotides can comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. One modification includes 2'-methoxyethoxy (2'-O—$CH_2CH_2OCH_3$, also known as 2'-O-(2-methoxyethyl) or 2'-MOE) (Martin et al., *Helv. Chim. Acta,* 1995, 78, 486-504) i.e., an alkoxyalkoxy group. Another modification includes 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—N($CH_3$)$_2$, also described in examples hereinbelow.

Other modifications include 2'-methoxy (2'-O—$CH_3$), 2'-aminopropoxy (2'-$OCH_2CH_2CH_2NH_2$), 2'-allyl (2'-$CH_2$—CH=$CH_2$), 2'-O-allyl(2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Antisense compounds may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319, 080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920.

Another modification of the sugar includes Locked Nucleic Acids (LNAs) in which the 2'-hydroxyl group is linked to the 3' or 4' carbon atom of the sugar ring, thereby forming a bicyclic sugar moiety. The linkage can be a methylene (—$CH_2$—), group bridging the 2' oxygen atom and the 4' carbon atom wherein n is 1 or 2. LNAs and preparation thereof are described in WO 98/39352 and WO 99/14226.

Natural and Modified Nucleobases

Antisense compounds may also include nucleobase (often referred to in the art as heterocyclic base or simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido(5,4-b)(1,4)benzoxazin-2(3H)-one), phenothiazine cytidine (1H-pyrimido(5,4-b)(1, 4)benzothiazin-2(3H)-one), G-clamps such as a substituted phenoxazine cytidine (e.g. 9-(2-aminoethoxy)-H-pyrimido (5,4-b)(1,4)benzoxazin-2(3H)-one), carbazole cytidine (2H-pyrimido(4,5-b)indol-2-one), pyridoindole cytidine (H-pyrido(3',':4,5)pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are particularly useful for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently suitable base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941, and U.S. Pat. No. 5,750,692.

Conjugates

Another modification of the antisense compounds of the invention involves chemically linking to the antisense compound one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups of the invention include, but are not limited to, intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include, but are not limited to, cholesterols, lipids, phospholipids, biotin, phenazine, folate, phenanthridine, anthraquinone, acridine, fluoresceins, rhodamines, coumarins, and dyes. Groups that enhance the pharmaco-dynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. No. 6,287,860. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Antisense compounds of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999).

Representative U.S. patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Chimeric Compounds

It is not necessary for all positions in a given compound to be uniformly modified, and in fact more than one of the aforementioned modifications may be incorporated in a single compound or even at a single nucleoside within an oligonucleotide.

The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. Chimeric antisense oligonucleotides are thus a form of antisense compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative U.S. patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922.

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative U.S. patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756.

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, examples of pharmaceutically acceptable salts and their uses are further described in U.S. Pat. No. 6,287,860. Potassium and sodium salts are typical salts.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogenous systems of one liquid dispersed in another in the form of droplets usually exceeding 0.1 μm in diameter. Emulsions may contain additional components in addition to the dispersed phases, and the active drug which may be present as a solution in either the aqueous phase, oily phase or itself as a separate phase. Microemulsions are included as an embodiment of the present invention. Emulsions and their uses are well known in the art and are further described in U.S. Pat. No. 6,287,860.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The pharmaceutical formulations and compositions of the present invention may also include surfactants. The use of surfactants in drug products, formulations and in emulsions is well known in the art. Surfactants and their uses are further described in U.S. Pat. No. 6,287,860.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860.

One of skill in the art will recognize that formulations are routinely designed according to their intended use, i.e. route of administration.

Formulations for topical administration include those in which the oligonucleotides of the invention are in admixture with a topical delivery agent such as lipids, liposomes, fatty acids, fatty acid esters, steroids, chelating agents and surfactants. Lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Fatty acids and esters, pharmaceutically acceptable salts thereof, and their uses are further described in U.S. Pat. No. 6,287,860. Topical formulations are described in detail in U.S. patent application Ser. No. 09/315,298 filed on May 20, 1999.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Suitable oral formulations are those in which oligonucleotides of the invention are administered in conjunction with one or more penetration enhancers surfactants and chelators. Surfactants include fatty acids and/or esters or salts thereof, bile acids and/or salts thereof. Bile acids/salts and fatty acids and their uses are further described in U.S. Pat. No. 6,287,860. Also suitable are combinations of penetration enhancers, for example, fatty acids/salts in combination with bile acids/salts. A particularly suitable combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860. Oral formulations for oligonucleotides and their preparation are described in detail in U.S. application Ser. Nos. 09/108,673 (filed Jul. 1, 1998), 09/315,298 (filed May 20, 1999) and 10/071,822, filed Feb. 8, 2002 and published as U.S. Application No. 2003-0027780.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oligomeric compounds and one or more other chemotherapeutic agents which function by a non-antisense mechanism. Examples of such chemotherapeutic agents include, but are not limited to, cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs including, but not limited to, nonsteroidal anti-inflammatory drugs and corticosteroids, and antiviral drugs including, but not limited to, ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Alternatively, compositions of the invention may contain two or more antisense compounds targeted to different regions of the same nucleic acid target. Numerous examples of antisense compounds are known in the art. Two or more combined compounds may be used together or sequentially.

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 mg to 100 g per kg of body weight, from 0.1 µg to 10 g per kg of body weight, from 1 µg to 1 g per kg of body weight, from 10 µg to 100 mg per kg of body weight, from 100 µg to 10 mg per kg of body weight, or from 100 mg to 1 mg per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.0001 µg to 100 g per kg of body weight, once or more daily, to once every 20 years.

In order that the invention disclosed herein may be more efficiently understood, examples are provided below. It should be understood that these examples are for illustrative purposes only and are not to be construed as limiting the invention in any manner. Throughout these examples, molecular cloning reactions, and other standard recombinant DNA techniques, were carried out according to methods described in Maniatis et al., Molecular Cloning—A Laboratory Manual, 2nd ed., Cold Spring Harbor Press (1989), using commercially available reagents, except where otherwise noted.

EXAMPLES

Example 1

Synthesis of Nucleoside Phosphoramidites

The following compounds, including amidites and their intermediates were prepared as described in U.S. Pat. No. 6,426,220 and published PCT WO 02/36743; 5'-O-Dimethoxytrityl-thymidine intermediate for 5-methyl dC amidite, 5'-O-Dimethoxytrityl-T-deoxy-5-methylcytidine intermediate for 5-methyl-dC amidite, 5'-O-Dimethoxytrityl-2'-deoxy-N4-benzoyl-5-methylcytidine penultimate intermediate for 5-methyl dC amidite, (5'-O-(4,4'-Dimethoxytriphenylmethyl)-2'-deoxy-N$^4$-benzoyl-5-methylcytidin-3'-O-yl)-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, (5'-O-(4,4'-Dimethoxytriphenylmethyl)-2'-O-(2-methoxyethyl)-5-methyluridin-3'-O-yl)-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-N$^4$-benzoyl-5-methyl-cytidine penultimate intermediate, (5'-O-(4,4'-Dimethoxytriphenylmethyl)-2'-O-(2-methoxyethyl)-N$^4$-benzoyl-5-methylcyfidin-3'-O-yl)-2-cyanoethyl-N,N-diisopropylphosphoramidite (MOE 5-Me-C amidite), (5'-O-(4,4'-Dimethoxytriphenylmethyl)-2'-O-(2-methoxyethyl)-N$^6$-benzoyladenosin-3'-O-yl)-2-cyanoethyl-N,N-diisopropylphosphoramidite (MOE A amdite), (5'-O-(4,4'-Dimethoxytriphenylmethyl)-2'-O-(2-methoxyethyl)-N$^4$-isobutyrylguanosin-3'-O-yl)-2-cyanoethyl-N,N-diisopropylphosphoramidite (MOE G amidite), 2'-O-(Aminooxyethyl) nucleoside amidites and 2'-O-(dimethylaminooxy-ethyl) nucleoside amidites, 2'-(Dimethylaminooxyethoxy) nucleoside amidites, 5'-O-tert-Butyldiphenylsilyl-O$^2$-2'-anhydro-5-methyluridine, 5'-O-tert-Butyldiphenylsilyl-2'-O-(2-hydroxyethyl)-5-methyluridine, 2'-O-((2-phthalimidoxy)ethyl)-5'-t-butyldiphenylsilyl-5-methyluridine, 5'-O-tert-butyldiphenylsilyl-2'-O-((2-formadoximinooxy)ethyl)-5-methyluridine, 5'-O-tert-Butyldiphenylsilyl-2'-O—(N,N dimethylaminooxyethyl)-5-methyluridine, 2'-β-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-((2-cyanoethyl)-N,N-diisopropylphosphoramidite), 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-((2-cyanoethyl)-N,N-diisopropylphosphoramidite), 2'-dimethylaminoethoxyethoxy (2'-DMAEOE) nucleoside amidites, 2'-O-(2(2-N,N-dimethylaminoethoxy)ethyl)-5-methyl uridine, 5'-O-dimethoxytrityl-2'-O-(2(2-N,N-dimethylaminoethoxy)-ethyl))-5-methyl uridine and 5'-O-Dimethoxytrityl-2'-O-(2(2-N,N-dimethylaminoethoxy)-ethyl))-5-methyl uridine-3'-O-(cyanoethyl-N,N-diisopropyl) phosphoramidite.

Example 2

Oligonucleotide and Oligonucleoside Synthesis

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.
Oligonucleotides:
Unsubstituted and substituted phosphodiester (P=O) oligonucleotides are synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation was effected by utilizing a 10% w/v solution of 3,H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12-16 hr), the oligonucleotides were recovered by precipitating with >3 volumes of ethanol from a 1 M NH$_4$OAc solution. Phosphinate oligonucleotides are prepared as described in U.S. Pat. No. 5,508,270.

Alkyl phosphonate oligonucleotides are prepared as described in U.S. Pat. No. 4,469,863.

3'-Deoxy-3'-methylene phosphonate oligonucleotides are prepared as described in U.S. Pat. Nos. 5,610,289 or 5,625,050.

Phosphoramidite oligonucleotides are prepared as described in U.S. Pat. Nos. 5,256,775 or 5,366,878.

Alkylphosphonothioate oligonucleotides are prepared as described in published PCT applications PCT/US94/00902 and PCT/US93/06976 (published as WO 94/17093 and WO 94/02499, respectively).

3'-Deoxy-3'-amino phosphoramidate oligonucleotides are prepared as described in U.S. Pat. No. 5,476,925.

Phosphotriester oligonucleotides are prepared as described in U.S. Pat. No. 5,023,243.

Borano phosphate oligonucleotides are prepared as described in U.S. Pat. Nos. 5,130,302 and 5,177,198.
Oligonucleosides:

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289.

Formacetal and thioformacetal linked oligonucleosides are prepared as described in U.S. Pat. Nos. 5,264,562 and 5,264,564.

Ethylene oxide linked oligonucleosides are prepared as described in U.S. Pat. No. 5,223,618.

Example 3

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group which, has the following important properties. It is stable to the conditions of nucleoside phosphoramidite synthesis and oligonucleotide synthesis. However, after oligonucleotide synthesis the oligonucleotide is treated with methylamine which not only cleaves the oligonucleotide from the solid support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe, S. A., et al., *J. Am. Chem. Soc.,* 1998, 120, 11820-11821; Matteucci, M. D. and Caruthers, M. H. *J. Am. Chem. Soc.,* 1981, 103, 3185-3191; Beaucage, S. L. and Caruthers, M. H. *Tetrahedron Lett.,* 1981, 22, 1859-1862; Dahl, B. J., et al., *Acta Chem. Scand.,* 1990, 44, 639-641; Reddy, M. P., et al., *Tetrahedrom Lett.,* 1994, 25, 4311-4314; Wincott, F. et al., *Nucleic Acids Res.,* 1995, 23, 2677-2684; Griffin, B. E., et al., *Tetrahedron,* 1967, 23, 2301-2313; Griffin, B. E., et al., *Tetrahedron,* 1967, 23, 2315-2331).

RNA antisense compounds (RNA oligonucleotides) of the present invention can be synthesized by the methods herein or purchased from Dharmacon Research, Inc (Lafayette, Colo.). Once synthesized, complementary RNA antisense compounds can then be annealed by methods known in the art to form double stranded (duplexed) antisense compounds. For example, duplexes can be formed by combining 30 μl of each of the complementary strands of RNA oligonucleotides (50 uM RNA oligonucleotide solution) and 15 μl of 5× annealing buffer (100 mM potassium acetate, 30 mM HEPES-KOH pH 7.4, 2 mM magnesium acetate) followed by heating for 1 minute at 90° C., then 1 hour at 37° C. The resulting duplexed antisense compounds can be used in kits, assays, screens, or other methods to investigate the role of a target nucleic acid, or for diagnostic or therapeutic purposes.

Example 4

Synthesis of Chimeric Compounds

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

(2'-O-Me)-(2'-deoxy)-(2'-O-Me) Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 394, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia ($NH_4OH$) for 12-16 hr at 55° C. The deprotected oligo is then recovered by an appropriate method (precipitation, column chromatography, volume reduced in vacuo and analyzed spetrophotometrically for yield and for purity by capillary electrophoresis and by mass spectrometry.

(2'-O-(2-Methoxyethyl))-(2'-deoxy)-(2'-O-(Methoxyethyl) Chimeric Phosphorothioate Oligonucleotides (2'-O-(2-methoxyethyl))-(2'-deoxy)-(2'-O-(methoxyethyl)) chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

(2'-O-(2-Methoxyethyl)Phosphodiester)-(2'-deoxy Phosphorothioate)-(2'-O-(2-Methoxyethyl) Phosphodiester) Chimeric Oligonucleotides (2'-O-(2-methoxyethyl phosphodiester)-(2'-deoxy phosphorothioate)-(2'-β-(methoxyethyl) phosphodiester) chimeric oligonucleotides are prepared as per the above procedure for the 2'-O-methyl chimeric oligonucleotide with the substitution of 2'-O-(methoxyethyl) amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 5

Design and Screening of Duplexed Antisense Compounds Targeting SGLT2

In accordance with the present invention, a series of nucleic acid duplexes comprising the antisense compounds of the present invention and their complements can be designed to target SGLT2. The nucleobase sequence of the antisense strand of the duplex comprises at least an 8-nucleobase portion of an oligonucleotide in Table 1. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini.

For example, a duplex comprising an antisense strand having the sequence CGAGAGGCGGACGGGACCG (SEQ ID NO: 268) and having a two-nucleobase overhang of deoxythymidine(dT) would have the following structure:

```
cgagaggcggacgggaccgTT  Antisense Strand
|||||||||||||||||||    (SEQ ID NO: 269)
TTgctctccgcctgccctggc  Complement (SEQ ID NO:270)
```

In another embodiment, a duplex comprising an antisense strand having the same sequence CGAGAGGCGGACGGGACCG (SEQ ID NO: 268) may be prepared with blunt ends (no single stranded overhang) as shown:

```
cgagaggcggacgggaccg   Antisense Strand
|||||||||||||||||||   (SEQ ID NO: 268)
gctctccgcctgccctggc   Complement (SEQ ID NO:271)
```

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 µM. Once diluted, 30 µL of each strand is combined with 154, of a 5× solution of annealing buffer. The final concentration of said buffer is 100 mM potassium acetate, 30 mM HEPES-KOH pH 7.4, and 2 mM magnesium acetate. The final volume is 75 µl, This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 µM. This solution can be stored frozen (−20° C.) and freeze-thawed up to 5 times.

Once prepared, the duplexed antisense compounds are evaluated for their ability to modulate SGLT2 expression.

When cells reached 80% confluency, they are treated with duplexed antisense compounds of the invention. For cells grown in 96-well plates, wells are washed once with 200 µL OPTI-MEM-1 reduced-serum medium (Gibco BRL) and then treated with 130 µL of OPTI-MEM-1 containing 12 µg/mL LIPOFECTIN (Gibco BRL) and the desired duplex antisense compound at a final concentration of 200 nM. After 5 hours of treatment, the medium is replaced with fresh medium. Cells are harvested 16 hours after treatment, at which time RNA is isolated and target reduction measured by RT-PCR.

Example 6

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M $NH_4OAc$ with >3 volumes of ethanol. Synthesized oligonucleotides were analyzed by electrospray mass spectroscopy (molecular weight determination) and by capillary gel electrophoresis and judged to be at least 70% full length material. The relative amounts of phosphorothioate and phosphodiester linkages obtained in the synthesis was determined by the ratio of correct molecular weight relative to the −16 amu product (+/−32+/−48). For some studies oligonucleotides were purified by HPLC, as described by Chiang et al., J. Biol. Chem. 1991, 266, 18162-18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated $NH_4OH$ at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 8

Oligonucleotide Analysis—96-Well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE™ MDQ) or, for individually prepared samples, on a commercial CE apparatus (e.g., Beckman-P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence. Cells were seeded into 96-well plates (Falcon-Primaria #353872) at a density of 7000 cells/well for use in RT-PCR analysis.

A549 Cells:

The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence.

NHDF Cells:

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

HK-2 Cells:

HK-2 (human kidney 2) is a proximal tubular cell (PTC) line derived from normal kidney cells immortalized by transduction with human papilloma virus 16 (HPV-16) E6/E7 genes (CRL-2190, American Type Culture Collection, Manassus, Va.). HK-2 cells were routinely cultured in Keratinocyte-Serum Free Medium (17005-042, Invitrogen Corporation, Carlsbad, Calif.) which includes 5 ng/ml recombinant epidermal growth factor and 0.05 mg/ml bovine pituitary extract. Cells were routinely passaged by trypsinization and split at a ratio of 1:4 when they reached 70-80% confluence. One day prior to transfection, cells were seeded into 96-well plates (Falcon-Primaria #353872, BD Biosciences, Bedford, Mass.) at a density of 10,000 cells/well.

b.END Cells:

The mouse brain endothelial cell line b.END was obtained from Dr. Werner Risau at the Max Plank Instititute (Bad Nauheim, Germany). b.END cells were routinely cultured in DMEM, high glucose (Gibco/Life Technologies, Gaithersburg, Md.) supplemented with 10% fetal calf serum (Gibco/Life Technologies, Gaithersburg, Md.). Cells were routinely passaged by trypsinization and dilution when they reached 90% confluence. Cells were seeded into 96-well plates (Falcon-Primaria #3872) at a density of 3000 cells/well for use in RT-PCR analysis.

Treatment with Antisense Compounds:

When cells reached 65-75% confluency, they were treated with oligonucleotide. For cells grown in 96-well plates, wells were washed once with 100 µL OPTI-MEM™-1 reduced-serum medium (Invitrogen Corporation, Carlsbad, Calif.) and then treated with 130 µL of OPTI-MEM™-1 containing 3.75 mg/mL LIPOFECTIN™ (Invitrogen Corporation, Carlsbad, Calif.) and the desired concentration of oligonucleotide. Cells are treated and data are obtained in triplicate. After 4-7 hours of treatment at 37° C., the medium was replaced with fresh medium. Cells were harvested 16-24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is selected from either ISIS 13920 (TCCGTCATCGCTCCTCAGGG, SEQ ID NO: 1) which is targeted to human H-ras, or ISIS 18078, (GTGCGCGCGAGCCCGAAATC, SEQ ID NO: 2) which is targeted to human Jun-N-terminal kinase-2 (JNK2). Both controls are 2'-O-methoxyethyl gapmers (2'-O-methoxyethyls shown in bold) with a phosphorothioate backbone. For mouse or rat cells the positive control oligonucleotide is ISIS 15770, ATGCATTCTGCCCCCAAGGA, SEQ ID NO: 3, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-H-ras (for ISIS 13920), JNK2 (for ISIS 18078) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of c-H-ras, JNK2 or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

For Northern blotting or other analysis, cells may be seeded onto 100 mm or other standard tissue culture plates and treated similarly, using appropriate volumes of medium and oligonucleotide.

Example 10

Analysis of Oligonucleotide Inhibition of SGLT2 Expression

Antisense modulation of SGLT2 expression can be assayed in a variety of ways known in the art. For example, SGLT2 mRNA levels can be quantitated by, e.g., Northern blot analysis, competitive polymerase chain reaction (PCR), or real-time PCR(RT-PCR). Real-time quantitative PCR is presently preferred. RNA analysis can be performed on total cellular RNA or poly(A)+ mRNA. The preferred method of RNA analysis of the present invention is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of SGLT2 can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to SGLT2 can be identified and obtained from a variety of sources, such as the MSRS catalog of antibodies (Aerie Corporation, Birmingham, Mich.), or can be prepared via conventional monoclonal or polyclonal antibody generation methods well known in the art.

Example 11

Design of Phenotypic Assays for the Use of SGLT2 Inhibitors

Phenotypic Assays

Once SGLT2 inhibitors have been identified by the methods disclosed herein, the compounds are further investigated in one or more phenotypic assays, each having measurable endpoints predictive of efficacy in the treatment of a particular disease state or condition. Phenotypic assays, kits and reagents for their use are well known to those skilled in the art and are herein used to investigate the role and/or association of SGLT2 in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with SGLT2 inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Analysis of the genotype of the cell (measurement of the expression of one or more of the genes of the cell) after treatment is also used as an indicator of the efficacy or potency of the SGLT2 inhibitors. Hallmark genes, or those genes suspected to be associated with a specific disease state, condition, or phenotype, are measured in both treated and untreated cells.

Example 12

RNA Isolation

Poly(A)+ mRNA isolation

Poly(A)+ mRNA was isolated according to Miura et al., (*Clin. Chem.*, 1996, 42, 1758-1764). Other methods for poly (A)+ mRNA isolation are routine in the art. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 604 of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Total RNA Isolation

Total RNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 µL cold PBS. 150 µL Buffer RLT was added to each well and the plate vigorously agitated for 20 seconds. 150 µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 1 minute. 500 µL of Buffer RW1 was added to each well of the RNEASY 96™ plate and incubated for 15 minutes and the vacuum was again applied for 1 minute. An additional 500 µL of Buffer RW1 was added to each well of the RNEASY 96™ plate and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 140 µL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-Time Quantitative PCR Analysis of SGLT2 mRNA Levels

Quantitation of SGLT2 mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from Invitrogen Corporation, (Carlsbad, Calif.). RT-PCR reactions were carried out by adding 20 μL PCR cocktail (2.5×PCR buffer minus MgCl$_2$, 6.6 mM MgCl$_2$, 375 μM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5× ROX dye) to 96-well plates containing 30 μL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RiboGreen™ are taught in Jones, L. J., et al, (Analytical Biochemistry, 1998, 265, 368-374).

In this assay, 170 μL of RiboGreen™ working reagent (RiboGreen™ reagent diluted 1:350 in 10 mM Tris-HCl, 1 mM EDTA, pH 7.5) is pipetted into a 96-well plate containing 30 μL purified, cellular RNA. The plate is read in a CytoFluor 4000 (PE Applied Biosystems) with excitation at 485 nm and emission at 530 nm.

Probes and primers to human SGLT2 were designed to hybridize to a human SGLT2 sequence, using published sequence information (GenBank accession number NM_003041.1, incorporated herein as SEQ ID NO: 4). For human SGLT2 the PCR primers were:

```
                                      (SEQ ID NO: 5)
    forward primer: TCGGCGTGCCCAGCT (SEQ ID NO: 6)
    reverse primer: AGAACAGCACAATGGCGAAGT
``` and the PCR probe was:

```
FAM-TCCTCTGCGGCGTGCACTACCTC-TAMRA  (SEQ ID NO: 7)
``` where FAM is the fluorescent dye and TAMRA is the quencher dye. For human GAPDH the PCR primers were:

```
                                      (SEQ ID NO: 8)
    forward primer: GAAGGTGAAGGTCGGAGTC (SEQ ID NO: 9)
    reverse primer: GAAGATGGTGATGGGATTTC
``` and the PCR probe was:

```
                                      (SEQ ID NO: 10)
    5' JOE-CAAGCTTCCCGTTCTCAGCC-TAMRA 3'
``` where JOE is the fluorescent reporter dye and TAMRA is the quencher dye.

Probes and primers to mouse SGLT2 were designed to hybridize to a mouse SGLT2 sequence, using published sequence information (the concatenation of the sequences with the GenBank accession numbers: AJ292928, AW106808, AI789450, AW046901, the complement of AI647605, the complement of AW107250, and the complement of AI1788744, incorporated herein as SEQ ID NO: 11). For mouse SGLT2 the PCR primers were:

```
                                         (SEQ ID NO: 12)
     forward primer: TGTTGGACCCTCACAAAGAGTAAG (SEQ ID NO: 13)
     reverse primer: GCTGTATTCTTGCCCTGTTCCT
``` and the PCR probe was:

```
                                         (SEQ ID NO: 14)
     FAM-TTCTGGGATCCACTCCAAGCTGCTCA-TAMRA
``` where FAM is the fluorescent reporter dye and TAMRA is the quencher dye. For mouse GAPDH the PCR primers were:

```
                                         (SEQ ID NO: 15)
     forward primer: GGCAAATTCAACGGCACAGT (SEQ ID NO: 16)
     reverse primer: GGGTCTCGCTCCTGGAAGAT
``` and the PCR probe was:

```
                                         (SEQ ID NO: 17)
     5' JOE-AAGGCCGAGAATGGGAAGCTTGTCATC-TAMRA 3'
``` where JOE is the fluorescent reporter dye and TAMRA is the quencher dye.

Example 14

Northern Blot Analysis of SGLT2 mRNA Levels

Eighteen hours after antisense treatment, cell monolayers were washed twice with cold PBS and lysed in 1 mL RNA-ZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human SGLT2, a human SGLT2 specific probe was prepared by PCR using the forward primer TCGGCGTGCCCAGCT (SEQ ID NO: 5) and the reverse primer AGAACAGCACAATGGCGAAGT (SEQ ID NO: 6). To normalize for variations in loading and transfer efficiency membranes were stripped and probed for human glyceraldehyde-3-phosphate dehydrogenase (GAPDH) RNA (Clontech, Palo Alto, Calif.).

To detect mouse SGLT2, a mouse SGLT2 specific probe was prepared by PCR using the forward primer TGTTGGACCCTCACAAAGAGTAAG (SEQ ID NO: 12) and the reverse primer GCTGTATTCTTGCCCTGTTCCT (SEQ ID NO: 13). To normalize for variations in loading and transfer efficiency membranes were stripped and probed for mouse glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Antisense Inhibition of Human SGLT2 Expression by Chimeric Phosphorothioate Oligonucleotides Having 2'-MOE Wings and a Deoxy Gap In accordance with the present invention, a series of antisense compounds was designed to target different regions of the human SGLT2 RNA, using published sequences (GenBank accession number NM_003041.1, incorporated herein as SEQ ID NO: 4). The compounds are shown in Table 1. "Target site" indicates the first (5'-most) nucleotide number on the particular target sequence to which the compound binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE)nucleotides. The internucleoside (backbone) linkages are phosphorothioate (P=S) throughout the oligonucleotide. All cytidine residues are 5-methylcytidines. The compounds were analyzed for their effect on human SGLT2 mRNA levels by quantitative real-time PCR as described in other examples herein. HK-2 cells were treated with 500 nM of antisense oligonucleotide mixed with 15 µg/mL LIPOFECTIN. Data are averages from three experiments in which HK-2 cells were treated with the antisense oligonucleotides of the present invention. If present, "N.D." indicates "no data".

TABLE 1

Inhibition of human SGLT2 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 337873 | Start Codon | 4 | 1 | tctcccaggatctgccccc | 17 | 18 |
| 337874 | Start Codon | 4 | 15 | gtgtgctcctccattctccc | 41 | 19 |
| 337875 | Coding | 4 | 42 | cccatctctggtgccgagcc | 33 | 20 |
| 337876 | Coding | 4 | 70 | aggattgtcaatcagggcct | 49 | 21 |

TABLE 1-continued

Inhibition of human SGLT2 mRNA levels by chimeric
phosphorothioate oligonucleotides
having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 337877 | Coding | 4 | 95 | atgcagcaatgactaggatg | 45 | 22 |
| 337878 | Coding | 4 | 124 | caagccaacgccaatgacca | 54 | 23 |
| 337879 | Coding | 4 | 150 | cctctgttggttctgcacat | 26 | 24 |
| 337880 | Coding | 4 | 182 | tgcgtcctgccaggaagtag | 25 | 25 |
| 337881 | Coding | 4 | 204 | ccaaccggccaccacaccat | 45 | 26 |
| 337882 | Coding | 4 | 262 | agtccctgccaggcccacaa | 43 | 27 |
| 337883 | Coding | 4 | 291 | ccagcaacagccaagccact | 37 | 28 |
| 337884 | Coding | 4 | 354 | aggtacacgggtgcaaacag | 48 | 29 |
| 337885 | Coding | 4 | 384 | tactgtggcatcgtgatgac | 28 | 30 |
| 337886 | Coding | 4 | 426 | aggtagaggcggatgcggcg | 24 | 31 |
| 337887 | Coding | 4 | 442 | aagggagagcacagacaggt | 50 | 32 |
| 337888 | Coding | 4 | 474 | tccactgagatcttggtgaa | 41 | 33 |
| 337889 | Coding | 4 | 501 | tggatgaatacagctccgga | 49 | 34 |
| 337890 | Coding | 4 | 529 | ggcatagatgttccagccca | 36 | 35 |
| 337891 | Coding | 4 | 560 | tcatggtgatgcccagaagc | 23 | 36 |
| 337892 | Coding | 4 | 577 | tcctgtcaccgtgtaaatca | 39 | 37 |
| 337893 | Coding | 4 | 600 | gtgtacatcagcgcggccag | 33 | 38 |
| 337894 | Coding | 4 | 624 | atgacgaaggtctgtaccgt | 41 | 39 |
| 337895 | Coding | 4 | 651 | cccatgaggatgcaggcgcc | 55 | 40 |
| 337896 | Coding | 4 | 694 | gtcgaagagacccgaatacc | 30 | 41 |
| 337897 | Coding | 4 | 716 | aagtcgctgctcccaggtat | 0 | 42 |
| 337898 | Coding | 4 | 772 | tcgatagcagaagctggaga | 47 | 43 |
| 337899 | Coding | 4 | 849 | agtccgaggagcagcgcggg | 5 | 44 |
| 337900 | Coding | 4 | 884 | ggtcgctgcaccagtaccag | 29 | 45 |
| 337901 | Coding | 4 | 909 | gccaggcagcgctgcacgat | 22 | 46 |
| 337902 | Coding | 4 | 944 | tgcagcccgccttgatgtgg | 67 | 47 |
| 337903 | Coding | 4 | 954 | ccacacaggatgcagcccgc | 37 | 48 |
| 337904 | Coding | 4 | 991 | catgaccatgagaaacatgg | 43 | 49 |
| 337905 | Coding | 4 | 1006 | gctgatcatgcctggcatga | 54 | 50 |
| 337906 | Coding | 4 | 1033 | cgccacctcgtctgggtaca | 45 | 51 |
| 337907 | Coding | 4 | 1051 | cacctcaggcaccacgcacg | 54 | 52 |
| 337908 | Coding | 4 | 1073 | ccgtgccgcacacgcgcctg | 34 | 53 |
| 337909 | Coding | 4 | 1100 | ggtaggcgatgttggagcag | 30 | 54 |
| 337910 | Coding | 4 | 1122 | atgagcttcacgacgagccg | 48 | 55 |
| 337911 | Coding | 4 | 1151 | ccagcatgagtccgcgcaga | 50 | 56 |
| 337912 | Coding | 4 | 1180 | cgaggacatgagcgcggcca | 71 | 57 |

TABLE 1-continued

Inhibition of human SGLT2 mRNA levels by chimeric
phosphorothioate oligonucleotides
having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 337913 | Coding | 4 | 1211 | gcgtgctgctgctgttgaag | 37 | 58 |
| 337914 | Coding | 4 | 1232 | tgtagatgtccatggtgaag | 39 | 59 |
| 337915 | Coding | 4 | 1272 | agcagcagctcgcggtcgcc | 21 | 60 |
| 337916 | Coding | 4 | 1292 | ccacccagagccgtcccacc | 47 | 61 |
| 337917 | Coding | 4 | 1319 | aggccaccgacactaccacg | 38 | 62 |
| 337918 | Coding | 4 | 1360 | gaagagctgcccgccctgtg | 38 | 63 |
| 337919 | Coding | 4 | 1372 | ctggatgtaatcgaagagct | 45 | 64 |
| 337920 | Coding | 4 | 1415 | cgaagacggcggacacgggc | 3 | 65 |
| 337921 | Coding | 4 | 1433 | gcacgaagagcgccagcacg | 32 | 66 |
| 337922 | Coding | 4 | 1453 | gccctgctcattaacgcgcg | 34 | 67 |
| 337923 | Coding | 4 | 1479 | aggcccccgatgagtcccca | 48 | 68 |
| 337924 | Coding | 4 | 1497 | cgtgccaggcccatcagcag | 37 | 69 |
| 337925 | Coding | 4 | 1526 | ccgagccgaaggagaactcg | 47 | 70 |
| 337926 | Coding | 4 | 1544 | agggctgcacacagctgccc | 0 | 71 |
| 337927 | Coding | 4 | 1570 | gccgcagaggaaagctgggc | 15 | 72 |
| 337928 | Coding | 4 | 1595 | caatggcgaagtagaggtag | 37 | 73 |
| 337929 | Coding | 4 | 1615 | gccagagcagaagaacagca | 41 | 74 |
| 337930 | Coding | 4 | 1641 | cacagggagaccgtgagggt | 11 | 75 |
| 337931 | Coding | 4 | 1677 | aggcggtggaggtgctttct | 29 | 76 |
| 337932 | Coding | 4 | 1706 | cctccttgctatgccggaga | 47 | 77 |
| 337933 | Coding | 4 | 1729 | atcagcatccaggtcctccc | 0 | 78 |
| 337934 | Coding | 4 | 1763 | cattctgtacagggagtgag | 50 | 79 |
| 337935 | Coding | 4 | 1788 | atctccatggcactctctgg | 58 | 80 |
| 337936 | Coding | 4 | 1835 | gcaggcactggcggaagagg | 29 | 81 |
| 337937 | Coding | 4 | 1861 | acctctgctcattccacaaa | 56 | 82 |
| 337938 | Coding | 4 | 1881 | ggcggaggactgcccacccc | 22 | 83 |
| 337939 | Coding | 4 | 1917 | cgcctggctgctgccgctgc | 11 | 84 |
| 337940 | Coding | 4 | 1939 | gtcctcgctgatgtcctcca | 40 | 85 |
| 337941 | Coding | 4 | 1972 | ggcattgaggttgaccacac | 2 | 86 |
| 337942 | Coding | 4 | 2003 | agaggaacacggccactgcc | 8 | 87 |
| 337943 | Coding | 4 | 2014 | atagaagccccagaggaaca | 39 | 88 |
| 337944 | Stop Codon | 4 | 2025 | tggtcttaggcatagaagcc | 28 | 89 |
| 337945 | 3'UTR | 4 | 2048 | tggcttatggtgtccaacgc | 35 | 90 |
| 337946 | 3'UTR | 4 | 2072 | tcaccccacttcctgtgag | 42 | 91 |
| 337947 | 3'UTR | 4 | 2120 | tctcaccccactgcccttc | 38 | 92 |
| 337948 | 3'UTR | 4 | 2158 | caggcagaggaaggccggga | 38 | 93 |

TABLE 1-continued

Inhibition of human SGLT2 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 337949 | 3'UTR | 4 | 2197 | cctcatgggaagtgactgcc | 37 | 94 |
| 337950 | 3'UTR | 4 | 2230 | ttccttagggcaactgcagc | 34 | 95 |

As shown in Table 1, SEQ ID NOs 19, 20, 21, 22, 23, 26, 27, 28, 29, 32, 33, 34, 35, 37, 38, 39, 40, 41, 43, 47, 48, 49, 50, 51, 52, 53, 54, 55, 56, 57, 58, 59, 61, 62, 63, 64, 66, 67, 68, 69, 70, 73, 74, 77, 79, 80, 82, 85, 88, 90, 91, 92, 93, 94 and 95 demonstrated at least 30% inhibition of human SGLT2 expression in this assay. The target regions to which these sequences are complementary are herein referred to as "suitable target segments" and are therefore suitable for targeting by compounds of the present invention. These target segments are shown in Table 3. These sequences are shown to contain thymine (T) but one of skill in the art will appreciate that thymine (T) is generally replaced by uracil (U) in RNA sequences. The sequences represent the reverse complement of the suitable antisense compounds shown in Table 1. "Target site" indicates the first (5'-most) nucleotide number on the particular target nucleic acid to which the oligonucleotide binds. Also shown in Table 3 is the species in which each of the suitable target segments was found.

Example 16

Antisense Inhibition of Mouse SGLT2 Expression by Chimeric Phosphorothioate Oligonucleotides Having 2'-MOE Wings and a Deoxy Gap In accordance with the present invention, a second series of antisense compounds was designed to target different regions of the mouse SGLT2 RNA, using published sequences (the concatenation of the sequences with the GenBank accession numbers: AJ292928, AW106808, AI789450, AW046901, the complement of AI647605, the complement of AW107250, and the complement of AI788744, incorporated herein as SEQ ID NO: 11; GenBank accession number AJ292928.1, incorporated herein as SEQ ID NO: 96; and GenBank accession number AW045170.1, incorporated herein as SEQ ID NO: 97). The compounds are shown in Table 2. "Target site" indicates the first (5'-most) nucleotide number on the particular target nucleic acid to which the compound binds. All compounds in Table 2 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide. All cytidine residues are 5-methylcytidines. The compounds were analyzed for their effect on mouse SGLT2 mRNA levels by quantitative real-time PCR as described in other examples herein. Data are averages from three experiments in which b.END cells were treated with 100 nM of the antisense oligonucleotides of the present invention. The positive control for each datapoint is identified in the table by sequence ID number. If present, "N.D." indicates "no data".

TABLE 2

Inhibition of mouse SGLT2 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 145725 | Coding | 11 | 27 | tgctccccaagttcagagcc | 16 | 98 | 1 |
| 145726 | Coding | 11 | 39 | atcaggaccttctgctcccc | 30 | 99 | 1 |
| 145727 | Coding | 11 | 50 | caggattatcaatcaggacc | 15 | 100 | 1 |
| 145728 | Coding | 11 | 62 | ccagaatgtcagcaggatta | 9 | 101 | 1 |
| 145729 | Coding | 11 | 93 | ccaatgaccagcaggaaata | 15 | 102 | 1 |
| 145730 | Coding | 11 | 117 | ctgaacatagaccacaagcc | 0 | 103 | 1 |
| 145731 | Coding | 11 | 127 | tctattggttctgaacatag | 9 | 104 | 1 |
| 145732 | Coding | 11 | 138 | ccaactgtgcctctattggt | 43 | 105 | 1 |
| 145733 | Coding | 11 | 148 | gaagtagccaccaactgtgc | 16 | 106 | 1 |
| 145734 | Coding | 11 | 189 | gaggctccaaccggccacca | 43 | 107 | 1 |
| 145735 | Coding | 11 | 213 | ctgccgatgttgctggcgaa | 2 | 108 | 1 |

TABLE 2-continued

Inhibition of mouse SGLT2 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 145736 | Coding | 11 | 230 | ggcccacaaaatgaccgctg | 44 | 109 | 1 |
| 145737 | Coding | 11 | 261 | gccaagccacttgctgcacc | 29 | 110 | 1 |
| 145738 | Coding | 11 | 294 | acgaagagcgcattccactc | 7 | 111 | 1 |
| 145739 | Coding | 11 | 299 | gcaccacgaagagcgcattc | 0 | 112 | 1 |
| 145740 | Coding | 11 | 375 | cgcttgcggaggtactgagg | 0 | 113 | 1 |
| 145741 | Coding | 11 | 420 | agcgagagcacggacaggta | 0 | 114 | 1 |
| 145742 | Coding | 11 | 462 | gagaacatatccaccgagat | 5 | 115 | 1 |
| 145743 | Coding | 11 | 490 | cagggcctgttgaatgaata | 0 | 116 | 1 |
| 145744 | Coding | 11 | 550 | cacagtataaatcatggtga | 35 | 117 | 1 |
| 145745 | Coding | 11 | 581 | ctgtgtacatcagtgccgcc | 18 | 118 | 1 |
| 145746 | Coding | 11 | 592 | ctgcacagtgtctgtgtaca | 7 | 119 | 1 |
| 145747 | Coding | 11 | 605 | gaatgacgaaggtctgcaca | 14 | 120 | 1 |
| 145748 | Coding | 11 | 616 | ggccccggcaagaatgacga | 25 | 121 | 1 |
| 145749 | Coding | 11 | 659 | agtacccgcccacttcatgg | 0 | 122 | 1 |
| 145750 | Coding | 11 | 706 | acccgtcagtgaagtcattg | 18 | 123 | 1 |
| 145751 | Coding | 11 | 784 | gtcacgcagcaggtgatagg | 24 | 124 | 1 |
| 145752 | Coding | 11 | 795 | cctgtcacagggtcacgcag | 40 | 125 | 1 |
| 145753 | Coding | 11 | 840 | gagacaatggtaagccccag | 20 | 126 | 1 |
| 145754 | Coding | 11 | 902 | tcagattctttccagccagg | 12 | 127 | 1 |
| 145755 | Coding | 11 | 912 | ttgatgtgagtcagattctt | 13 | 128 | 1 |
| 145756 | Coding | 11 | 998 | ggtagagaatgcggctgatc | 8 | 129 | 1 |
| 145757 | Coding | 11 | 1039 | ccgcttacacacctcaggta | 32 | 130 | 1 |
| 145758 | Coding | 11 | 1050 | gtgccacacacccgcttaca | 39 | 131 | 1 |
| 145759 | Coding | 11 | 1068 | ttagagcagcccacctcagt | 28 | 132 | 1 |
| 145760 | Coding | 11 | 1081 | tgggtaggcgatgttagagc | 15 | 133 | 1 |
| 145761 | Coding | 11 | 1113 | agaccattgggcatgagctt | 2 | 134 | 1 |
| 145762 | Coding | 11 | 1128 | agcatgagtccgcgcagacc | 0 | 135 | 1 |
| 145763 | Coding | 11 | 1142 | ccagcatgactgccagcatg | 22 | 136 | 1 |
| 145764 | Coding | 11 | 1177 | gttaaagatggatgccagag | 0 | 137 | 1 |
| 145765 | Coding | 11 | 1246 | cagctccttatcacctgcac | 55 | 138 | 1 |
| 145766 | Coding | 11 | 1320 | gctgcctgcaccactggcag | 44 | 139 | 1 |
| 145767 | Coding | 11 | 1393 | aaagaccgcagacacttgag | 0 | 140 | 1 |
| 145768 | Coding | 11 | 1403 | gtgcaagcacaaagaccgca | 6 | 141 | 1 |
| 145769 | Coding | 11 | 1475 | gagctaggcccatcagcagg | 55 | 142 | 1 |
| 145770 | Coding | 11 | 1485 | ggtatgagacgagctaggcc | 0 | 143 | 1 |
| 145771 | Coding | 11 | 1496 | agaagaactcgggtatgaga | 0 | 144 | 1 |

TABLE 2-continued

Inhibition of mouse SGLT2 mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO | CONTROL SEQ ID NO |
|---|---|---|---|---|---|---|---|
| 145772 | Coding | 11 | 1524 | gagggtcgcacacagctgcc | 8 | 145 | 1 |
| 145773 | Coding | 11 | 1563 | tagaggtagtgtacccgaca | 0 | 146 | 1 |
| 145774 | Coding | 11 | 1682 | ccttgctgtgccggagactg | 40 | 147 | 1 |
| 145775 | Coding | 11 | 1707 | tcagcatccaggtcctcccg | 46 | 148 | 1 |
| 145776 | Coding | 11 | 1722 | ggaccttctaactcatcagc | 2 | 149 | 1 |
| 145777 | Coding | 11 | 1765 | cattgcacattcctggcccc | 23 | 150 | 1 |
| 145778 | Coding | 11 | 1839 | ttgctcatcccacagaacca | 15 | 151 | 1 |
| 145779 | Coding | 11 | 1851 | cctgacccactcttgctcat | 1 | 152 | 1 |
| 145780 | Coding | 11 | 1881 | gccacctcctcggtagtggg | 21 | 153 | 1 |
| 145781 | Coding | 11 | 1909 | gatgtcctccagccgcctgg | 0 | 154 | 1 |
| 145782 | Coding | 11 | 1921 | gggatcctcactgatgtcct | 25 | 155 | 1 |
| 145783 | Coding | 11 | 1953 | agggcattgaggttgactac | 11 | 156 | 1 |
| 145784 | Coding | 11 | 1992 | tagaagcccagaggaacac | 0 | 157 | 1 |
| 145785 | 3'UTR | 11 | 2164 | aatcaaatggactggacccc | 0 | 158 | 1 |
| 145786 | 3'UTR | 11 | 2174 | agtgacaaccaatcaaatgg | 10 | 159 | 1 |
| 145787 | 3'UTR | 11 | 2186 | catcttgtgggaagtgacaa | 14 | 160 | 1 |
| 145788 | 3'UTR | 11 | 2199 | accaattggccatcatcttg | 0 | 161 | 1 |
| 145789 | 3'UTR | 11 | 2237 | ggagggcagttttattttg | 20 | 162 | 1 |
| 145790 | exon:intron | 96 | 2123 | caatgtctcacccacaagcc | 4 | 163 | 1 |
| 145791 | intron | 96 | 2239 | ctaaatctaggtttctccct | 11 | 164 | 1 |
| 145792 | intron | 96 | 2291 | ttttgcacaatccagaaggt | 9 | 165 | 1 |
| 145793 | intron | 96 | 2407 | gaccttaaatataggctgct | 0 | 166 | 1 |
| 145794 | intron | 96 | 2477 | aacccaggccctaatcctag | 4 | 167 | 1 |
| 145795 | intron | 96 | 2551 | aggctgaagattaaccagcc | 8 | 168 | 1 |
| 145796 | intron | 96 | 2595 | ttggacttccttagcttcct | 9 | 169 | 1 |
| 145797 | exon:intron | 96 | 2647 | gaacatagactgggaaacag | 0 | 170 | 1 |
| 145798 | intron | 96 | 2797 | gaggctccaacctgggtggc | 12 | 171 | 1 |
| 145799 | intron | 97 | 133 | tccagcaaatgaacctgtgt | 0 | 172 | 1 |
| 145800 | intron | 97 | 284 | cacagcggaagtgcctgggc | 21 | 173 | 1 |
| 145801 | intron | 97 | 316 | tgtcctagtcctcacaccca | 12 | 174 | 1 |
| 145802 | intron | 97 | 338 | gggacagcatcctgagcagg | 25 | 175 | 1 |

As shown in Table 2, SEQ ID NOs 99, 105, 107, 109, 110, 117, 121, 124, 125, 126, 130, 131, 132, 136, 138, 139, 142, 147, 148, 150, 153, 155, 162, 173 and 175 demonstrated at least 20% inhibition of mouse SGLT2 expression in this experiment. Also suitable are SEQ ID NOs 105, 119 and 135. The target regions to which these sequences are complementary are herein referred to as "suitable target segments" and are therefore suitable for targeting by compounds of the present invention. These target segments are shown in Table 3. These sequences are shown to contain thymine (T) but one of skill in the art will appreciate that thymine (T) is generally replaced by uracil (U) in RNA sequences. The sequences represent the reverse complement of the preferred antisense compounds shown in Tables 1 and 2. "Target site" indicates the first (5'-most) nucleotide number on the particular target nucleic acid to which the oligonucleotide binds. Also shown in Table 3 is the species in which each of the suitable target segments was found.

TABLE 3

Sequence and position of preferred target segments identified in human and mouse SGLT2.

| SITE ID | TARGET SEQ ID NO | TARGET SITE | SEQUENCE | REV COMP OF SEQ ID | ACTIVE IN | SEQ ID NO |
|---|---|---|---|---|---|---|
| 253571 | 4 | 15 | gggagaatggaggagcacac | 19 | H. sapiens | 176 |
| 253572 | 4 | 42 | ggctcggcaccagagatggg | 20 | H. sapiens | 177 |
| 253573 | 4 | 70 | aggccctgattgacaatcct | 21 | H. sapiens | 178 |
| 253574 | 4 | 95 | catcctagtcattgctgcat | 22 | H. sapiens | 179 |
| 253575 | 4 | 124 | tggtcattggcgttggcttg | 23 | H. sapiens | 180 |
| 253578 | 4 | 204 | atggtgtggtggccggttgg | 26 | H. sapiens | 181 |
| 253579 | 4 | 262 | ttgtgggcctggcagggact | 27 | H. sapiens | 182 |
| 253580 | 4 | 291 | agtggcttggctgttgctgg | 28 | H. sapiens | 183 |
| 253581 | 4 | 354 | ctgtttgcacccgtgtacct | 29 | H. sapiens | 184 |
| 253584 | 4 | 442 | acctgtctgtgctctcccctt | 32 | H. sapiens | 185 |
| 253585 | 4 | 474 | ttcaccaagatctcagtgga | 33 | H. sapiens | 186 |
| 253586 | 4 | 501 | tccggagctgtattcatcca | 34 | H. sapiens | 187 |
| 253587 | 4 | 529 | tgggctggaacatctatgcc | 35 | H. sapiens | 188 |
| 253589 | 4 | 577 | tgatttacacggtgacagga | 37 | H. sapiens | 189 |
| 253590 | 4 | 600 | ctggccgcgctgatgtacac | 38 | H. sapiens | 190 |
| 253591 | 4 | 624 | acggtacagaccttcgtcat | 39 | H. sapiens | 191 |
| 253592 | 4 | 651 | ggcgcctgcatcctcatggg | 40 | H. sapiens | 192 |
| 253593 | 4 | 694 | ggtattcgggtctcttcgac | 41 | H. sapiens | 193 |
| 253595 | 4 | 772 | tctccagcttctgctatcga | 43 | H. sapiens | 194 |
| 253599 | 4 | 944 | ccacatcaaggcgggctgca | 47 | H. sapiens | 195 |
| 253600 | 4 | 954 | gcgggctgcatcctgtgtgg | 48 | H. sapiens | 196 |
| 253601 | 4 | 991 | ccatgtttctcatggtcatg | 49 | H. sapiens | 197 |
| 253602 | 4 | 1006 | tcatgccaggcatgatcagc | 50 | H. sapiens | 198 |
| 253603 | 4 | 1033 | tgtacccagacgaggtggcg | 51 | H. sapiens | 199 |
| 253604 | 4 | 1051 | cgtgcgtggtgcctgaggtg | 52 | H. sapiens | 200 |
| 253605 | 4 | 1073 | caggcgcgtgtgcggcacgg | 53 | H. sapiens | 201 |
| 253606 | 4 | 1100 | ctgctccaacatcgcctacc | 54 | H. sapiens | 202 |
| 253607 | 4 | 1122 | cggctcgtcgtgaagctcat | 55 | H. sapiens | 203 |
| 253608 | 4 | 1151 | tctgcgcggactcatgctgg | 56 | H. sapiens | 204 |
| 253609 | 4 | 1180 | tggccgcgctcatgtcctcg | 57 | H. sapiens | 205 |
| 253610 | 4 | 1211 | cttcaacagcagcagcacgc | 58 | H. sapiens | 206 |

TABLE 3-continued

Sequence and position of preferred target segments identified in human and mouse SGLT2.

| SITE ID | TARGET SEQ ID NO | TARGET SITE | SEQUENCE | REV COMP OF SEQ ID | ACTIVE IN | SEQ ID NO |
|---|---|---|---|---|---|---|
| 253611 | 4 | 1232 | cttcaccatggacatctaca | 59 | H. sapiens | 207 |
| 253613 | 4 | 1292 | ggtgggacggctctgggtgg | 61 | H. sapiens | 208 |
| 253614 | 4 | 1319 | cgtggtagtgtcggtggcct | 62 | H. sapiens | 209 |
| 253615 | 4 | 1360 | cacagggcgggcagctcttc | 63 | H. sapiens | 210 |
| 253616 | 4 | 1372 | agctcttcgattacatccag | 64 | H. sapiens | 211 |
| 253618 | 4 | 1433 | cgtgctggcgctcttcgtgc | 66 | H. sapiens | 212 |
| 253619 | 4 | 1453 | cgcgcgttaatgagcagggc | 67 | H. sapiens | 213 |
| 253620 | 4 | 1479 | tggggactcatcgggggcct | 68 | H. sapiens | 214 |
| 253621 | 4 | 1497 | ctgctgatgggcctggcacg | 69 | H. sapiens | 215 |
| 253622 | 4 | 1526 | cgagttctccttcggctcgg | 70 | H. sapiens | 216 |
| 253625 | 4 | 1595 | ctacctctacttcgccattg | 73 | H. sapiens | 217 |
| 253626 | 4 | 1615 | tgctgttcttctgctctggc | 74 | H. sapiens | 218 |
| 253629 | 4 | 1706 | tctccggcatagcaaggagg | 77 | H. sapiens | 219 |
| 253631 | 4 | 1763 | ctcactccctgtacagaatg | 79 | H. sapiens | 220 |
| 253632 | 4 | 1788 | ccagagagtgccatggagat | 80 | H. sapiens | 221 |
| 253634 | 4 | 1861 | tttgtggaatgagcagaggt | 82 | H. sapiens | 222 |
| 253637 | 4 | 1939 | tggaggacatcagcgaggac | 85 | H. sapiens | 223 |
| 253640 | 4 | 2014 | tgttcctctggggcttctat | 88 | H. sapiens | 224 |
| 253642 | 4 | 2048 | gcgttggacaccataagcca | 90 | H. sapiens | 225 |
| 253643 | 4 | 2072 | ctcacaggaagtgggggtga | 91 | H. sapiens | 226 |
| 253644 | 4 | 2120 | gaaggggcagtggggtgaga | 92 | H. sapiens | 227 |
| 253645 | 4 | 2158 | tcccggccttcctctgcctg | 93 | H. sapiens | 228 |
| 253646 | 4 | 2197 | ggcagtcacttcccatgagg | 94 | H. sapiens | 229 |
| 253647 | 4 | 2230 | gctgcagttgccctaaggaa | 95 | H. sapiens | 230 |
| 58683 | 11 | 39 | ggggagcagaaggtcctgat | 99 | M. musculus | 231 |
| 58689 | 11 | 138 | accaatagaggcacagttgg | 105 | M. musculus | 232 |
| 58691 | 11 | 189 | tggtggccggttggagcctc | 107 | M. musculus | 233 |
| 58693 | 11 | 230 | cagcggtcattttgtgggcc | 109 | M. musculus | 234 |
| 58694 | 11 | 261 | ggtgcagcaagtggcttggc | 110 | M. musculus | 235 |
| 58701 | 11 | 550 | tcaccatgatttatactgtg | 117 | M. musculus | 236 |
| 58705 | 11 | 616 | tcgtcattcttgccggggcc | 121 | M. musculus | 237 |
| 58708 | 11 | 784 | cctatcacctgctgcgtgac | 124 | M. musculus | 238 |
| 58709 | 11 | 795 | ctgcgtgaccctgtgacagg | 125 | M. musculus | 239 |
| 58710 | 11 | 840 | ctggggcttaccattgtctc | 126 | M. musculus | 240 |
| 58714 | 11 | 1039 | tacctgaggtgtgtaagcgg | 130 | M. musculus | 241 |
| 58715 | 11 | 1050 | tgtaagcgggtgtgtggcac | 131 | M. musculus | 242 |

TABLE 3-continued

Sequence and position of preferred target segments identified in human and mouse SGLT2.

| SITE ID | TARGET SEQ ID NO | TARGET SITE | SEQUENCE | REV COMP OF SEQ ID | ACTIVE IN | SEQ ID NO |
|---|---|---|---|---|---|---|
| 58716 | 11 | 1068 | actgaggtgggctgctctaa | 132 | M. musculus | 243 |
| 58720 | 11 | 1142 | catgctggcagtcatgctgg | 136 | M. musculus | 244 |
| 58722 | 11 | 1246 | gtgcaggtgataaggagctg | 138 | M. musculus | 245 |
| 58723 | 11 | 1320 | ctgccagtggtgcaggcagc | 139 | M. musculus | 246 |
| 58726 | 11 | 1475 | cctgctgatgggcctagctc | 142 | M. musculus | 247 |
| 58731 | 11 | 1682 | cagtctccggcacagcaagg | 147 | M. musculus | 248 |
| 58732 | 11 | 1707 | cgggaggacctggatgctga | 148 | M. musculus | 249 |
| 58734 | 11 | 1765 | ggggccaggaatgtgcaatg | 150 | M. musculus | 250 |
| 58737 | 11 | 1881 | cccactaccgaggaggtggc | 153 | M. musculus | 251 |
| 58739 | 11 | 1921 | aggacatcagtgaggatccc | 155 | M. musculus | 252 |
| 58746 | 11 | 2237 | caaaaataaaactgccctcc | 162 | M. musculus | 253 |
| 58757 | 97 | 284 | gcccaggcacttccgctgtg | 173 | M. musculus | 254 |
| 58759 | 97 | 338 | cctgctcaggatgctgtccc | 175 | M. musculus | 255 |

As these "suitable target segments" have been found by experimentation to be open to, and accessible for, hybridization with the antisense compounds of the present invention, one of skill in the art will recognize or be able to ascertain, using no more than routine experimentation, further embodiments of the invention that encompass other compounds that specifically hybridize to these suitable target segments and consequently inhibit the expression of SGLT2.

According to the present invention, antisense compounds include antisense oligomeric compounds, antisense oligonucleotides, ribozymes, external guide sequence (EGS) oligonucleotides, alternate splicers, and other short oligomeric compounds which hybridize to at least a portion of the target nucleic acid.

Example 17

Western Blot Analysis of SGLT2 Protein Levels

Western blot analysis (immunoblot analysis) is carried out using standard methods. Cells are harvested 16-20 h after oligonucleotide treatment, washed once with PBS, suspended in Laemmli buffer (100 µl/well), boiled for 5 minutes and loaded on a 16% SDS-PAGE gel. Gels are run for 1.5 hours at 150 V, and transferred to membrane for western blotting. Appropriate primary antibody directed to SGLT2 is used, with a radiolabeled or fluorescently labeled secondary antibody directed against the primary antibody species. Bands are visualized using a PHOSPHORIMAGER™ (Molecular Dynamics, Sunnyvale Calif.).

Example 18

Design of Chemically Modified Antisense Compounds Targeting SGLT2

A series of chemically modified antisense compounds were designed using the sequence of ISIS 145733 (SEQ ID NO: 106), ISIS 145742 (SEQ ID NO: 265) or ISIS 145746 (SEQ ID NO: 266). Modifications were made to the internucleoside linkages such that the oligonucleotides consisted of either full phosphorothioate backbones or mixed phosphorothioate and phosphodiester backbones (mixed backbone compounds). Modified antisense compounds also contained sugar moiety substitutions at the 2' position, comprising a 2'-methoxyethyl (2'-MOE) or a 2'-O-dimethylaminoethoxyethyl (2'-DMAEOE). Further modifications included nucleobase substitutions, wherein the unmodified cytosine nucleobase was used in place of the modified 5-methylcytosine at one position in the antisense compound. The compounds are shown in Table 4.

ISIS 145733 (SEQ ID NO: 106), ISIS 145742 (SEQ ID NO: 265) and ISIS 145746 (SEQ ID NO: 266) are chimeric oligonucleotides having 2'-MOE wings and a deoxy gap with phosphorothioate linkages throughout the oligonucleotide. ISIS 257016 (SEQ ID NO: 106), ISIS 341699 (SEQ ID NO: 265) and ISIS 351642 (SEQ ID NO: 266) are chimeric oligonucleotides having 2'-MOE wings and a deoxy gap, with phosphodiester linkages in the wings and phosphorothioate linkages in the gap. ISIS 351641 (SEQ ID NO: 106), ISIS 360886 (SEQ ID NO: 106) and ISIS 360887 (SEQ ID NO: 106) are chimeric oligonucleotides having 2'-MOE wings and a deoxy gap, with phosphorothioate linkages in the gap and phosphodiester linkages in the wings, except for one phosphorothioate linkage in the wing(s) at either the extreme 5' end (ISIS 360886), the extreme 3' end (ISIS 360887) or both of the extreme 5' and 3' ends (ISIS 351641).

ISIS 323294 (SEQ ID NO: 106) consists of 2'-MOE nucleotides at positions 1, 2, 3, 4, 17 and 19, 2'-DMAEOE nucleotides at positions 5, 16, 18 and 20 and 2'-deoxynucleotides at positions 6 through 15, with phosphorothioate linkages throughout the oligonucleotide. ISIS 323295 (SEQ ID NO: 106) consists of 2'-MOE nucleotides at positions 1, 2, 3, 4, 17 and 19, 2'-DMAEOE nucleotides at positions 5, 16, 18 and 20 and 2'-deoxynucleotides at positions 6 through 15, wherein the first and last 4 internucleoside linkages are phosphodiester and the central internucleoside linkages are phosphorothioate.

The nucleotides in the 3' most positions in ISIS 251017 and 257018 are cytosine residues (indicated by an asterisk in Table 4). All other cytosine residues of the oligonucleotides listed above are 5-methylcytosines. The compounds are shown in Table 4. Phosphodiester (P═O) internucleoside linkages are indicated by an "o" between nucleotide positions. Phosphorothioate (P═S) internucleoside linkages are indicated by an "s" between nucleotide positions. 2'-MOE nucleotides are underscored and 2'-DMAEOE nucleotides are emboldened. All compounds in Table 4 target the coding region of murine SGLT2 (provided herein as SEQ ID NO: 11).

TABLE 4

Chemical modifications of antisense compounds targeting SGLT2

| ISIS # | Sequence | SEQ ID NO |
|---|---|---|
| 145733 | GsAsAsGsTsAsGsCsCsAsCsCsAsAsCsTsGsTsGsC | 106 |
| 257016 | GoAoAoGoTsAsGsCsCsAsCsCsAsAsCsToGoToGoC | 106 |
| 257017 | GsAsAsGsTsAsGsCsCsAsCsCsAsAsCsTsGsTsGsC* | 106 |
| 257018 | GoAoAoGoTsAsGsCsCsAsCsCsAsAsCsToGoToGoC* | 106 |
| 145742 | GsAsGsAsAsCsAsTsAsTsCsCsAsCsCsGsAsGsAsT | 265 |
| 341699 | GoAoGoAoAsCsAsTsAsTsCsCsAsCsCsGoAoGoAoT | 265 |
| 145746 | CsTsGsCsAsCsAsGsTsGsTsCsTsGsTsGsTsAsCsA | 266 |
| 351642 | CoToGoCoAsCsAsGsTsGsTsCsTsGsTsGoToAoCoA | 266 |
| 351641 | GsAoAoGoTsAsGsCsCsAsCsCsAsAsCsToGoToGsC | 106 |
| 360886 | GsAoAoGoTsAsGsCsCsAsCsCsAsAsCsToGoToGoC | 106 |
| 360887 | GoAoAoGoTsAsGsCsCsAsCsCsAsAsCsToGoToGsC | 106 |
| 323294 | GsAsAsGsTsAsGsCsCsAsCsCsAsAsCsTsGsTsGsC | 106 |
| 323295 | GoAoAoGoTsAsGsCsCsAsCsCsAsAsCsToGoToGoC | 106 |

Example 19

Effects of Antisense Inhibition of SGLT2 in Mice: Comparison of Various Chemistries In accordance with the present invention, SGLT2 antisense compounds described in Example 18 were investigated for their activity in vivo. ISIS 29837 (TCGATCTCCTTTTATGCCCG, SEQ ID NO: 256) served as a control compound and is a chimeric oligonucleotide ("gapmer") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P═S) throughout the oligonucleotide. All cytidine residues are 5-methylcytidines.

Male 6-week old Balb/c mice (Charles River Laboratories, Wilmington, Mass.) were given intraperitoneal injections of ISIS 145733, ISIS 257016, ISIS 323294, ISIS 323295 or ISIS 29837 at a dose of 25 mg/kg twice per week for two weeks. Saline-injected animals also served as a control. Each treatment group contained four animals. The mice were sacrificed 2 days following administration of the fourth and final dose of oligonucleotide or saline.

Mice were evaluated for SGLT2 levels in kidney. Target levels were determined by quantitative real-time PCR as described by other examples herein. PCR results were normalized to the ubiquitously expressed mouse cyclophilin A gene.

Probes and primers to mouse SGLT2 were designed to hybridize to a mouse SGLT2 sequence, using published sequence information (incorporated herein as SEQ ID NO: 11). For mouse SGLT2 the PCR primers were:

(SEQ ID NO: 257)
forward primer: CTCGTCTCATACCCGAGTTCTTCT (SEQ ID NO: 258)
reverse primer: AATGATGGCGAAATAGAGGTAGTGTAC and the PCR probe was:

(SEQ ID NO: 259)
FAM-TGCGACCCTCAGCGTGCCC-TAMRA where FAM is the fluorescent dye and TAMRA is the quencher dye. For mouse cyclophilin A the PCR primers were:

(SEQ ID NO: 260)
forward primer: TCGCCGCTTGCTGCA (SEQ ID NO: 261)
reverse primer: ATCGGCCGTGATGTCGA and the PCR probe was:

(SEQ ID NO: 262)
5' JOE-CCATGGTCAACCCCACCGTGTTC-3' where JOE is the fluorescent reporter dye and TAMRA is the quencher dye.

The data are expressed as percent change ("−" indicates a decrease) relative to saline treated animals and are shown in Table 5.

TABLE 5

Antisense inhibition of SGLT2 mRNA expression in vivo by 25 mg/kg doses of antisense compounds
% change in SGLT2 expression relative to saline

| ISIS 145733 | ISIS 257016 | ISIS 323294 | ISIS 323295 | ISIS 29837 |
|---|---|---|---|---|
| −44 | −82 | −40 | −31 | −23 |

These data illustrate that antisense compounds of different chemistries inhibit the expression of SGLT2 mRNA in mouse kidney.

Mice were further evaluated for total body weight, liver weight and spleen weight. Significant changes in spleen, liver or body weight can indicate that a particular compound causes toxic effects. The data are expressed as percent change ("+" indicates an increase, "−" indicates a decrease) relative to saline control. The results are presented in Table 6.

TABLE 6

Effects of antisense compounds on total body weight, liver weight and spleen weight in mice

| | Weight as % change relative to saline control | | | | |
|---|---|---|---|---|---|
| | 145733 | 257016 | 323294 | 323295 | 29837 |
| Total Body | 0 | 0 | −1 | −3 | 0 |
| Liver | +1 | +1 | +9 | +4 | +12 |
| Spleen | +4 | +1 | +19 | +8 | +1 |

All changes were within the margin of error of the experiment. No significant changes in body weight were observed during the treatment or at study termination. No significant changes in liver or spleen weights were observed.

Toxic effects of compounds administered in vivo can also be assessed by measuring the levels of enzymes and proteins associated with disease or injury of the liver or kidney. Elevations in the levels of the serum transaminases aspartate aminotransferase (AST) and alanine aminotransferase (ALT) are often indicators of liver disease or injury. Serum total bilirubin is an indicator of liver and biliary function, and albumin and blood urea nitrogen (BUN) are indicators of renal function. Glucose and triglyceride levels are sometimes altered due to toxicity of a treatment. Serum glucose also depends in part upon the activity of SGLT2.

In accordance with the present invention, the levels of ALT, AST, total bilirubin, albumin, BUN, glucose and triglyceride were measured in mice treated with the compounds of the invention. Serum was analyzed by LabCorp Testing Facility (San Diego, Calif.). The results are expressed as units measured and are shown in Table 7.

TABLE 7

Effects of antisense compounds targeting SGLT2 on liver and kidney function in mice

| Serum indicator | Normal Range | Treatment and units measured | | | | | |
|---|---|---|---|---|---|---|---|
| | | Saline | 145733 | 257016 | 323294 | 323295 | 29837 |
| BUN mg/dL | 15-40 | 27 | 29 | 33 | 29 | 30 | 30 |
| Albumin g/dL | 2.5-4.0 | 3 | 3 | 3 | 3 | 3 | 3 |
| Bilirubin mg/dL | 0.1-1.0 | 0.1 | 0.1 | 0.1 | 0.1 | 0.1 | 0.1 |
| AST IU/L | 30-300 | 124 | 83 | 129 | 174 | 89 | 114 |
| ALT IU/L | 30-200 | 33 | 26 | 47 | 61 | 32 | 31 |
| Triglycerides mg/dL | 25-100* | 179 | 154 | 157 | 160 | 209 | 198 |
| Glucose mg/dL | 80-150* | 242 | 270 | 222 | 284 | 271 | 235 |

*Triglyceride and glucose levels are routinely higher in the Balb/c strain of mice than in other strains of mice.

The levels of routine clinical indicators of liver and kidney injury and disease are within normal ranges and are not significantly changed relative to saline-treated animals, demonstrating that the compounds of the invention do not significantly affect renal or hepatic function. Triglyceride and glucose levels, while outside the normal range for most mice as is common in the Balb/c strain, are not significantly elevated relative to saline-treated animals.

Mice injected with ISIS 145733, 257016, 323294 and 323295 were also evaluated histologically following routine procedures. Liver, spleen, kidney, intestine, pancreas, lung, skin, heart and muscle samples were procured, fixed in 10% neutral-buffered formalin and processed for staining with hematoxylin and eosin, to visualize nuclei and cytoplasm, or with the anti-oligonucleotide IgG1 antibody 2E1-B5 (Berkeley Antibody Company, Berkeley, Calif.) to assess oligonucleotide staining patterns. Hematoxylin and eosin staining in most tissues exhibited no significant difference between saline- and oligonucleotide-treated animals. Heart sections from animals treated with 323294 and 323295 showed a high amount of inflammation relative to hearts from saline-treated mice. 2E1-B5 antibody was recognized using an isospecific anti-IgG2 horse-radish peroxidase-conjugated secondary antibody (Zymed, San Francisco, Calif.) and immunostaining was developed with 3,3'-diaminobenzidene (DAKO, Carpenteria, Calif.). 2E1-B5 staining was performed in duplicate and showed that none of the chemistries significantly stained the liver, while staining was observed in the kidney proximal tubules.

The results illustrated in this example demonstrate that antisense compounds of different chemistries are delivered to the kidney, reduce SGLT2 expression in vivo, and that treatment with these compounds does not result in liver or kidney toxicity.

Example 20

Effects of Antisense Compounds on SGLT2 mRNA Expression In Vivo: Dose Response Study Comparing Mixed Backbone and Full Phosphorothioate Backbones ISIS 145733 and ISIS 257016 were selected for a dose response study in mice. Male 8-week old Balb/c mice (Charles River Laboratories, Wilmington, Mass.) were given intraperitoneal injections of either ISIS 145733 or ISIS 257016 at doses of 6.25, 12.5, 25 and 50 mg/kg twice per week for two weeks. Saline-injected animals served as controls. A total of 4 animals were injected per group. The mice were sacrificed 2 days following administration of the fourth and final dose of oligonucleotide or saline.

Mice were evaluated for SGLT2 levels in kidney. Target levels were determined by quantitative real-time PCR as described by other examples herein. PCR results were normalized to cyclophilin as described in Example 19. The data are expressed as percent change ("+" indicates an increase, "−" indicates a decrease) relative to saline treated animals and are illustrated in Table 8.

TABLE 8

Antisense inhibition of SGLT2 mRNA expression in vivo by antisense compounds with varying chemistries

| Dose of oligonucleotide mg/kg | % change in SGLT2 expression relative to saline | |
|---|---|---|
| | ISIS 145733 | ISIS 257016 |
| 6.25 | −3 | −58 |
| 12.5 | −7 | −68 |
| 25 | −37 | −68 |
| 50 | −34 | −77 |

These results illustrate that the compounds of the invention, both full phosphorothioate and mixed backbone oligonucleotides, inhibit the expression of SGLT2 in vivo in a dose-dependent manner.

The levels of SGLT2 expression were also evaluated by Northern blot analysis of both pooled and individual RNA samples, to validate the target reduction observed by real-time PCR. Total RNA was prepared from procured tissues of sacrificed mice by homogenization in GITC buffer (Invitrogen, Carlsbad, Calif.) containing 2-mercaptoethanol (Sigma-Aldrich, St. Louis, Mo.) following manufacturer's recommended protocols followed by ultracentrifugation through a CsCl cushion. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer. RNA transfer was confirmed by UV visualization. Membranes were fixed by UV cross-linking using a STRATALINKER™ UV Crosslinker 2400 (Stratagene, Inc, La Jolla, Calif.) and then probed using RapidHYB™ hybridization solution (Amersham Pharmacia Biotech, Piscataway, N.J.) using manufacturer's recommendations for stringent conditions.

To detect mouse SGLT2, a mouse SGLT2 specific template was prepared by PCR using the forward primer 5'-ATGGAG-CAACACGTAGAGGCAGGCT-3' (SEQ ID NO: 263) and the reverse primer 5'-GAGTGCCGCCAGCCCTCCTGT-CACA-3' (SEQ ID NO: 264) and gel purified. The probe was prepared by asymmetric PCR with the purified template and the reverse primer incorporating $^{32}$P CTP to label the probe. Following hybridization blots were exposed overnight to phosphorimager screens (Molecular Dynamics, Amersham) and quantitated. To normalize for variations in loading and transfer efficiency membranes were stripped and probed for mouse glyceraldehyde-3-phosphate dehydrogenase (GAPDH) RNA (Clontech, Palo Alto, Calif.).

For pooled sample analysis, equal amounts of RNA isolated from the kidneys of mice in the same treatment was combined for a total of 20 μg, and the pooled sample was subjected to Northern blot analysis. The results of the pooled sample analysis are shown in Table 9 and are normalized to saline controls ("+" indicates an increase, "−" indicates a decrease).

TABLE 9

Northern Analysis of SGLT2 message in pooled kidney RNA samples

| Dose of oligonucleotide mg/kg | % change in SGLT2 expression relative to saline | |
|---|---|---|
| | ISIS 145733 | ISIS 257016 |
| 6.25 | +21 | −57 |
| 12.5 | +7 | −50 |
| 25 | −35 | −75 |
| 50 | −35 | −82 |

These results demonstrate that, as determined by Northern blot analysis of pooled samples, ISIS 257016 inhibits SGLT2 expression inhibits SGLT2 expression at all doses of antisense compound in a dose-dependent manner, where as ISIS 145733 inhibits SLGT2 expression at the two highest doses of antisense compound.

Target levels in kidney RNA samples from individual mice were also measured by Northern blot analysis. Equal amounts of RNA were individually subjected to Northern blot analysis to determine the level of SGLT2. Target level measurements for each treatment group were then averaged. The results are shown in Table 10 and are normalized to saline controls ("−" indicates a decrease).

TABLE 10

Northern analysis of SGLT2 message in individually measured RNA samples

| Dose of oligonucleotide mg/kg | % change in SGLT2 expression relative to saline | |
|---|---|---|
| | ISIS 145733 | ISIS 257016 |
| 6.25 | −34 | −66 |
| 12.5 | −38 | −68 |
| 25 | −39 | −74 |
| 50 | −59 | −82 |

Treated mice were further evaluated at the end of the treatment period for total body, liver and spleen weight. The data are expressed as percent change ("+" indicates an increase, "−" indicates a decrease) relative to saline control. The results are presented in Table 11.

TABLE 11

Effects of antisense compounds on total body weight, liver weight and spleen weight in mice

| Dose of oligonucleotide mg/kg | % Change relative to saline-treated | | | | | |
|---|---|---|---|---|---|---|
| | ISIS 145733 | | | ISIS 257016 | | |
| | Total Body | Liver | Spleen | Total Body | Liver | Spleen |
| 6.25 | −4 | −10 | −12 | −1 | −3 | +1 |
| 12.5 | −6 | −2 | −7 | −3 | −13 | −9 |
| 25 | 1 | −1 | +10 | 1 | −8 | +8 |
| 50 | −1 | +6 | +10 | −3 | −9 | +12 |

These data demonstrate that no significant changes in total body, liver or spleen weights are observed following treatment with ISIS 145733 or ISIS 257016 at 4 different doses.

No changes in total body weight were observed during the treatment period, or at study termination.

In addition to the indicators of toxicity listed in Example 19, creatinine levels are also used to evaluate renal function. In accordance with the present invention, the levels of ALT, AST, total bilirubin, creatinine, BUN, glucose and triglyceride were measured in mice treated with the compounds of the invention. Serum was analyzed by LabCorp Testing Facility (San Diego, Calif.). The results are expressed as units measured and are shown in Table 12.

TABLE 12

Effects of antisense compounds targeting SGLT2 on liver and kidney function in mice

| Serum indicator | Normal Range | Saline | 145733 25 mg/kg | 145733 50 mg/kg | 257016 25 mg/kg | 257016 50 mg/kg |
| --- | --- | --- | --- | --- | --- | --- |
| BUN mg/dL | 15-40 | 24 | 24 | 25 | 26 | 26 |
| Creatinine mg/L | 0.0-1.0 | 0.1 | 0.1 | 0.1 | 0.125 | 0.1 |
| Bilirubin mg/dL | 0.1-1.0 | 0.125 | 0.1 | 0.1 | 0.1 | 0.1 |
| AST IU/L | 30-300 | 77 | 65 | 96 | 133 | 141 |
| ALT IU/L | 30-200 | 24 | 18 | 22 | 34 | 35 |
| Triglycerides mg/dL | 25-100* | 165 | 169 | 230 | 130 | 111 |
| Glucose mg/dL | 80-150* | 236 | 280 | 256 | 244 | 248 |

*Triglyceride and glucose levels are routinely higher in the Balb/c strain of mice than in other strains of mice.

The AST levels in animals treated with 25 mg/kg of ISIS 145733 are slightly below the normal range, as is the ALT level for saline treated mice. Otherwise, the levels of routine clinical indicators of liver and kidney injury and disease are within normal ranges and are not significantly changed relative to saline-treated animals, demonstrating that the compounds of the invention do not significantly affect renal or hepatic function. Triglyceride and glucose levels, while outside the normal range as is common in the Balb/c strain, are not significantly elevated relative to saline-treated animals.

Mice injected with ISIS 145733 and 257016 at doses from 6.25 to 50 mg/kg were also evaluated histologically following routine procedures. Liver and kidney samples were procured, fixed in 10% neutral-buffered formalin and processed for staining with hematoxylin and eosin, to visualize nuclei and cytoplasm, or with the anti-oligonucleotide IgG1 antibody 2E1-B5 (Berkeley Antibody Company, Berkeley, Calif.) to assess oligonucleotide staining patterns. Hematoxylin and eosin staining exhibited no significant difference between saline- and oligonucleotide-treated animals. 2E1-B5 antibody was recognized using an isospecific anti-IgG2 horseradish peroxidase-conjugated secondary antibody (Zymed, San Francisco, Calif.) and immunostaining was developed with 3,3'-diaminobenzidene (DAKO, Carpenteria, Calif.). 2E1 staining showed no detectable oligonucleotide in the liver, while staining was observed in the kidney proximal tubules. Staining intensity lessened concomitantly with a decrease in oligonucleotide dose.

The results illustrated in this example demonstrate that antisense compounds of different chemistries are delivered to the kidney, reduce SGLT2 expression in vivo in a dose-dependent manner, and that treatment with these compounds does not result in liver or kidney toxicity.

Example 21

Effects of Antisense Compounds on SGLT2 mRNA Expression In Vivo: an Additional Dose Response Study Comparing Mixed Backbone and Full Phosphorothioate Backbones ISIS 145733 and ISIS 257016 were selected for a dose response study in mice using two identical and two lower doses with respect to the doses used in Example 20.

Male 8-week old Balb/c mice (Charles River Laboratories, Wilmington, Mass.) were given intraperitoneal injections of ISIS 145733 or ISIS 257016 at doses of 1, 5, 25 or 50 mg/kg twice per week for two weeks. Saline-injected animals served as a control. In addition, as a specificity control, the same doses of SGLT2 antisense oligomeric compounds do not significantly inhibit expression of SGLT1 mRNA in kidney cells. Each treatment group contained 4 mice. The mice were sacrificed 2 days following administration of the fourth and final dose of oligonucleotide or saline.

Mice were evaluated for SGLT2 levels in kidney and liver. Target levels were determined by quantitative real-time PCR as described by other examples herein. PCR results were normalized to cyclophilin. The data are expressed as percent change relative to saline treated animals ("+" indicates an increase, "−" indicates a decrease) and are illustrated in Table 13.

TABLE 13

Antisense inhibition of SGLT2 mRNA expression in vivo by antisense compounds with varying chemistries

| | % change in SGLT2 expression relative to saline | | | |
|---|---|---|---|---|
| Dose of | Kidney | | Liver | |
| oligonucleotide mg/kg | ISIS 145733 | ISIS 257016 | ISIS 145733 | ISIS 257016 |
| 1 | +2 | −46 | −19 | +13 |
| 5 | −15 | −64 | −39 | +1 |
| 25 | −34 | −74 | −21 | −5 |
| 50 | −40 | −76 | −59 | −12 |

These results illustrate that the compounds of the invention, both full phosphorothioate and mixed backbone oligonucleotides, can inhibit the expression of kidney SGLT2 in a dose-dependent manner. Greater inhibition is observed in kidneys from mice treated with ISIS 257016, a mixed backbone antisense compound. SGLT2 is not highly expressed in liver, therefore target levels are low before treatment and therefore more difficult to accurately measure. While ISIS 145733 and ISIS 257016 also lowered liver SGLT2 expression, with 145733 having a greater effect in liver than the mixed backbone ISIS 257016.

Treated mice were further evaluated for liver and spleen weight. The data are expressed as percent change ("+" indicates an increase, "−" indicates a decrease) relative to saline control. The results are presented in Table 14.

TABLE 14

Effects of antisense compounds on total body weight, liver weight and spleen weight in mice

| | % change in body, liver and spleen weight | | | | | |
|---|---|---|---|---|---|---|
| Dose of | ISIS 145733 | | | ISIS 257016 | | |
| oligonucleotide mg/kg | Total Body | Liver | Spleen | Total Body | Liver | Spleen |
| 1 | 0 | −6 | +10 | −2 | −8 | +13 |
| 5 | +3 | +1 | +10 | −3 | −9 | +5 |
| 25 | −1 | +2 | −4 | +2 | +2 | +12 |
| 50 | −1 | +13 | +35 | −2 | −6 | +15 |

No significant change was observed in total body weight at timepoints throughout or at the termination of the study. Treatments of 25 mg/kg ISIS 145733 and 50 mg/kg 257016 resulted in a decrease and increase in liver weight, respectively, however, these changes are within the margin of error for the data and are therefore not significant.

In addition to the other serum markers described herein, cholesterol levels can be used as a measure of toxicity. In accordance with the present invention, the levels of ALT, AST, total bilirubin, albumin, creatinine, BUN, triglyceride, cholesterol and glucose were measured in mice treated with the compounds of the invention. Plasma samples were analyzed using the Olympus AU400e automated chemistry analyzer (Olympus America, Irving, Tex.). The results are expressed as units measured are shown for ISIS 145733 in Table 15 and for ISIS 257016 in Table 16.

TABLE 15

Effects of the full phosphorothioate antisense compound ISIS 145733 on indicators of liver and kidney function

| | | | Units measured per dose of ISIS 145733 | | | |
|---|---|---|---|---|---|---|
| Serum indicator | Normal Range | Saline | 1 mg/kg | 5 mg/kg | 25 mg/kg | 50 mg/kg |
| BUN mg/dL | 15-40 | 27 | 31 | 31 | 30 | 25 |
| Creatinine mg/L | 0.0-1.0 | 0.2 | 0.2 | 0.2 | 0.2 | 0.2 |
| Bilirubin mg/dL | 0.1-1.0 | 0.3 | 0.2 | 0.1 | 0.3 | 0.1 |
| AST IU/L | 30-300 | 92 | 91 | 45 | 133 | 56 |
| ALT IU/L | 30-200 | 35 | 27 | 26 | 37 | 31 |
| Albumin g/dL | 2.5-4.0 | 3 | 3 | 3 | 3 | 3 |
| Triglycerides mg/dL | 25-100* | 136 | 188 | 183 | 153 | 224 |
| Cholesterol mg/dL | 70-125 | 122 | 116 | 117 | 120 | 132 |
| Glucose mg/dL | 80-150* | 208 | 202 | 173 | 170 | 161 |

TABLE 16

Effects of the mixed backbone antisense compound ISIS 257016 on indicators of liver and kidney function

| | | | Units measured per dose of ISIS 257016 | | | |
|---|---|---|---|---|---|---|
| Serum indicator | Normal Range | Saline | 1 mg/kg | 5 mg/kg | 25 mg/kg | 50 mg/kg |
| BUN mg/dL | 15-40 | 27 | 23 | 29 | 25 | 28 |
| Creatinine mg/L | 0.0-1.0 | 0.2 | 0.2 | 0.2 | 0.2 | 0.2 |
| Bilirubin mg/dL | 0.1-1.0 | 0.3 | 0.2 | 0.2 | 0.2 | 0.2 |
| AST IU/L | 30-300 | 92 | 74 | 73 | 99 | 138 |
| ALT IU/L | 30-200 | 35 | 34 | 34 | 46 | 48 |
| Albumin g/dL | 2.5-4.0 | 3 | 3 | 3 | 3 | 3 |
| Triglycerides mg/dL | 25-100* | 136 | 271 | 233 | 225 | 136 |
| Cholesterol mg/dL | 70-125 | 122 | 116 | 124 | 144 | 137 |
| Glucose mg/dL | 80-150* | 208 | 180 | 178 | 154 | 182 |

*Triglyceride and glucose levels are routinely higher in the Balb/c strain of mice than in other strains of mice.

The levels of routine clinical indicators of liver and kidney injury and disease are within normal ranges and are not significantly changed relative to saline-treated animals, demonstrating that the compounds of the invention do not significantly affect renal or hepatic function. Triglyceride and glucose levels, while outside the normal range as is common in the Balb/c strain, are not significantly elevated relative to saline-treated animals.

Mice injected ISIS 145733 and 257016 at 1-50 mg/kg were also evaluated histologically following routine procedures. Liver and kidney samples were procured, fixed in 10% neutral-buffered formalin and processed for staining with hematoxylin and eosin, to visualize nuclei and cytoplasm, or with the anti-oligonucleotide IgG1 antibody 2E1-B5 (Berkeley Antibody Company, Berkeley, Calif.) to assess oligonucleotide staining patterns. Hematoxylin and eosin staining in most tissues exhibited no significant difference between saline- and 145733-treated animals, with the exception of slight inflammatory cell infiltration in the liver tissue. Livers from mice treated with ISIS 257016 showed evidence of nuclear degradation and mitosis at 50 mg/kg and slight mitosis at 25 mg/kg. Kidneys from ISIS 257016 exhibited no significant differences compared to saline-treated kidneys. 2E1-B5 antibody was recognized using an isospecific anti-IgG2 horse-radish peroxidase-conjugated secondary antibody (Zymed, San Francisco, Calif.) and immunostaining was developed with 3,3'-diaminobenzidene (DAKO, Carpenteria, Calif.). Staining with the 2E1 antibody showed weak staining in liver and kidneys from animals treated with ISIS 145733, whereas staining was strong in liver and kidney from animals treated with ISIS 257016. Kidney 2E1 staining appears in a punctate pattern.

Example 22

Dose Response Study Comparing Mixed Backbone and Full Phosphorothioate Backbones: a Second SGLT2 Antisense Sequence A second mixed backbone SGLT2 oligonucleotide, ISIS 341699 (SEQ ID NO: 265), and control phosphorothioate SGLT2 oligonucleotide, ISIS 145742 (SEQ ID NO: 265), were selected for a dose response study in mice. For comparison, ISIS 257016 (mixed backbone; SEQ ID NO: 106) also was included in this study.

Male 8-week old Balb/c mice (Charles River Laboratories, Wilmington, Mass.) were given intraperitoneal injections of ISIS 341699, ISIS 145742 or ISIS 257016 twice per week for two weeks with the doses shown in Table 17. Saline-injected animals served as controls. Each treatment group contained 4 mice. The mice were sacrificed 2 days following administration of the fourth and final dose of oligonucleotide or saline.

Mice were evaluated for SGLT2 levels in kidney. Target levels were determined by quantitative real-time PCR as described by other examples herein. PCR results were normalized to cyclophilin. The data are expressed as percent change relative to saline treated animals ("+" indicates an increase, "−" indicates a decrease) and are illustrated in Table 17.

TABLE 17

Antisense inhibition of SGLT2 mRNA expression in vivo by mixed backbone and full phosphorothioate oligonucleotides (expressed as percent change in SGLT2 mRNA expression relative to saline)

| Dose of oligonucleotide mg/kg | ISIS 145742 | ISIS 341699 | ISIS 257016 |
|---|---|---|---|
| 0.2 | — | — | −18.9 |
| 1 | — | −1.8 | −50.5 |
| 5 | −0.6 | −10.9 | −56.7 |
| 25 | −24.9 | −23.9 | — |
| 50 | −32.6 | — | — |

These results illustrate that the compounds of the invention, both full phosphorothioate and mixed backbone oligonucleotides, can inhibit the expression of kidney SGLT2 in a dose-dependent manner. However, lower doses of the mixed backbone compound are required to inhibit SGLT2 expression in kidneys from treated mice.

Treated mice were further evaluated for liver and spleen weight. The data are expressed as percent change in body or organ weight ("+" indicates an increase, "−" indicates a decrease). The results are presented in Table 18 and Table 19.

TABLE 18

Effects of antisense compounds on total body weight of mice (expressed as percent change in body weight)

| Dose of oligonucleotide mg/kg | ISIS 145742 | ISIS 341699 | ISIS 257016 |
|---|---|---|---|
| 0.2 | — | — | +7.9 |
| 1 | — | +5.7 | +5.8 |
| 5 | +5.0 | +5.8 | +3.2 |
| 25 | +2.0 | +2.5 | — |
| 50 | +7.2 | — | — |

TABLE 19

Effects of antisense compounds on liver weight and spleen weight of mice (expressed as percent change in organ weight)

| Dose of oligonucleotide mg/kg | Liver | | | Spleen | | |
|---|---|---|---|---|---|---|
| | ISIS 145742 | ISIS 341699 | ISIS 257016 | ISIS 145742 | ISIS 341699 | ISIS 257016 |
| 0.2 | — | — | −6.0 | — | — | −4.7 |
| 1 | — | +2.3 | +14.9 | — | −4.2 | +1.4 |
| 5 | +7.1 | +2.2 | +7.0 | +10.6 | −2.8 | −7.6 |
| 25 | +7.2 | +5.8 | — | +0.8 | −0.2 | — |
| 50 | +12.1 | — | — | +9.4 | — | — |

No significant change was observed in total body weight, liver weight or spleen weight at timepoints throughout or at the termination of the study.

Levels of BUN, creatinine, AST, ALT, albumin, triglycerides, cholesterol and glucose were measured in mice treated with the compounds of the invention. Plasma samples were analyzed using the Olympus AU400e automated chemistry analyzer (Olympus America, Irving, Tex.). The results, expressed as units measured, are shown for ISIS 145742 in Table 20, ISIS 341699 in Table 21 and ISIS 257016 in Table 22.

TABLE 20

Effect of the full phosphorothioate antisense compound ISIS 145742 on indicators of liver and kidney function

| Serum indicator | Normal Range | Saline | Units measured per dose of ISIS 145742 | | |
|---|---|---|---|---|---|
| | | | 5 mg/kg | 25 mg/kg | 50 mg/kg |
| BUN mg/dL | 15-40 | 20 | 21.3 | 25.5 | 20.8 |
| Creatinine mg/L | 0.0-1.0 | 0.1 | 0.2 | 0.2 | 0.2 |
| AST IU/L | 30-300 | 113 | 75.3 | 83.5 | 145.3 |
| ALT IU/L | 30-200 | 35.5 | 29.8 | 40.3 | 47.5 |
| Albumin g/dL | 2.5-4.0 | 3.0 | 3.0 | 2.9 | 2.9 |
| Triglycerides mg/dL | 25-100* | 223.8 | 176.5 | 192 | 176.8 |
| Cholesterol mg/dL | 70-125 | 129 | 119.5 | 119.5 | 113.5 |
| Glucose mg/dL | 80-150* | 176.5 | 196.5 | 192 | 194.8 |

TABLE 21

Effect of mixed backbone antisense compound ISIS 341699
on indicators of liver and kidney function

| Serum indicator | Normal Range | Units measured per dose of ISIS 341699 | | |
| --- | --- | --- | --- | --- |
| | | Saline | 1 mg/kg | 5 mg/kg | 25 mg/kg |
| BUN mg/dL | 15-40 | 20 | 20 | 21.8 | 22 |
| Creatinine mg/L | 0.0-1.0 | 0.1 | 0.2 | 0.2 | 0.2 |
| AST IU/L | 30-300 | 113 | 78.2 | 119 | 64.8 |
| ALT IU/L | 30-200 | 35.5 | 36.2 | 37.3 | 33.0 |
| Albumin g/dL | 2.5-4.0 | 3.0 | 3.3 | 3.1 | 3.2 |
| Triglycerides mg/dL | 25-100* | 223.8 | 206.4 | 186.8 | 183.5 |
| Cholesterol mg/dL | 70-125 | 129 | 135 | 124 | 120.8 |
| Glucose mg/dL | 80-150* | 176.5 | 203.2 | 171.5 | 197 |

TABLE 22

Effect of mixed backbone antisense compound ISIS 257016 on
indicators of liver and kidney function

| Serum indicator | Normal Range | Units measured per dose of ISIS 257016 | | |
| --- | --- | --- | --- | --- |
| | | Saline | 0.2 mg/kg | 1 mg/kg | 5 mg/kg |
| BUN mg/dL | 15-40 | 20 | 21.8 | 26.3 | 20.5 |
| Creatinine mg/L | 0.0-1.0 | 0.1 | 0.2 | 0.2 | 0.2 |
| AST IU/L | 30-300 | 113 | 123.8 | 85.3 | 69.5 |
| ALT IU/L | 30-200 | 35.5 | 36.8 | 44 | 43 |
| Albumin g/dL | 2.5-4.0 | 3.0 | 3.1 | 3.4 | 3.1 |
| Triglycerides mg/dL | 25-100* | 223.8 | 138.8 | 268.3 | 212.8 |
| Cholesterol mg/dL | 70-125 | 129 | 128 | 152 | 135.3 |
| Glucose mg/dL | 80-150* | 176.5 | 208.8 | 212.3 | 164.5 |

*Triglyceride and glucose levels are routinely higher in the Balb/c strain of mice than in other strains of mice.

In some oligonucleotide-treated animals cholesterol levels were above the normal range; however, this elevation is not significant since saline-treated animals also exhibited cholesterol above the normal range. The levels of the remaining routine clinical indicators of liver and kidney injury and disease are within normal ranges and are not significantly changed relative to saline-treated animals, demonstrating that the compounds of the invention do not significantly affect renal or hepatic function. Triglyceride and glucose levels, while outside the normal range as is common in the Balb/c strain, are not significantly elevated relative to saline-treated animals.

Mice injected with ISIS 145742, ISIS 341699 and ISIS 257016 at 0.2-50 mg/kg were also evaluated histologically following routine procedures. Liver and kidney samples were procured, fixed in 10% neutral-buffered formalin and processed for staining with hematoxylin and eosin or with the anti-oligonucleotide IgG1 antibody 2E1-B5, as described in other examples herein. Hematoxylin and eosin staining in both liver and kidney tissues exhibited no significant difference between saline- and antisense oligonucleotide-treated animals. Staining with the 2E1 antibody showed high background in sinusoidal tissues of liver from the saline-injected animals, therefore making it difficult to interpret positive staining in the oligonucleotide-treated livers. Kidney samples from saline-injected animals and animals treated with 0.2 mg/kg ISIS 257016 showed no positive oligonucleotide staining; however, the remainder of the oligonucleotide-treated animals demonstrated high levels of staining in the proximal tubules, which increased with dose.

The results illustrated in this example demonstrate that antisense compounds of different chemistries are delivered to the kidney, reduce SGLT2 expression in vivo in a dose-dependent manner, and that treatment with these compounds does not result in liver or kidney toxicity. The results further demonstrate that mixed backbone compounds ISIS 341699 and ISIS 257016 are particularly effective at reducing target mRNA levels in the kidney.

Example 23

Dose Response Study Comparing Mixed Backbone and Full Phosphorothioate Backbones: a Third SGLT2 Antisense Sequence A third mixed backbone SGLT2 oligonucleotide, ISIS 351642 (SEQ ID NO: 266), and control phosphorothioate SGLT2 oligonucleotide, ISIS 145746 (SEQ ID NO: 266), were selected for a dose response study in mice.

Male 7-week old Balb/c mice (Charles River Laboratories, Wilmington, Mass.) were given intraperitoneal injections of ISIS 145746 or ISIS 351642 twice per week for two weeks with the doses shown in Table 23. Saline-injected animals served as controls. Each treatment group contained 4 mice. The mice were sacrificed 2 days following administration of the fourth and final dose of oligonucleotide or saline.

Mice were evaluated for SGLT2 levels in kidney. Target levels were determined by quantitative real-time PCR as described by other examples herein. PCR results were normalized to cyclophilin. The data are expressed as percent change relative to saline treated animals ("+" indicates an increase, "−" indicates a decrease) and are illustrated in Table 23.

TABLE 23

Antisense inhibition of SGLT2 mRNA expression in vivo by
mixed backbone and full phosphorothioate oligonucleotides
(expressed as percent change in SGLT2 mRNA expression
relative to saline)

| Dose of oligonucleotide mg/kg | ISIS 145746 | ISIS 351642 |
| --- | --- | --- |
| 1 | — | −26.7 |
| 5 | −5.8 | −35.1 |
| 25 | −10.5 | −44.3 |
| 50 | −35.6 | −31.8 |

These results illustrate that the compounds of the invention, both full phosphorothioate and mixed backbone oligonucleotides, can inhibit the expression of kidney SGLT2 in a dose-dependent manner. At doses of 5 and 25 mg/kg, greater inhibition is observed in kidneys from mice treated with ISIS 351462, suggesting the mixed backbone antisense compound is a more efficient inhibitor of target mRNA expression in the kidney.

Treated mice were further evaluated for body weight, liver weight and spleen weight. The data are expressed as percent change in body or organ weight ("+" indicates an increase, "−" indicates a decrease). The results are presented in Table 24.

TABLE 24

Effects of antisense compounds on total body weight, liver weight and spleen weight of mice

| Dose of oligonucleotide mg/kg | Percent change in weight | | | | | |
|---|---|---|---|---|---|---|
| | ISIS 145746 | | | ISIS 351642 | | |
| | Total Body | Liver | Spleen | Total Body | Liver | Spleen |
| 1 | — | — | — | +6.9 | −8.2 | +0.8 |
| 5 | +3.6 | −5.7 | +6.5 | +4.6 | −0.6 | −7.9 |
| 25 | +5.4 | −2.0 | +3.7 | +4.7 | −10.6 | +1.1 |
| 50 | +12.1 | −8.4 | +10.0 | +7.4 | −3.0 | +1.3 |

No significant change was observed in total body weight, liver weight or spleen weight at timepoints throughout or at the termination of the study.

Levels of BUN, creatinine, AST, ALT, albumin, triglycerides, cholesterol and glucose were measured in mice treated with the compounds of the invention. Plasma samples were analyzed using the Olympus AU400e automated chemistry analyzer (Olympus America, Irving, Tex.). The results, expressed as units measured, are shown for ISIS 145746 in Table 25 and ISIS 351642 in Table 26.

TABLE 25

Effect of the full phosphorothioate antisense compound ISIS 145746 on indicators of liver and kidney function

| Serum indicator | Normal Range | Saline | Units measured per dose of ISIS 145746 | | | |
|---|---|---|---|---|---|---|
| | | | 1 mg/kg | 5 mg/kg | 25 mg/kg | 50 mg/kg |
| Creatinine mg/L | 0.0-1.0 | 0.1 | — | 0.2 | 0.2 | 0.1 |
| AST IU/L | 30-300 | 129 | — | 60 | 84 | 155 |
| ALT IU/L | 30-200 | 30 | — | 28 | 26 | 77 |
| Albumin g/dL | 2.5-4.0 | 2.8 | — | 2.9 | 2.8 | 2.9 |
| Triglycerides mg/dL | 25-100* | 298 | — | 268 | 259 | 236 |
| Cholesterol mg/dL | 70-125 | 116 | — | 118 | 108 | 106 |
| Glucose mg/dL | 80-150* | 163 | — | 162 | 181 | 179 |

TABLE 26

Effect of mixed backbone antisense compound ISIS 351642 on indicators of liver and kidney function

| Serum indicator | Normal Range | Saline | Units measured per dose of ISIS 351642 | | | |
|---|---|---|---|---|---|---|
| | | | 1 mg/kg | 5 mg/kg | 25 mg/kg | 50 mg/kg |
| Creatinine mg/L | 0.0-1.0 | 0.1 | 0.1 | 0.1 | 0.2 | 0.2 |
| AST IU/L | 30-300 | 129 | 132 | 75 | 131 | 160 |
| ALT IU/L | 30-200 | 30 | 31 | 28 | 29 | 31 |
| Albumin g/dL | 2.5-4.0 | 2.8 | 2.9 | 3.0 | 2.7 | 2.8 |
| Triglycerides mg/dL | 25-100* | 298 | 238 | 287 | 240 | 233 |
| Cholesterol mg/dL | 70-125 | 116 | 117 | 122 | 106 | 113 |
| Glucose mg/dL | 80-150* | 163 | 195 | 175 | 164 | 171 |

*Triglyceride and glucose levels are routinely higher in the Balb/c strain of mice than in other strains of mice.

The levels of routine clinical indicators of liver and kidney injury and disease are within normal ranges and are not significantly changed relative to saline-treated animals, demonstrating that the compounds of the invention do not significantly affect renal or hepatic function. Triglyceride and glucose levels, while outside the normal range as is common in the Balb/c strain, are not significantly elevated relative to saline-treated animals.

The results illustrated in this example demonstrate that antisense compounds of different chemistries are delivered to the kidney, reduce SGLT2 expression in vivo in a dose-dependent manner, and that treatment with these compounds does not result in liver or kidney toxicity. The results further suggest that mixed backbone compound ISIS 351642 is more effective than full phosphorothioate oligonucleotides at reducing target mRNA levels in the kidney, particularly at low doses.

Example 24

Comparison of a Standard Mixed Backbone Compound and a Mixed Backbone Compound with Phosphorothioate Linkages at the Extreme 5' and 3' Ends: a Single Dose Study In accordance with the present invention, ISIS 257016 (SEQ ID NO: 106) and ISIS 351641 (SEQ ID NO: 106) were analyzed for their ability to inhibit SGLT2 expression in vivo. ISIS 257016 is a standard mixed backbone compound having 2'-MOE wings and a deoxy gap, with phosphodiester linkages in the wings and phosphorothioate linkages in the gap. ISIS 351641 differs from the standard mixed backbone compounds by having one phosphorothioate linkage at each of the extreme 5' and 3' ends of the wings.

Male 8-week old Balb/c mice (Charles River Laboratories, Wilmington, Mass.) were given a single intraperitoneal injection of ISIS 257016 or ISIS 351641 at a dose of 1, 5, 25 or 50 mg/kg. Saline-injected animals served as controls. Each treatment group contained 4 mice. The mice were sacrificed 2 days following administration of the single dose of oligonucleotide or saline.

Mice were evaluated for SGLT2 levels in kidney. Target levels were determined by quantitative real-time PCR as described by other examples herein. PCR results were normalized to cyclophilin. The data are expressed as percent change relative to saline treated animals ("+" indicates an increase, "−" indicates a decrease) and are illustrated in Table 27.

TABLE 27

Antisense inhibition of SGLT2 mRNA expression in vivo by mixed backbone oligonucleotides (expressed as percent change in SGLT2 mRNA expression relative to saline)

| Dose of oligonucleotide mg/kg | ISIS 257016 | ISIS 351641 |
|---|---|---|
| 1 | −21.5 | −14.0 |
| 5 | −26.4 | −19.3 |
| 25 | −24.2 | −12.5 |
| 50 | −36.3 | −22.0 |

These results illustrate that mixed backbone compounds of the invention, with either complete phosphodiester linkages in the wings, or with the extreme 5' and 3' ends substituted with phosphorothioate linkages, inhibit the expression of kidney SGLT2 in a dose-dependent manner. However, greater inhibition is observed in kidneys from mice treated with ISIS 257016, which contains all phosphodiester linkages in the wings.

Treated mice were further evaluated for body weight and liver and spleen weight. The data are expressed as percent change in body or organ weight ("+" indicates an increase, "−" indicates a decrease). The results are presented in Table 28.

TABLE 28

Effects of antisense compounds on total body weight, liver weight and spleen weight of mice

| | Percent change in weight | | | | | |
|---|---|---|---|---|---|---|
| | ISIS 257016 | | | ISIS 351641 | | |
| Dose of oligonucleotide mg/kg | Total Body | Liver | Spleen | Total Body | Liver | Spleen |
| 1 | −0.9 | +1.2 | −1.6 | +2.8 | +3.0 | −0.1 |
| 5 | −5.1 | +5.4 | +20.1 | +4.0 | +2.1 | +9.7 |
| 25 | −1.1 | +3.5 | +3.8 | −0.7 | +9.3 | +5.9 |
| 50 | −2.5 | −2.3 | +7.8 | +0.9 | −0.7 | +10.2 |

No significant change was observed in total body weight, liver weight or spleen weight at timepoints throughout or at the termination of the study.

Levels of creatinine, AST, ALT, albumin, triglycerides, cholesterol and glucose were measured in mice treated with the compounds of the invention. Plasma samples were analyzed using the Olympus AU400e automated chemistry analyzer (Olympus America, Irving, Tex.). The results, expressed as units measured, are shown for ISIS 257016 in Table 29 and for ISIS 351641 in Table 30.

TABLE 29

Effect of mixed backbone antisense compound ISIS 257016 on indicators of liver and kidney function

| | | | Units measured per dose of ISIS 257016 | | | |
|---|---|---|---|---|---|---|
| Serum indicator | Normal Range | Saline | 1 mg/kg | 5 mg/kg | 25 mg/kg | 50 mg/kg |
| Creatinine mg/L | 0.0-1.0 | 0.0 | 0.0 | 0.0 | 0.0 | 0.2 |
| AST IU/L | 30-300 | 141 | 62 | 77 | 89 | 88 |
| ALT IU/L | 30-200 | 30 | 29 | 28 | 27 | 33 |
| Albumin g/dL | 2.5-4.0 | 2.9 | 2.8 | 2.8 | 3.0 | 2.9 |
| Triglycerides mg/dL | 25-100* | 213 | 253 | 255 | 347 | 245 |
| Cholesterol mg/dL | 70-125 | 118 | 111 | 116 | 125 | 120 |
| Glucose mg/dL | 80-150* | 155 | 186 | 172 | 174 | 169 |

TABLE 30

Effect of mixed backbone antisense compound ISIS 351641 on indicators of liver and kidney function

| | | | Units measured per dose of ISIS 351641 | | | |
|---|---|---|---|---|---|---|
| Serum indicator | Normal Range | Saline | 1 mg/kg | 5 mg/kg | 25 mg/kg | 50 mg/kg |
| Creatinine mg/L | 0.0-1.0 | 0.0 | 0.2 | 0.1 | 0.1 | 0.2 |
| AST IU/L | 30-300 | 141 | 75 | 117 | 68 | 98 |
| ALT IU/L | 30-200 | 30 | 25 | 33 | 30 | 27 |
| Albumin g/dL | 2.5-4.0 | 2.9 | 2.9 | 2.9 | 2.9 | 2.9 |
| Triglycerides mg/dL | 25-100* | 213 | 271 | 280 | 296 | 271 |
| Cholesterol mg/dL | 70-125 | 118 | 120 | 126 | 112 | 117 |
| Glucose mg/dL | 80-150* | 155 | 162 | 171 | 189 | 175 |

*Triglyceride and glucose levels are routinely higher in the Balb/c strain of mice than in other strains of mice.

The levels of routine clinical indicators of liver and kidney injury and disease are within normal ranges and are not significantly changed relative to saline-treated animals, demonstrating that the compounds of the invention do not significantly affect renal or hepatic function. Triglyceride and glucose levels, while outside the normal range as is common in the Balb/c strain, are not significantly elevated relative to saline-treated animals.

The results illustrated in this example demonstrate that mixed backbone compounds of varying chemistries are delivered to the kidney, reduce SGLT2 expression in vivo, and that treatment with these compounds does not result in liver or kidney toxicity. The results further indicate that mixed backbone compounds with wings composed completely of phosphodiester linkages are more efficient inhibitors of target mRNA.

Example 25

Effects of Modified Antisense Compounds on SGLT2 mRNA Expression in Vivo: Two and Three Dose Protocols In accordance with the present invention, mixed backbone compound ISIS 257016 (SEQ ID NO; 106) was analyzed for its ability to inhibit SGLT2 expression in vivo when administered in either two or three doses. ISIS 353003 (CCTTC-CCTGAAGGTTCCTCC; SEQ ID NO: 267), a mixed backbone oligonucleotide which targets human PTP1B, was used as a control.

Male 8-week old Balb/c mice (Charles River Laboratories, Wilmington, Mass.) were given two or three intraperitoneal injections of ISIS 257016 or ISIS 353003 at three day intervals. ISIS 257016 was administered at doses of 1, 5 or 25 mg/kg and ISIS 353003 was administered at a dose of 25 mg/kg. Saline-injected animals served as controls. Each treatment group contained 4 mice. The mice were sacrificed 2 days following administration of the final dose of oligonucleotide or saline.

Mice were evaluated for SGLT2 levels in kidney. Target levels were determined by quantitative real-time PCR as described in other examples herein. PCR results were normalized to cyclophilin. The data are expressed as percent change relative to saline treated animals ("+" indicates an increase, "−" indicates a decrease) and are illustrated in Table 31.

TABLE 31

Antisense inhibition of SGLT2 mRNA expression in vivo by two doses or three doses of mixed backbone oligonucleotides (expressed as percent change in SGLT2 mRNA expression relative to saline control)

| Oligonucleotide (dose in mg/kg) | Two Doses | Three Doses |
|---|---|---|
| ISIS 257016 (1 mg/kg) | −43.2 | −39.1 |
| ISIS 257016 (5 mg/kg) | −39.7 | −42.9 |
| ISIS 257016 (25 mg/kg) | −53.8 | −65.5 |
| ISIS 353003 (25 mg/kg) | −8.0 | −6.9 |

These results illustrate that the mixed backbone compounds of the invention efficiently inhibit the expression of kidney SGLT2 in a dose-dependent manner. Furthermore, inhibition increases with the number of doses administered.

Treated mice were further evaluated for body weight, kidney weight, liver weight and spleen weight. The data are expressed as percent change in body or organ weight ("+" indicates an increase, "−" indicates a decrease). The results are presented in Table 32 and Table 33.

TABLE 32

Effects of antisense compounds on total body weight of mice (expressed as percent change in body weight)

| Oligonucleotide (dose in mg/kg) | Two Doses | Three Doses |
|---|---|---|
| ISIS 257016 (1 mg/kg) | −1.1 | 0 |
| ISIS 257016 (5 mg/kg) | +1.3 | +0.8 |
| ISIS 257016 (25 mg/kg) | +0.1 | +1.3 |
| ISIS 353003 (25 mg/kg) | −0.8 | +0.8 |

TABLE 33

Effects of antisense compounds on total kidney weight, liver weight and spleen weight of mice

| | Percent change in weight | | | | | |
|---|---|---|---|---|---|---|
| | Two Doses | | | Three Doses | | |
| Oligonucleotide (dose in mg/kg) | Kidney | Liver | Spleen | Kidney | Liver | Spleen |
| ISIS 257016 (1 mg/kg) | −0.5 | −2.2 | −4.3 | −5.6 | −3.8 | −5.9 |
| ISIS 257016 (5 mg/kg) | −5.4 | +2.5 | +7.4 | −6.6 | −7.1 | −9.0 |
| ISIS 257016 (25 mg/kg) | −7.9 | −1.1 | +4.2 | −8.6 | −8.8 | −1.2 |
| ISIS 353003 (25 mg/kg) | −5.5 | +1.2 | −2.7 | −0.2 | −4.0 | +6.5 |

No significant change was observed in total body weight, kidney weight, liver weight or spleen weight at timepoints throughout or at the termination of the study.

Levels of BUN, creatinine, bilirubin, AST, ALT, albumin, triglycerides, cholesterol and glucose were measured in mice treated with the compounds of the invention. Plasma samples were analyzed using the Olympus AU400e automated chemistry analyzer (Olympus America, Irving, Tex.). The results, expressed as units measured, are shown for the two dose protocol in Table 34 and for the three dose protocol in Table 35.

TABLE 34

Effect of mixed backbone antisense compound ISIS 257016 administered according to the two dose protocol on indicators of liver and kidney function

| | | | Units measured per dose of ISIS 257016 | | | |
|---|---|---|---|---|---|---|
| Serum indicator | Normal Range | Saline | 1 mg/kg | 5 mg/kg | 25 mg/kg | ISIS 353003 |
| BUN mg/dL | 15-40 | 32 | 34 | 29 | 25 | 28 |
| Creatinine mg/L | 0.0-1.0 | 0.1 | 0.1 | 0.2 | 0.1 | 0.1 |
| Bilirubin mg/dL | 0.1-1.0 | 0.1 | 0.1 | 0.1 | 0.1 | 0.1 |
| AST IU/L | 30-300 | 54 | 119 | 156 | 116 | 154 |
| ALT IU/L | 30-200 | 27 | 36 | 45 | 30 | 36 |
| Albumin g/dL | 2.5-4.0 | 2.7 | 3.2 | 3.1 | 3.0 | 2.8 |
| Triglycerides mg/dL | 25-100* | 221 | 263 | 234 | 264 | 278 |
| Cholesterol mg/dL | 70-125 | 113 | 118 | 117 | 125 | 125 |
| Glucose mg/dL | 80-150* | 170 | 157 | 177 | 163 | 152 |

TABLE 35

Effect of mixed backbone antisense compound ISIS 257016 administered according to the three dose protocol on indicators of liver and kidney function

| Serum indicator | Normal Range | Saline | 1 mg/kg | 5 mg/kg | 25 mg/kg | ISIS 353003 |
|---|---|---|---|---|---|---|
| BUN mg/dL | 15-40 | 30 | 32 | 30 | 27 | 27 |
| Creatinine mg/L | 0.0-1.0 | 0.1 | 0.1 | 0.2 | 0.1 | 0.1 |
| Bilirubin mg/dL | 0.1-1.0 | 0.1 | 0.1 | 0.1 | 0.1 | 0.1 |
| AST IU/L | 30-300 | 126 | 83 | 81 | 59 | 57 |
| ALT IU/L | 30-200 | 35 | 30 | 57 | 27 | 24 |
| Albumin g/dL | 2.5-4.0 | 3.0 | 2.8 | 2.8 | 2.7 | 2.8 |
| Triglycerides mg/dL | 25-100* | 223 | 236 | 202 | 153 | 188 |
| Cholesterol mg/dL | 70-125 | 112 | 113 | 114 | 116 | 106 |
| Glucose mg/dL | 80-150* | 152 | 169 | 161 | 181 | 192 |

*Triglyceride and glucose levels are routinely higher in the Balb/c strain of mice than in other strains of mice.

The levels of routine clinical indicators of liver and kidney injury and disease are within normal ranges and are not significantly changed relative to saline-treated animals, demonstrating that the compounds of the invention do not significantly affect renal or hepatic function. Triglyceride and glucose levels, while outside the normal range as is common in the Balb/c strain, are not significantly elevated relative to saline-treated animals.

Mice injected with ISIS 257016 and control animals were also evaluated histologically following routine procedures. Liver and kidney samples were procured, fixed in 10% neutral-buffered formalin and processed for staining with hematoxylin and eosin. Hematoxylin and eosin staining exhibited no significant difference between saline- and oligonucleotide-treated animals. All tissue samples exhibited normal kidney and liver morphology.

The results illustrated in this example demonstrate that mixed backbone compounds are delivered to the kidney, reduce SGLT2 expression in vivo, and that treatment with these compounds does not result in liver or kidney toxicity. The results further indicate that inhibition of target mRNA expression in the kidney increases with the number of doses administered.

Example 26

Effects of Mixed Backbone Antisense Compounds on SGLT2 mRNA Expression In Vivo: Two to Five Day Consecutive Daily Dosing Protocols In accordance with the present invention, mixed backbone compound ISIS 257016 (SEQ ID NO: 106) was analyzed for its ability to inhibit SGLT2 expression in vivo when administered in two to five doses (consecutive daily doses). ISIS 353003 (SEQ ID NO: 267), a mixed backbone oligonucleotide which targets human PTP1B, was used as a control.

Male 9-week old Balb/c mice (Charles River Laboratories, Wilmington, Mass.) were given two, three, four or five intraperitoneal injections of ISIS 257016 or ISIS 353003 once a day for the treatment period. ISIS 257016 was administered at doses of 2.5 or 25 mg/kg and ISIS 353003 was administered at a dose of 25 mg/kg. Saline-injected animals served as controls. Each treatment group contained 4 mice. The mice were sacrificed 2 days following administration of the final dose of oligonucleotide or saline.

Mice were evaluated for SGLT2 levels in kidney. Target levels were determined by quantitative real-time PCR as described in other examples herein. PCR results were normalized to cyclophilin. The data are expressed as percent change relative to saline treated animals ("+" indicates an increase, "−" indicates a decrease) and are illustrated in Table 36.

TABLE 36

Antisense inhibition of SGLT2 mRNA expression in vivo by mixed backbone oligonucleotide (expressed as percent change in SGLT2 mRNA expression relative to saline control)

| Oligonucleotide (dose in mg/kg) | Two Doses | Three Doses | Four Doses | Five Doses |
|---|---|---|---|---|
| ISIS 257016 (2.5 mg/kg) | −14.2 | −35.4 | −25.3 | −42.0 |
| ISIS 257016 (25 mg/kg) | −12.5 | −32.9 | −39.1 | −68.9 |
| ISIS 353003 (25 mg/kg) | −4.5 | −9.6 | +0.5 | −11.3 |

These results illustrate that the mixed backbone compounds of the invention efficiently inhibit the expression of kidney SGLT2 and inhibition increases with the number of doses administered.

Treated mice were further evaluated for body weight, kidney weight, liver weight and spleen weight. The data are expressed as percent change in body or organ weight ("+" indicates an increase, "−" indicates a decrease). The results are presented in Tables 37-40.

TABLE 37

Effects of antisense compounds on total body weight of mice (expressed as percent change in body weight)

| Oligonucleotide (dose in mg/kg) | Two Doses | Three Doses | Four Doses | Five Doses |
|---|---|---|---|---|
| ISIS 257016 (2.5 mg/kg) | +2.7 | +2.7 | +3.2 | +1.5 |
| ISIS 257016 (25 mg/kg) | +2.0 | +2.0 | +3.1 | −0.7 |
| ISIS 353003 (25 mg/kg) | +0.6 | +0.8 | +2.5 | +1.3 |

TABLE 38

Effects of antisense compounds on total kidney weight (expressed as percent change in kidney weight)

| Oligonucleotide (dose in mg/kg) | Two Doses | Three Doses | Four Doses | Five Doses |
|---|---|---|---|---|
| ISIS 257016 (2.5 mg/kg) | +8.2 | −1.4 | +8.9 | +1.5 |
| ISIS 257016 (25 mg/kg) | +11.5 | +3.6 | +2.7 | −7.7 |
| ISIS 353003 (25 mg/kg) | +5.3 | −3.6 | +4.9 | +7.1 |

TABLE 39

Effects of antisense compounds on total liver weight (expressed as percent change in liver weight)

| Oligonucleotide (dose in mg/kg) | Two Doses | Three Doses | Four Doses | Five Doses |
|---|---|---|---|---|
| ISIS 257016 (2.5 mg/kg) | +9.2 | +7.5 | +4.8 | +4.8 |
| ISIS 257016 (25 mg/kg) | +11.8 | +5.2 | +0.6 | −8.0 |
| ISIS 353003 (25 mg/kg) | +7.4 | −3.4 | +12.9 | +9.5 |

TABLE 40

Effects of antisense compounds on total spleen weight (expressed as percent change in spleen weight)

| Oligonucleotide (dose in mg/kg) | Two Doses | Three Doses | Four Doses | Five Doses |
|---|---|---|---|---|
| ISIS 257016 (2.5 mg/kg) | +22.2 | +10.1 | +15.3 | +10.7 |
| ISIS 257016 (25 mg/kg) | +13.3 | +5.1 | +6.7 | +4.5 |
| ISIS 353003 (25 mg/kg) | +7.3 | +1.4 | +19.8 | +8.6 |

No significant change was observed in total body weight, kidney weight, liver weight or spleen weight at timepoints throughout or at the termination of the study.

Levels of creatinine, AST, ALT, albumin, triglycerides, cholesterol and glucose were measured in mice treated with the compounds of the invention. Plasma samples were analyzed using the Olympus AU400e automated chemistry analyzer (Olympus America, Irving, Tex.). The results, expressed as units measured, are shown in Tables 41-44.

TABLE 41

Effect of mixed backbone antisense compound ISIS 257016 administered as two consecutive daily doses on indicators of liver and kidney function

| | | Units measured per dose of oligonucleotide | | |
|---|---|---|---|---|
| Serum indicator | Normal Range | Saline | ISIS 257016 2.5 mg/kg | ISIS 257016 25 mg/kg | ISIS 353003 25 mg/kg |
| Creatinine mg/L | 0.0-1.0 | 0.2 | 0.1 | 0.1 | 0.2 |
| AST IU/L | 30-300 | 160 | 132 | 75 | 131 |
| ALT IU/L | 30-200 | 31 | 31 | 28 | 29 |
| Albumin g/dL | 2.5-4.0 | 2.8 | 2.9 | 3.0 | 2.7 |
| Triglycerides mg/dL | 25-100* | 233 | 238 | 287 | 240 |
| Cholesterol mg/dL | 70-125 | 113 | 117 | 122 | 106 |
| Glucose mg/dL | 80-150* | 171 | 195 | 175 | 164 |

TABLE 42

Effect of mixed backbone antisense compound ISIS 257016 administered as three consecutive daily doses on indicators of liver and kidney function

| | | Units measured per dose of oligonucleotide | | |
|---|---|---|---|---|
| Serum indicator | Normal Range | Saline | ISIS 257016 2.5 mg/kg | ISIS 257016 25 mg/kg | ISIS 353003 25 mg/kg |
| Creatinine mg/L | 0.0-1.0 | 0.1 | 0.2 | 0.2 | 0.1 |
| AST IU/L | 30-300 | 199 | 60 | 84 | 155 |
| ALT IU/L | 30-200 | 29 | 28 | 26 | 77 |
| Albumin g/dL | 2.5-4.0 | 2.8 | 2.9 | 2.8 | 2.9 |
| Triglycerides mg/dL | 25-100* | 289 | 268 | 259 | 236 |
| Cholesterol mg/dL | 70-125 | 111 | 118 | 108 | 106 |
| Glucose mg/dL | 80-150* | 204 | 162 | 181 | 179 |

TABLE 43

Effect of mixed backbone antisense compound ISIS 257016 administered as four consecutive daily doses on indicators of liver and kidney function

| | | Units measured per dose of oligonucleotide | | |
|---|---|---|---|---|
| Serum indicator | Normal Range | Saline | ISIS 257016 2.5 mg/kg | ISIS 257016 25 mg/kg | ISIS 353003 25 mg/kg |
| Creatinine mg/L | 0.0-1.0 | 0.1 | 0.1 | 0.1 | 0.2 |
| AST IU/L | 30-300 | 199 | 92 | 120 | 144 |
| ALT IU/L | 30-200 | 29 | 30 | 30 | 36 |
| Albumin g/dL | 2.5-4.0 | 2.8 | 3.0 | 2.8 | 3.0 |
| Triglycerides mg/dL | 25-100* | 289 | 252 | 269 | 294 |
| Cholesterol mg/dL | 70-125 | 111 | 126 | 115 | 120 |
| Glucose mg/dL | 80-150* | 204 | 173 | 198 | 192 |

TABLE 44

Effect of mixed backbone antisense compound ISIS 257016 administered as five consecutive daily doses on indicators of liver and kidney function

| | | Units measured per dose of oligonucleotide | | |
|---|---|---|---|---|
| Serum indicator | Normal Range | Saline | ISIS 257016 2.5 mg/kg | ISIS 257016 25 mg/kg | ISIS 353003 25 mg/kg |
| Creatinine mg/L | 0.0-1.0 | 0.1 | 0.1 | 0.1 | 0.1 |
| AST IU/L | 30-300 | 129 | 121 | 125 | 97 |
| ALT IU/L | 30-200 | 30 | 30 | 33 | 29 |
| Albumin g/dL | 2.5-4.0 | 2.8 | 2.9 | 2.8 | 2.9 |

TABLE 44-continued

Effect of mixed backbone antisense compound ISIS 257016 administered as five consecutive daily doses on indicators of liver and kidney function

| | | Units measured per dose of oligonucleotide | | | |
|---|---|---|---|---|---|
| Serum indicator | Normal Range | Saline | ISIS 257016 2.5 mg/kg | ISIS 257016 25 mg/kg | ISIS 353003 25 mg/kg |
| Triglycerides mg/dL | 25-100* | 298 | 298 | 285 | 277 |
| Cholesterol mg/dL | 70-125 | 116 | 126 | 122 | 126 |
| Glucose mg/dL | 80-150* | 163 | 177 | 204 | 185 |

*Triglyceride and glucose levels are routinely higher in the Balb/c strain of mice than in other strains of mice.

The levels of routine clinical indicators of liver and kidney injury and disease are within normal ranges and are not significantly changed relative to saline-treated animals, demonstrating that the compounds of the invention do not significantly affect renal or hepatic function. Triglyceride and glucose levels, while outside the normal range as is common in the Balb/c strain, are not significantly elevated relative to saline-treated animals.

The results illustrated in this example demonstrate that mixed backbone compounds are delivered to the kidney, reduce SGLT2 expression in vivo, and that treatment with these compounds does not result in liver or kidney toxicity. The results further indicate that inhibition of target mRNA expression in the kidney increases with the number of doses administered.

Example 27

Comparison of a Standard Mixed Backbone Compound and Mixed Backbone Compounds with Phosphorothioate Linkages at Either or Both of the Extreme 5' and 3' Ends: A Four Dose Protocol In accordance with the present invention, ISIS 257016 (SEQ ID NO: 106), ISIS 351641 (SEQ ID NO: 106), ISIS 360886 (SEQ ID NO: 106) and ISIS 360887 (SEQ ID NO: 106) were analyzed for their ability to inhibit SGLT2 expression in vivo. ISIS 257016 is a standard mixed backbone compound having 2'-MOE wings and a deoxy gap, with phosphodiester linkages in the wings and phosphorothioate linkages in the gap. ISIS 351641 differs from the standard mixed backbone compounds by having one phosphorothioate linkage at each of the extreme 5' and 3' ends of the wings. ISIS 360886 and ISIS 360887 are mixed backbone compounds with one phosphorothioate linkage at the extreme 5' end or extreme 3' end, respectively.

Male 7-week old Balb/c mice (Charles River Laboratories, Wilmington, Mass.) were given intraperitoneal injections of ISIS 257016, ISIS 351641, ISIS 360886 or ISIS 360887 twice a week for two weeks at doses of 1.56, 6.25 or 25 mg/kg. Saline-injected animals served as controls. Each treatment group contained 4 mice. The mice were sacrificed 2 days following administration of the final dose of oligonucleotide or saline.

Mice were evaluated for SGLT2 levels in kidney. Target levels were determined by quantitative real-time PCR as described in other examples herein. PCR results were normalized to cyclophilin. The data are expressed as percent change relative to saline treated animals ("+" indicates an increase, "−" indicates a decrease) and are illustrated in Table 45.

TABLE 45

Antisense inhibition of SGLT2 mRNA expression in vivo by mixed backbone oligonucleotides (expressed as percent change in SGLT2 mRNA expression relative to saline)

| Dose of oligonucleotide mg/kg | ISIS 257016 | ISIS 351641 | ISIS 360886 | ISIS 360887 |
|---|---|---|---|---|
| 1.56 | −39.1 | −4.2 | −12.7 | −9.7 |
| 6.25 | −52.8 | −4.87 | −19.7 | −7.3 |
| 25 | −57.8 | −11.0 | −29.0 | −4.9 |

These results illustrate that mixed backbone compounds of the invention, with either complete phosphodiester linkages in the wings, or with the extreme 5' and 3' ends substituted with phosphorothioate linkages, can inhibit the expression of kidney SGLT2 in a dose-dependent manner. With the exception of ISIS 360887, inhibition of target mRNA was dose-dependent. Although all mixed backbone compounds inhibited SGLT2 expression, greater inhibition is observed in kidneys from mice treated with ISIS 257016, which is a mixed backbone compound that contains all phosphodiester linkages in the wings.

Treated mice were further evaluated for body weight, kidney weight, liver weight and spleen weight. The data are expressed as percent change in body or organ weight ("+" indicates an increase, "−" indicates a decrease). The results are presented in Table 46.

TABLE 46

Effects of antisense compounds on total body weight, kidney weight, liver weight and spleen weight of mice (expressed as percent change in weight)

| Oligonucleotide | Dose mg/kg | Body weight | Kidney weight | Liver weight | Spleen weight |
|---|---|---|---|---|---|
| ISIS 257016 | 1.56 | +11.6 | −3.5 | −4.2 | −2.4 |
| ISIS 257016 | 6.25 | +7.9 | −3.0 | +3.8 | −1.3 |
| ISIS 257016 | 25 | +11.7 | −4.1 | +1.4 | +8.9 |
| ISIS 351641 | 1.56 | +7.9 | −0.9 | −5.4 | +9.4 |
| ISIS 351641 | 6.25 | +11.1 | +1.3 | −2.2 | +13.4 |
| ISIS 351641 | 25 | +7.4 | −2.1 | −0.5 | −1.4 |
| ISIS 360886 | 1.56 | +7.6 | −1.0 | −13.7 | −5.0 |
| ISIS 360886 | 6.25 | +8.9 | −3.7 | −16.6 | +1.2 |
| ISIS 360886 | 25 | +11.1 | −5.5 | −11.6 | +0.8 |
| ISIS 360887 | 1.56 | +8.5 | +1.0 | −10.4 | −0.4 |
| ISIS 360887 | 6.25 | +7.5 | −1.8 | −8.4 | +1.1 |
| ISIS 360887 | 25 | +9.8 | +2.2 | −9.0 | +11.8 |

No significant change was observed in total body weight, liver weight or spleen weight at timepoints throughout or at the termination of the study.

Levels of BUN, creatinine, bilirubin, AST, ALT, albumin, triglycerides, cholesterol and glucose were measured in mice treated with the compounds of the invention. Plasma samples were analyzed using the Olympus AU400e automated chemistry analyzer (Olympus America, Irving, Tex.). The results, expressed as units measured, are shown in Tables 47-50.

TABLE 47

Effect of mixed backbone antisense compound ISIS 257016 on indicators of liver and kidney function

| Serum indicator | Normal Range | Saline | Units measured per dose of ISIS 257016 | | |
| --- | --- | --- | --- | --- | --- |
| | | | 1.56 mg/kg | 6.25 mg/kg | 25 mg/kg |
| BUN mg/dL | 15-40 | 23 | 21 | 26 | 22 |
| Creatinine mg/L | 0.0-1.0 | 0.2 | 0.2 | 0.2 | 0.2 |
| Bilirubin mg/dL | 0.1-1.0 | 0.2 | 0.2 | 0.2 | 0.1 |
| AST IU/L | 30-300 | 75 | 61 | 83 | 71 |
| ALT IU/L | 30-200 | 30 | 30 | 33 | 39 |
| Albumin g/dL | 2.5-4.0 | 2.8 | 2.9 | 2.9 | 2.7 |
| Triglycerides mg/dL | 25-100* | 208 | 210 | 243 | 150 |
| Cholesterol mg/dL | 70-125 | 116 | 125 | 130 | 135 |
| Glucose mg/dL | 80-150* | 207 | 184 | 184 | 215 |

TABLE 48

Effect of mixed backbone antisense compound ISIS 351641 on indicators of liver and kidney function

| Serum indicator | Normal Range | Saline | Units measured per dose of ISIS 351641 | | |
| --- | --- | --- | --- | --- | --- |
| | | | 1.56 mg/kg | 6.25 mg/kg | 25 mg/kg |
| BUN mg/dL | 15-40 | 23 | 23 | 25 | 22 |
| Creatinine mg/L | 0.0-1.0 | 0.2 | 0.2 | 0.2 | 0.2 |
| Bilirubin mg/dL | 0.1-1.0 | 0.2 | 0.1 | 0.2 | 0.1 |
| AST IU/L | 30-300 | 75 | 61 | 67 | 54 |
| ALT IU/L | 30-200 | 30 | 32 | 31 | 30 |
| Albumin g/dL | 2.5-4.0 | 2.8 | 2.7 | 2.7 | 2.8 |
| Triglycerides mg/dL | 25-100* | 208 | 169 | 176 | 185 |
| Cholesterol mg/dL | 70-125 | 116 | 110 | 115 | 107 |
| Glucose mg/dL | 80-150* | 207 | 205 | 199 | 208 |

TABLE 49

Effect of mixed backbone antisense compound ISIS 360886 on indicators of liver and kidney function

| Serum indicator | Normal Range | Saline | Units measured per dose of ISIS 360886 | | |
| --- | --- | --- | --- | --- | --- |
| | | | 1.56 mg/kg | 6.25 mg/kg | 25 mg/kg |
| BUN mg/dL | 15-40 | 23 | 21 | 23 | 24 |
| Creatinine mg/L | 0.0-1.0 | 0.2 | 0.1 | 0.2 | 0.2 |
| Bilirubin mg/dL | 0.1-1.0 | 0.2 | 0.2 | 0.2 | 0.1 |
| AST IU/L | 30-300 | 75 | 56 | 77 | 73 |
| ALT IU/L | 30-200 | 30 | 26 | 27 | 28 |
| Albumin g/dL | 2.5-4.0 | 2.8 | 2.7 | 2.7 | 2.7 |
| Triglycerides mg/dL | 25-100* | 208 | 164 | 181 | 169 |
| Cholesterol mg/dL | 70-125 | 116 | 105 | 108 | 108 |
| Glucose mg/dL | 80-150* | 207 | 189 | 202 | 200 |

TABLE 50

Effect of mixed backbone antisense compound ISIS 360887 on indicators of liver and kidney function

| Serum indicator | Normal Range | Saline | Units measured per dose of ISIS 360887 | | |
| --- | --- | --- | --- | --- | --- |
| | | | 1.56 mg/kg | 6.25 mg/kg | 25 mg/kg |
| BUN mg/dL | 15-40 | 23 | 23 | 22 | 23 |
| Creatinine mg/L | 0.0-1.0 | 0.2 | 0.2 | 0.2 | 0.2 |
| Bilirubin mg/dL | 0.1-1.0 | 0.2 | 0.2 | 0.1 | 0.2 |
| AST IU/L | 30-300 | 75 | 142 | 83 | 108 |
| ALT IU/L | 30-200 | 30 | 40 | 39 | 34 |
| Albumin g/dL | 2.5-4.0 | 2.8 | 2.7 | 2.7 | 2.7 |
| Triglycerides mg/dL | 25-100* | 208 | 136 | 157 | 200 |
| Cholesterol mg/dL | 70-125 | 116 | 109 | 107 | 110 |
| Glucose mg/dL | 80-150* | 207 | 199 | 201 | 187 |

*Triglyceride and glucose levels are routinely higher in the Balb/c strain of mice than in other strains of mice.

Cholesterol levels of mice treated with either 6.25 or 25 mg/kg were slightly elevated; however, these levels are not significantly greater than the cholesterol levels observed in saline-treated control animals. Otherwise, the levels of routine clinical indicators of liver and kidney injury and disease are within normal ranges and are not significantly changed relative to saline-treated animals, demonstrating that the compounds of the invention do not significantly affect renal or hepatic function. Triglyceride and glucose levels, while outside the normal range as is common in the Balb/c strain, are not significantly elevated relative to saline-treated animals.

Saline- and oligonucleotide-injected animals also were evaluated histologically following routine procedures. Liver and kidney samples were procured, fixed in 10% neutral-buffered formalin and processed for staining with hematoxylin and eosin. Hematoxylin and eosin staining exhibited no significant difference between control and oligonucleotide-treated animals.

The results illustrated in this example demonstrate that mixed backbone compounds are delivered to the kidney, reduce SGLT2 expression in vivo, and that treatment with these compounds does not result in liver or kidney toxicity. The results further indicate that mixed backbone compounds with complete phosphodiester linkages in the wings are more effective modulators of target mRNA expression in the kidney than mixed backbone compounds with a phosphorothioate linkage at one or both of the extreme 5' and 3' ends.

Example 28

Comparison of a Standard Mixed Backbone Compound and Mixed Backbone Compounds with Phosphorothioate Linkages at Either or Both of the Extreme 5' and 3' Ends: An Eight Dose Protocol A second study of SGLT2 antisense oligonucleotides ISIS 257016, ISIS 351641, ISIS 360886 and ISIS 360887 was undertaken in which mice received eight doses over a four week period. As described previously, ISIS 257016 is a standard mixed backbone compound having 2'-MOE wings and a deoxy gap, with phosphodiester linkages in the wings and phosphorothioate linkages in the gap. ISIS 351641 differs from the standard mixed backbone compounds by having one phosphorothioate linkage at each of the extreme 5' and 3' ends of the wings. ISIS 360886 and ISIS 360887 are mixed backbone compounds with one phosphorothioate linkage at the extreme 5' end and extreme 3' end, respectively.

Male 8-week old Balb/c mice (Charles River Laboratories, Wilmington, Mass.) were given intraperitoneal injections of ISIS 257016, ISIS 351641, ISIS 360886 or ISIS 360887 twice a week for four weeks at doses of 1, 5 or 25 mg/kg. Saline-injected animals served as controls. Each treatment group contained 4 mice. The mice were sacrificed 2 days following administration of the final dose of oligonucleotide or saline.

Mice were evaluated for SGLT2 levels in kidney. Target levels were determined by quantitative real-time PCR as described by other examples herein. PCR results were normalized to cyclophilin. The data are expressed as percent change relative to saline treated animals ("+" indicates an increase, "−" indicates a decrease) and are illustrated in Table 51.

TABLE 51

Antisense inhibition of SGLT2 mRNA expression in vivo by mixed backbone oligonucleotides (expressed as percent change in SGLT2 mRNA expression relative to saline)

| Dose of oligonucleotide mg/kg | ISIS 257016 | ISIS 351641 | ISIS 360886 | ISIS 360887 |
|---|---|---|---|---|
| 1 | −53 | −14 | −24 | −23 |
| 5 | −64 | −23 | −30 | −26 |
| 25 | −68 | −37 | −50 | −40 |

These results illustrate that mixed backbone compounds of the invention, with either complete phosphodiester linkages in the wings, or with the extreme 5' and 3' ends substituted with phosphorothioate linkages, can inhibit the expression of kidney SGLT2 in a dose-dependent manner. However, greater inhibition is observed in kidneys from mice treated with ISIS 257016, which contains all phosphodiester linkages in the wings.

Treated mice were further evaluated for body weight and liver and spleen weight. The data are expressed as percent change in body or organ weight ("+" indicates an increase, "−" indicates a decrease). The results are presented in Table 52.

TABLE 52

Effects of antisense compounds on total body weight, liver weight and spleen weight of mice (expressed as percent change in weight)

| Oligonucleotide | Dose mg/kg | Body weight | Liver weight | Spleen weight |
|---|---|---|---|---|
| ISIS 257016 | 1 | +11.8 | −6.9 | −10.1 |
| ISIS 257016 | 5 | +8.4 | −4.3 | +4.4 |
| ISIS 257016 | 25 | +5.4 | −2.1 | +12.5 |
| ISIS 351641 | 1 | +12.3 | −2.8 | −2.9 |
| ISIS 351641 | 5 | +9.2 | −8.7 | −5.5 |
| ISIS 351641 | 25 | +9.4 | −0.8 | +3.3 |
| ISIS 360886 | 1 | +9.2 | −5.2 | −4.5 |
| ISIS 360886 | 5 | +10.3 | −2.7 | +15.1 |
| ISIS 360886 | 25 | +9.4 | −2.1 | −11.4 |
| ISIS 360887 | 1 | +10.0 | −7.0 | −1.5 |
| ISIS 360887 | 5 | +12.6 | −3.2 | +4.0 |
| ISIS 360887 | 25 | +11.8 | −7.6 | +14.7 |

No significant change was observed in total body weight, liver weight or spleen weight at timepoints throughout or at the termination of the study.

Levels of BUN, creatinine, bilirubin, AST, ALT, albumin, triglycerides, cholesterol and glucose were measured in mice treated with the compounds of the invention. Plasma samples were analyzed using the Olympus AU400e automated chemistry analyzer (Olympus America, Irving, Tex.). The results, expressed as units measured, are shown in Tables 53-56.

TABLE 53

Effect of mixed backbone antisense compound ISIS 257016 on indicators of liver and kidney function

| | Normal | Units measured per dose of ISIS 257016 | | |
|---|---|---|---|---|
| Serum indicator | Range | Saline | 1 mg/kg | 5 mg/kg | 25 mg/kg |
| BUN mg/dL | 15-40 | 27 | 31 | 29 | 23 |
| Creatinine mg/L | 0.0-1.0 | 0.2 | 0.2 | 0.2 | 0.2 |
| Bilirubin mg/dL | 0.1-1.0 | 0.2 | 0.2 | 0.2 | 0.2 |
| AST IU/L | 30-300 | 60 | 58 | 82 | 119 |
| ALT IU/L | 30-200 | 22 | 27 | 35 | 66 |
| Albumin g/dL | 2.5-4.0 | 2.7 | 2.8 | 2.7 | 2.6 |
| Triglycerides mg/dL | 25-100* | 178 | 263 | 187 | 99 |
| Cholesterol mg/dL | 70-125 | 123 | 142 | 138 | 162 |
| Glucose mg/dL | 80-150* | 193 | 201 | 201 | 185 |

TABLE 54

Effect of mixed backbone antisense compound ISIS 351641 on indicators of liver and kidney function

| | Normal | Units measured per dose of ISIS 351641 | | |
|---|---|---|---|---|
| Serum indicator | Range | Saline | 1 mg/kg | 5 mg/kg | 25 mg/kg |
| BUN mg/dL | 15-40 | 27 | 27 | 26 | 28 |
| Creatinine mg/L | 0.0-1.0 | 0.2 | 0.2 | 0.2 | 0.2 |
| Bilirubin mg/dL | 0.1-1.0 | 0.2 | 0.1 | 0 | 0.1 |
| AST IU/L | 30-300 | 60 | 48 | 49 | 50 |

TABLE 54-continued

Effect of mixed backbone antisense compound ISIS 351641 on indicators of liver and kidney function

| Serum indicator | Normal Range | Units measured per dose of ISIS 351641 | | | |
|---|---|---|---|---|---|
| | | Saline | 1 mg/kg | 5 mg/kg | 25 mg/kg |
| ALT IU/L | 30-200 | 22 | 23 | 23 | 20 |
| Albumin g/dL | 2.5-4.0 | 2.7 | 2.8 | 2.8 | 2.7 |
| Triglycerides mg/dL | 25-100* | 178 | 165 | 197 | 222 |
| Cholesterol mg/dL | 70-125 | 123 | 118 | 120 | 118 |
| Glucose mg/dL | 80-150* | 193 | 192 | 200 | 197 |

TABLE 55

Effect of mixed backbone antisense compound ISIS 360886 on indicators of liver and kidney function

| Serum indicator | Normal Range | Units measured per dose of ISIS 360886 | | | |
|---|---|---|---|---|---|
| | | Saline | 1 mg/kg | 5 mg/kg | 25 mg/kg |
| BUN mg/dL | 15-40 | 27 | 27 | 26 | 27 |
| Creatinine mg/L | 0.0-1.0 | 0.2 | 0.2 | 0.2 | 0.2 |
| Bilirubin mg/dL | 0.1-1.0 | 0.2 | 0 | 0.1 | 0.1 |
| AST IU/L | 30-300 | 60 | 52 | 71 | 90 |
| ALT IU/L | 30-200 | 22 | 23 | 23 | 29 |
| Albumin g/dL | 2.5-4.0 | 2.7 | 2.8 | 2.8 | 2.8 |
| Triglycerides mg/dL | 25-100* | 178 | 230 | 250 | 227 |
| Cholesterol mg/dL | 70-125 | 123 | 122 | 129 | 133 |
| Glucose mg/dL | 80-150* | 193 | 187 | 182 | 185 |

TABLE 56

Effect of mixed backbone antisense compound ISIS 360887 on indicators of liver and kidney function

| Serum indicator | Normal Range | Units measured per dose of ISIS 360887 | | | |
|---|---|---|---|---|---|
| | | Saline | 1 mg/kg | 5 mg/kg | 25 mg/kg |
| BUN mg/dL | 15-40 | 27 | 25 | 24 | 23 |
| Creatinine mg/L | 0.0-1.0 | 0.2 | 0.2 | 0.2 | 0.1 |
| Bilirubin mg/dL | 0.1-1.0 | 0.2 | 0.2 | 0.2 | 0.2 |
| AST IU/L | 30-300 | 60 | 60 | 44 | 92 |
| ALT IU/L | 30-200 | 22 | 24 | 22 | 31 |
| Albumin g/dL | 2.5-4.0 | 2.7 | 2.7 | 2.5 | 2.7 |
| Triglycerides mg/dL | 25-100* | 178 | 240 | 262 | 171 |

TABLE 56-continued

Effect of mixed backbone antisense compound ISIS 360887 on indicators of liver and kidney function

| Serum indicator | Normal Range | Units measured per dose of ISIS 360887 | | | |
|---|---|---|---|---|---|
| | | Saline | 1 mg/kg | 5 mg/kg | 25 mg/kg |
| Cholesterol mg/dL | 70-125 | 123 | 121 | 129 | 134 |
| Glucose mg/dL | 80-150* | 193 | 189 | 186 | 181 |

*Triglyceride and glucose levels are routinely higher in the Balb/c strain of mice than in other strains of mice.

The levels of routine clinical indicators of liver and kidney injury and disease are within normal ranges and are not significantly changed relative to saline-treated animals, demonstrating that the compounds of the invention do not significantly affect renal or hepatic function. Triglyceride and glucose levels, while outside the normal range as is common in the Balb/c strain, are not significantly elevated relative to saline-treated animals.

The results illustrated in this example demonstrate that mixed backbone compounds are delivered to the kidney, reduce SGLT2 expression in vivo, and that treatment with these compounds does not result in liver or kidney toxicity. Furthermore, the eight dose protocol resulted in greater inhibition of target mRNA levels in the kidney than observed for the four dose protocol shown in Example 22.

Example 29

Antisense Inhibition of SGLT2 in a Murine Model of Type 2 Diabetes: Comparison of Full Phosphorothioate and Mixed Backbone Oligonucleotides The Animal Models of Diabetic Complications Consortium (AMDCC) has developed protocols for the induction of diabetes in a number of animal models. The genetic C57BLKS/J Lep$^{db}$/Lep$^{db}$ model has been approved by the AMDCC as an appropriate model system for studies of diabetic nephropathy associated with type 2 diabetes.

Leptin is a hormone produced by fat that regulates appetite. Deficiencies in this hormone in both humans and non-human animals lead to obesity. Lep$^{db}$/Lep$^{db}$ mice have a mutation in the leptin receptor gene which results in obesity and hyperglycemia. As such, these mice are a useful model for the investigation of obesity and diabetes and treatments designed to treat these conditions. In accordance with the present invention, oligomeric compounds of the present invention were tested in the Lep$^{db}$/Lep$^{db}$ model of type 2 diabetes.

Male Lep$^{db}$/Lep$^{db}$ (db/db) mice were given intraperitoneal injections of either ISIS 257016 (SEQ ID NO: 106), which has a mixed backbone, or ISIS 145733 (SEQ ID NO: 106), which has a phosphorothioate backbone, twice a week for four weeks at doses of 12.5, 25 or 37.5 mg/kg. Saline-injected animals served as controls. Each treatment group contained 6 mice. The mice were sacrificed 2 days following administration of the final dose of oligonucleotide or saline.

Mice were evaluated for SGLT2 levels in kidney. Target levels were determined by quantitative real-time PCR as described by other examples herein. PCR results were normalized to cyclophilin. The data are expressed as percent change relative to saline treated animals ("+" indicates an increase, "−" indicates a decrease) and are illustrated in Table 57.

TABLE 57

Antisense inhibition of SGLT2 mRNA expression in db/db
mice (expressed as percent change in SGLT2 mRNA expression
relative to saline)

| Dose of oligonucleotide mg/kg | ISIS 145733 | ISIS 257016 |
|---|---|---|
| 12.5 | −48 | −72 |
| 25 | −71 | −72 |
| 37.5 | −64 | −72 |

These results illustrate that both mixed backbone compound ISIS 257016 and full phosphorothioate compound ISIS 145733 effectively inhibit the expression of kidney SGLT2. However, greater inhibition is observed in kidneys from mice treated with ISIS 257016, particularly at the lowest dose of 12.5 mg/kg.

Treated mice were further evaluated for body weight and liver and spleen weight. The data are expressed as weight in grams. The results are presented in Table 58.

TABLE 58

Effects of antisense compounds on total body weight, liver weight and
spleen weight of db/db mice (in grams)

| Oligonucleotide | Dose mg/kg | Body weight | Kidney weight | Liver weight | Spleen weight |
|---|---|---|---|---|---|
| Saline | — | 35 | 0.32 | 1.5 | 0.09 |
| ISIS 145733 | 12.5 | 34 | 0.32 | 1.9 | 0.12 |
| ISIS 145733 | 25 | 37 | 0.37 | 2.1 | 0.15 |
| ISIS 145733 | 37.5 | 38 | 0.35 | 2.3 | 0.14 |
| ISIS 257016 | 12.5 | 34 | 0.31 | 1.6 | 0.09 |
| ISIS 257016 | 25 | 36 | 0.31 | 1.7 | 0.08 |
| ISIS 257016 | 37.5 | 34 | 0.35 | 1.8 | 0.11 |

No significant change was observed in total body weight, liver weight or spleen weight at timepoints throughout or at the termination of the study.

Levels of AST, ALT, triglycerides, cholesterol and glucose were measured in mice treated with the compounds of the invention. Plasma samples were analyzed using the Olympus AU400e automated chemistry analyzer (Olympus America, Irving, Tex.). The results, expressed as units measured, are shown in Table 59 and Table 60.

TABLE 59

Effect of full phosphorothioate backbone compound ISIS 145733 on
indicators of toxicity

| Serum indicator | Normal Range | Units measured per dose of ISIS 145733 | | |
|---|---|---|---|---|
| | | Saline | 12.5 mg/kg | 25 mg/kg | 37.5 mg/kg |
| AST IU/L | 30-300 | 61 | 72 | 80 | 93 |
| ALT IU/L | 30-200 | 63 | 87 | 101 | 120 |
| Triglycerides mg/dL | 25-100* | 245 | 216 | 243 | 204 |
| Cholesterol mg/dL | 70-125* | 182 | 196 | 211 | 224 |
| Glucose mg/dL | 80-150* | 611 | 452 | 391 | 351 |

TABLE 60

Effect of mixed backbone antisense compound ISIS 257016
on indicators of toxicity

| Serum indicator | Normal Range | Units measured per dose of ISIS 257016 | | |
|---|---|---|---|---|
| | | Saline | 12.5 mg/kg | 25 mg/kg | 37.5 mg/kg |
| AST IU/L | 30-300 | 61 | 120 | 144 | 175 |
| ALT IU/L | 30-200 | 63 | 123 | 142 | 154 |
| Triglycerides mg/dL | 25-100* | 245 | 167 | 188 | 183 |
| Cholesterol mg/dL | 70-125* | 182 | 248 | 264 | 265 |
| Glucose mg/dL | 80-150* | 611 | 281 | 320 | 326 |

*Triglyceride, cholesterol and glucose levels are routinely higher in the $Lep^{db}/Lep^{db}$ strain of mice than in other strains of mice.

The levels of routine clinical indicators of liver injury and disease are within normal ranges and are not significantly changed relative to saline-treated animals, demonstrating that the compounds of the invention do not significantly affect hepatic function. Given the genetic defect of the $Lep^{db}/Lep^{db}$ mice and the diabetic phenotype exhibited by these mice, it is expected that triglyceride, cholesterol and glucose levels will exceed the normal range. Importantly, treatment with either of the SGLT2 antisense compounds resulted in a significant decrease in blood glucose levels, with ISIS 257016, the mixed backbone compound, achieving greater levels of target mRNA inhibition. Treatment with ISIS 257016 also resulted in a significant decrease in serum triglyceride levels.

The results illustrated in this example demonstrate that mixed backbone compounds are effectively delivered to the kidney, reduce SGLT2 expression in vivo, and that treatment with these compounds does not result in liver or other toxicity. Furthermore, these results indicate that mixed backbone compounds targeted to SGLT2 efficiently decrease blood glucose levels and serum triglyceride levels in a mouse model of type 2 diabetes.

Example 30

Antisense Inhibition of SGLT2 in a Murine Model of Type 2 Diabetes: Low Dose Comparison of Full Phosphorothioate and Mixed Backbone Oligonucleotides Since treatment with ISIS 257016 resulted in significant reduction in SGLT2 expression levels even at the lowest dose of 12.5 mg/kg, a second dose-response study was conducted using a lower dose range of 1.56, 3.12 and 6.25 mg/kg. Male $Lep^{db}/Lep^{db}$ mice were given intraperitoneal injections of either mixed backbone compound ISIS 257016 or full phosphorothioate compound ISIS 145733 twice a week for four weeks at doses of 1.56, 3.12 or 6.25 mg/kg. Saline-injected animals served as controls. Each treatment group contained 4 mice. The mice were sacrificed 2 days following administration of the final dose of oligonucleotide or saline.

Mice were evaluated for SGLT2 levels in kidney. Target levels were determined by quantitative real-time PCR as described by other examples herein. PCR results were normalized to cyclophilin. The data are expressed as percent change relative to saline treated animals ("+" indicates an increase, "−" indicates a decrease) and are illustrated in Table 61.

TABLE 61

Antisense inhibition of SGLT2 mRNA expression in db/db mice (expressed as percent change in SGLT2 mRNA expression relative to saline)

| Dose of oligonucleotide mg/kg | ISIS 145733 | ISIS 257016 |
|---|---|---|
| 1.56 | −13 | −75 |
| 3.12 | −14 | −83 |
| 6.25 | −12 | −80 |

These results illustrate that mixed backbone compound ISIS 257016 is a more effective inhibitor of SGLT2 mRNA expression in the kidney, particularly at low doses of oligonucleotide.

Levels of glucose were measured in mice treated with the compounds of the invention. Plasma samples were analyzed using the Olympus AU400e automated chemistry analyzer (Olympus America, Irving, Tex.). The data are expressed as percent change relative to saline treated animals ("+" indicates an increase, "−" indicates a decrease) and are illustrated in Table 62.

TABLE 62

Blood glucose levels in db/db mice treated with SGLT2 antisense compounds (expressed as percent change in blood glucose relative to saline)

| Dose of oligonucleotide mg/kg | ISIS 145733 | ISIS 257016 |
|---|---|---|
| 1.56 | −5 | −41 |
| 3.12 | −7 | −37 |
| 6.25 | −14 | −40 |

The results demonstrate that treatment with mixed backbone compound ISIS 257016 results in a significant decrease in blood glucose levels and that mixed backbone compounds are more effective at lowering blood glucose levels than full phosphorothioate antisense compounds.

Antisense inhibition of SGLT2 by ISIS 257016 was further evaluated using a dose range of 0.39, 0.78 and 1.56 mg/kg. As described above, male $Lep^{db}/Lep^{db}$ mice were given intraperitoneal injections of mixed backbone compound ISIS 257016 twice a week for four weeks. Saline-injected animals served as controls. Each treatment group contained 4 mice. The mice were sacrificed 2 days following administration of the final dose of oligonucleotide or saline.

Mice were evaluated for SGLT2 levels in kidney. Target levels were determined by quantitative real-time PCR as described by other examples herein. PCR results were normalized to cyclophilin. Blood glucose levels also were determined. Plasma samples were analyzed using the Olympus AU400e automated chemistry analyzer (Olympus America, Irving, Tex.). The data are expressed as percent change relative to saline treated animals ("+" indicates an increase, "−" indicates a decrease) and are illustrated in Table 63.

TABLE 63

Antisense inhibition of SGLT2 mRNA expression and blood glucose levels in db/db mice (expressed as percent change in SGLT2 mRNA expression or blood glucose levels relative to saline)

| Dose of ISIS 257016 mg/kg | SGLT2 mRNA | Blood glucose |
|---|---|---|
| 0.39 | −66 | −16 |
| 0.78 | −68 | −21 |
| 1.56 | −82 | −21 |

These results further demonstrate the effectiveness of mixed backbone compounds at inhibiting SGLT2 expression in the kidney and lowering blood glucose levels when administered at very low doses of oligonucleotide.

Mice treated with the compounds of the invention also were evaluated for liver and kidney toxicity, organ and body weights and tissue histology. These studies demonstrated no significant level of toxicity or change in body or organ weight, indicating that mixed backbone compounds are effective in vivo without toxicity to the animal.

The results illustrated in this example demonstrate that mixed backbone compounds are effectively delivered to the kidney, reduce SGLT2 expression in vivo, and that treatment with these compounds lowers blood glucose levels in diabetic animals.

Example 31

Antisense Inhibition of SGLT2 in a Murine Model of Obesity and Diabetes Using Mixed Backbone Compounds Leptin is a hormone produced by fat that regulates appetite. Deficiencies in this hormone in both humans and non-human animals leads to obesity. C57B1/6J-Lep ob/ob mice have a mutation in the leptin gene which results in obesity and hyperglycemia. As such, these mice are a useful model for the investigation of obesity and diabetes and treatments designed to treat these conditions. In accordance with the present invention, the oligomeric compounds of the invention were tested in the ob/ob model of obesity and diabetes.

Male C57B1/6J-Lep ob/ob mice (Jackson Laboratory, Bar Harbor, Me.) were subcutaneously injected with ISIS 257016 (SEQ ID NO: 106) at a dose of 25 mg/kg two times per week for 4 weeks. Saline-injected animals served as controls. Each treatment group contained 4 mice. The mice were sacrificed 2 days following administration of the final dose of oligonucleotide or saline.

Mice were evaluated for SGLT2 levels in kidney. Target levels were determined by quantitative real-time PCR as described by other examples herein. PCR results were normalized to cyclophilin. Blood glucose levels also were determined. Plasma samples were analyzed using the Olympus AU400e automated chemistry analyzer (Olympus America, Irving, Tex.). The data are expressed as percent change relative to saline treated animals ("+" indicates an increase, "−" indicates a decrease) and are illustrated in Table 64.

TABLE 64

Antisense inhibition of SGLT2 mRNA expression and blood
glucose levels in ob/ob mice (expressed as percent change in
SGLT2 mRNA expression or blood glucose levels relative
to saline)

| Dose of oligonucleotide mg/kg | SGLT2 mRNA | Blood glucose |
|---|---|---|
| 25 | −83 | −39 |

The results demonstrate that treatment with a mixed backbone SGLT2 antisense compound results in a significant decrease in SGLT2 mRNA expression in the kidney of diabetic mice. Importantly, blood glucose levels also are significantly decreased in treated animals.

Example 32

Comparison of Mixed Backbone Compounds 16 to 20 Nucleobases in Length

In accordance with the present invention, mixed backbone compounds with less than 20 nucleobases were evaluated for their ability to inhibit SGLT2 expression in the kidney. Four compounds were synthesized based on the sequence of ISIS 257016 (SEQ ID NO: 106). ISIS 366847, ISIS 366848, ISIS 366849 and ISIS 366850 are comprised of the 5'-most 19, 18, 17 and 16 nucleobases, respectively, of ISIS 257016 (see Table 65). ISIS 257016 has 2'-MOE wings of five nucleobases each and a deoxy gap of 10 nucleobases. ISIS 366847, ISIS 366848, ISIS 366849 and ISIS 366850 have a 10 nucleobases gap, a five nucleobase 2'-MOE wing at the 5' end, but contain a shortened 3' wing of 1 to 4 nucleobases.

TABLE 65

Antisense compounds 16 to 20 nucleobases in length

| ISIS # | SEQUENCE | SEQ ID NO: |
|---|---|---|
| 257016 | GAAGTAGCCACCAACTGTGC | 106 |
| 366847 | GAAGTAGCCACCAACTGTG | 272 |
| 366848 | GAAGTAGCCACCAACTGT | 273 |
| 366849 | GAAGTAGCCACCAACTG | 274 |
| 366850 | GAAGTAGCCACCAACT | 275 |

Male 6-week old Balb/c mice (Charles River Laboratories, Wilmington, Mass.) were given intraperitoneal injections of ISIS 257016, ISIS 366847, ISIS 366848, ISIS 366849 or ISIS 366850 twice a week for two weeks at doses of 0.14, 0.7 or 3.5 micromoles per kilogram (μM/kg). Saline-injected animals served as controls. Each treatment group contained 4 mice. The mice were sacrificed 2 days following administration of the final dose of oligonucleotide or saline.

Mice were evaluated for SGLT2 levels in kidney. Target levels were determined by quantitative real-time PCR as described in other examples herein. PCR results were normalized to cyclophilin. The data are expressed as percent change relative to saline treated animals ("+" indicates an increase, "−" indicates a decrease) and are illustrated in Table 66.

TABLE 66

Antisense inhibition of SGLT2 mRNA expression in vivo
by mixed backbone oligonucleotides (expressed as
percent change relative to saline control)

| Dose of oligonucleotide μM/kg | ISIS 257016 | ISIS 366847 | ISIS 366848 | ISIS 366849 | ISIS 366850 |
|---|---|---|---|---|---|
| 0.14 | −53 | −55 | −58 | −57 | −49 |
| 0.7 | −56 | −63 | −59 | −61 | −57 |
| 3.5 | −70 | −64 | −72 | −69 | −69 |

These results illustrate that mixed backbone compounds of the invention, containing 16 to 20 nucleobases, are effective inhibitors of SGLT2 expression in the kidney.

Treated mice were further evaluated for body weight, kidney weight, liver weight and spleen weight. The data are expressed as percent change in body or organ weight ("+" indicates an increase, "−" indicates a decrease). The results are presented in Table 67.

TABLE 67

Effects of antisense compounds on total body weight,
kidney weight, liver weight and spleen weight of mice
(expressed as percent change in weight)

| Oligonucleotide | Dose μM/kg | Body weight | Kidney weight | Liver weight | Spleen weight |
|---|---|---|---|---|---|
| ISIS 257016 | 0.14 | +9.0 | −4.5 | −6.1 | −8.3 |
| ISIS 257016 | 0.7 | +11.1 | −5.3 | +4.1 | −3.7 |
| ISIS 257016 | 3.5 | +10.2 | −3.6 | +3.7 | +11.9 |
| ISIS 366847 | 0.14 | +15.0 | −0.5 | +0.2 | −6.9 |
| ISIS 366847 | 0.7 | +12.7 | +1.2 | +6.8 | −4.9 |
| ISIS 366847 | 3.5 | +10.3 | +3.6 | +3.8 | +2.9 |
| ISIS 366848 | 0.17 | +8.5 | −7.1 | −7.9 | −2.4 |
| ISIS 366848 | 0.7 | +7.7 | +6.4 | +5.9 | +3.8 |
| ISIS 366848 | 3.5 | +10.8 | +3.0 | +4.6 | +9.3 |
| ISIS 366849 | 0.14 | +6.9 | −3.3 | −2.6 | −7.2 |
| ISIS 366849 | 0.7 | +7.4 | +0.1 | −4.3 | −2.2 |
| ISIS 366849 | 3.5 | +8.4 | −2.9 | −5.2 | −3.9 |
| ISIS 366850 | 0.14 | +11.1 | −3.8 | −4.6 | +2.0 |
| ISIS 366850 | 0.7 | +4.8 | −0.8 | −1.7 | +0.9 |
| ISIS 366850 | 3.5 | 11.2 | −6.0 | +4.5 | +9.8 |

No significant change was observed in total body weight, liver weight or spleen weight at timepoints throughout or at the termination of the study.

Levels of BUN, creatinine, bilirubin, AST, ALT, albumin, triglycerides, cholesterol and glucose were measured in mice treated with the compounds of the invention. Plasma samples were analyzed using the Olympus AU400e automated chemistry analyzer (Olympus America, Irving, Tex.). The results, expressed as units measured, are shown in Tables 68-72.

TABLE 68

Effect of mixed backbone antisense compound ISIS 257016 on indicators
of liver and kidney function

| | | Units measured per dose of ISIS 257016 | | | |
|---|---|---|---|---|---|
| Serum indicator | Normal Range | Saline | 0.14 μM/kg | 0.7 μM/kg | 3.5 μM/kg |
| BUN mg/dL | 15-40 | 31 | 32 | 32 | 31 |
| Creatinine mg/L | 0.0-1.0 | 0.2 | 0.2 | 0.2 | 0.2 |

TABLE 68-continued

Effect of mixed backbone antisense compound ISIS 257016 on indicators of liver and kidney function

| Serum indicator | Normal Range | Units measured per dose of ISIS 257016 | | | |
|---|---|---|---|---|---|
| | | Saline | 0.14 µM/kg | 0.7 µM/kg | 3.5 µM/kg |
| Bilirubin mg/dL | 0.1-1.0 | 0.2 | 0.1 | 0.1 | 0.1 |
| AST IU/L | 30-300 | 82 | 68 | 85 | 117 |
| ALT IU/L | 30-200 | 22 | 24 | 26 | 32 |
| Albumin g/dL | 2.5-4.0 | 3.0 | 3.2 | 3.1 | 3.1 |
| Triglycerides mg/dL | 25-100* | 225 | 266 | 308 | 225 |
| Cholesterol mg/dL | 70-125 | 123 | 128 | 128 | 147 |
| Glucose mg/dL | 80-150* | 181 | 195 | 187 | 183 |

TABLE 69

Effect of mixed backbone antisense compound ISIS 366847 on indicators of liver and kidney function

| Serum indicator | Normal Range | Units measured per dose of ISIS 366847 | | | |
|---|---|---|---|---|---|
| | | Saline | 0.14 µM/kg | 0.7 µM/kg | 3.5 µM/kg |
| BUN mg/dL | 15-40 | 31 | 29 | 32 | 29 |
| Creatinine mg/L | 0.0-1.0 | 0.2 | 0.2 | 0.2 | 0.2 |
| Bilirubin mg/dL | 0.1-1.0 | 0.2 | 0.1 | 0 | 0.1 |
| AST IU/L | 30-300 | 82 | 53 | 69 | 131 |
| ALT IU/L | 30-200 | 22 | 23 | 28 | 50 |
| Albumin g/dL | 2.5-4.0 | 3.0 | 3.1 | 3.2 | 3.0 |
| Triglycerides mg/dL | 25-100* | 225 | 289 | 308 | 184 |
| Cholesterol mg/dL | 70-125 | 123 | 122 | 132 | 145 |
| Glucose mg/dL | 80-150* | 181 | 173 | 193 | 181 |

TABLE 70

Effect of mixed backbone antisense compound ISIS 366848 on indicators of liver and kidney function

| Serum indicator | Normal Range | Units measured per dose of ISIS 366848 | | | |
|---|---|---|---|---|---|
| | | Saline | 0.14 µM/kg | 0.7 µM/kg | 3.5 µM/kg |
| BUN mg/dL | 15-40 | 31 | 31 | 29 | 32 |
| Creatinine mg/L | 0.0-1.0 | 0.2 | 0.2 | 0.2 | 0.2 |
| Bilirubin mg/dL | 0.1-1.0 | 0.2 | 0.1 | 0.1 | 0.1 |
| AST IU/L | 30-300 | 82 | 82 | 105 | 123 |
| ALT IU/L | 30-200 | 22 | 23 | 34 | 46 |
| Albumin g/dL | 2.5-4.0 | 3.0 | 3.1 | 3.1 | 3.0 |

TABLE 70-continued

Effect of mixed backbone antisense compound ISIS 366848 on indicators of liver and kidney function

| Serum indicator | Normal Range | Units measured per dose of ISIS 366848 | | | |
|---|---|---|---|---|---|
| | | Saline | 0.14 µM/kg | 0.7 µM/kg | 3.5 µM/kg |
| Triglycerides mg/dL | 25-100* | 225 | 320 | 374 | 246 |
| Cholesterol mg/dL | 70-125 | 123 | 132 | 142 | 147 |
| Glucose mg/dL | 80-150* | 181 | 200 | 187 | 190 |

TABLE 71

Effect of mixed backbone antisense compound ISIS 366849 on indicators of liver and kidney function

| Serum indicator | Normal Range | Units measured per dose of ISIS 366849 | | | |
|---|---|---|---|---|---|
| | | Saline | 0.14 µM/kg | 0.7 µM/kg | 3.5 µM/kg |
| BUN mg/dL | 15-40 | 31 | 25 | 30 | 33 |
| Creatinine mg/L | 0.0-1.0 | 0.2 | 0.2 | 0.2 | 0.2 |
| Bilirubin mg/dL | 0.1-1.0 | 0.2 | 0.1 | 0.1 | 0.1 |
| AST IU/L | 30-300 | 82 | 98 | 90 | 92 |
| ALT IU/L | 30-200 | 22 | 26 | 24 | 33 |
| Albumin g/dL | 2.5-4.0 | 3.0 | 3.0 | 3.0 | 3.0 |
| Triglycerides mg/dL | 25-100* | 225 | 354 | 308 | 240 |
| Cholesterol mg/dL | 70-125 | 123 | 133 | 129 | 150 |
| Glucose mg/dL | 80-150* | 181 | 170 | 173 | 192 |

TABLE 72

Effect of mixed backbone antisense compound ISIS 366850 on indicators of liver and kidney function

| Serum indicator | Normal Range | Units measured per dose of ISIS 366850 | | | |
|---|---|---|---|---|---|
| | | Saline | 0.14 µM/kg | 0.7 µM/kg | 3.5 µM/kg |
| BUN mg/dL | 15-40 | 31 | 26 | 25 | 23 |
| Creatinine mg/L | 0.0-1.0 | 0.2 | 0.2 | 0.2 | 0.2 |
| Bilirubin mg/dL | 0.1-1.0 | 0.2 | 0.1 | 0.1 | 0 |
| AST IU/L | 30-300 | 82 | 83 | 69 | 108 |
| ALT IU/L | 30-200 | 22 | 21 | 27 | 38 |
| Albumin g/dL | 2.5-4.0 | 3.0 | 3.0 | 3.0 | 3.0 |
| Triglycerides mg/dL | 25-100* | 225 | 320 | 380 | 271 |
| Cholesterol mg/dL | 70-125 | 123 | 127 | 131 | 164 |
| Glucose mg/dL | 80-150* | 181 | 192 | 187 | 179 |

*Triglyceride and glucose levels are routinely higher in the Balb/c strain of mice than in other strains of mice.

Some oligonucleotide treated animals exhibited elevated levels of cholesterol; however, saline control animals also demonstrated cholesterol levels at the high end of the normal range. Thus, the slightly elevated cholesterol levels do not appear to be significant. Otherwise, the levels of routine clinical indicators of liver and kidney injury and disease are within normal ranges and are not significantly changed relative to saline-treated animals, demonstrating that the compounds of the invention do not significantly affect renal or hepatic function. Triglyceride and glucose levels, while outside the normal range as is common in the Balb/c strain, are not significantly elevated relative to saline-treated animals.

The results illustrated in this example demonstrate that mixed backbone compounds of 16 to 20 nucleobases are delivered to the kidney, reduce SGLT2 expression in vivo, and that treatment with these compounds does not result in liver or kidney toxicity.

Example 33

Antisense Inhibition of SGLT2 in Sprague Dawley Rats

In accordance with the present invention, 7-week old Sprague Dawley rats (purchased from Charles River Labs, Wilmington, Mass.) were treated with SGLT2 mixed backbone compound ISIS 257016 (SEQ ID NO: 106) or SGLT2 full phosphorothioate compound ISIS 145733 (SEQ ID NO: 106). Rats were injected i.p. twice a week for three weeks with 10 mg/kg of oligonucleotide. Saline-injected animals served as controls. The rats were sacrificed 2 days following administration of the final dose of oligonucleotide or saline.

Rats were evaluated for SGLT2 levels in kidney. Target levels were determined by quantitative real-time PCR as described in other examples herein. PCR results were normalized to cyclophilin. The data are expressed as percent change relative to saline treated animals ("+" indicates an increase, "−" indicates a decrease) and are illustrated in Table 73.

TABLE 73

Antisense inhibition of SGLT2 mRNA expression in Sprague Dawley rats (expressed as percent change in SGLT2 mRNA expression relative to saline)

| Treatment | % Change in mRNA |
|---|---|
| Saline | 0 |
| ISIS 257016 | −83.9 |
| ISIS 145733 | −38.5 |

These results illustrate that both full phosphorothioate and mixed backbone compounds inhibit SGLT2 expression in the kidney of rats. However, the mixed backbone compound is a more effective inhibitor of SGLT2.

Treated rats were further evaluated for body weight, kidney weight, liver weight and spleen weight. For body weight, the data are expressed as percent change in body weight ("+" indicates an increase, "−" indicates a decrease). For organ weights, the results are expressed as percent of saline control normalized to body weight. The results are presented in Table 74 and Table 75.

TABLE 74

Effects of antisense compounds on total body weight of rats (expressed as percent change in weight)

| Treatment | Body weight |
|---|---|
| Saline | +60.7 |
| ISIS 257016 | +58.4 |
| ISIS 145733 | +57.1 |

TABLE 75

Effects of antisense compounds on total kidney weight, liver weight and spleen weight of rats (expressed as percent of saline control normalized to body weight)

| Treatment | Kidney weight | Liver weight | Spleen weight |
|---|---|---|---|
| ISIS 257016 | 99.3 | 93.4 | 105.8 |
| ISIS 145733 | 107.2 | 105.2 | 123.4 |

No significant change was observed in total body weight, kidney weight, liver weight or spleen weight at timepoints throughout or at the termination of the study.

Levels of BUN, creatinine, bilirubin, AST, ALT, albumin, triglycerides, cholesterol and glucose were measured in rats treated with the compounds of the invention. Plasma samples were analyzed using the Olympus AU400e automated chemistry analyzer (Olympus America, Irving, Tex.). The results, expressed as units measured, are shown in Table 76.

TABLE 76

Effect of mixed backbone antisense compound ISIS 257016 and full phosphorothioate compound ISIS 145733 on indicators of liver and kidney function (expressed as units measured)

| Serum Indicator | Saline | ISIS 257016 | ISIS 145733 |
|---|---|---|---|
| BUN mg/dL | 19 | 19 | 17 |
| Creatinine mg/L | 0.3 | 0.4 | 0.2 |
| Bilirubin mg/dL | 0.1 | 0.1 | 0.1 |
| AST IU/L | 157 | 105 | 105 |
| ALT IU/L | 65 | 44 | 36 |
| Albumin g/dL | 3.7 | 3.8 | 3.6 |
| Triglycerides mg/dL | 42 | 47 | 53 |
| Cholesterol mg/dL | 68 | 66 | 54 |
| Glucose mg/dL | 189 | 173 | 180 |

The levels of routine clinical indicators of liver and kidney injury are not significantly changed relative to saline-treated animals, demonstrating that the compounds of the invention do not significantly affect renal or hepatic function in rats.

The results illustrated in this example demonstrate that both full phosphorothioate and mixed backbone compounds are delivered to the kidney, reduce SGLT2 expression in vivo, and that treatment with these compounds does not result in liver or kidney toxicity. The results further indicate that mixed backbone compounds are more effective inhibitors of SGLT2 expression in vivo.

Various modifications of the invention, in addition to those described herein, will be apparent to those skilled in the art

What is claimed is:

1. A compound comprising a modified oligomeric compound, wherein the modified oligomeric compound is 10 to 30 nucleobases in length, specifically hybridizable with SEQ ID NO: 4, and 100% complementary to at least an 8 nucleobase portion of nucleotides 1100 to 1170 of SEQ ID NO: 4 encoding SGLT2, and wherein said modified oligomeric compound comprises:
   a gap segment consisting of linked deoxynucleosides;
   a 5' wing segment consisting of linked nucleosides; and
   a 3' wing segment consisting of linked nucleosides;
   wherein the gap segment is positioned between the 5' wing segment and the 3' wing segment and wherein each of said nucleosides of each of said wing segments comprises a modified sugar.

2. The compound of claim 1 wherein said modified oligomeric compound comprises 13 to 30 nucleobases in length.

3. The compound of claim 2 wherein said modified oligomeric compound comprises 15 to 25 nucleobases in length.

4. The compound of claim 3 wherein said modified oligomeric compound comprises 18 to 22 nucleobases in length.

5. The compound of claim 1, wherein at least a portion of the modified oligomeric compound hybridizes with RNA to form an oligonucleotide-RNA duplex.

6. The compound of claim 1 wherein said modified oligomeric compound comprises at least 80% complementarity with the nucleic acid molecule encoding SEQ ID NO: 4.

7. The compound of claim 1 wherein said modified oligomeric compound comprises at least 90% complementarity with the nucleic acid molecule encoding SEQ ID NO: 4.

8. The compound of claim 1 wherein said modified oligomeric compound comprises at least 95% complementarity with the nucleic acid molecule encoding SEQ ID NO: 4.

9. The compound of claim 1 wherein said modified oligomeric compound comprises at least 99% complementarity with the nucleic acid molecule encoding SEQ ID NO: 4.

10. The compound of claim 1 wherein said modified oligomeric compound is 100% complementary with the nucleic acid molecule encoding SEQ ID NO: 4.

11. The compound of claim 1 wherein said modified oligomeric compound comprises at least one modified internucleoside linkage, or nucleobase.

12. The compound of claim 11, wherein the modified oligomeric compound comprises at least one modified internucleoside linkage.

13. The compound of claim 11, wherein the modified oligomeric compound comprises at least one modified nucleobase.

14. The compound of claim 1 wherein said modified oligomeric compound comprises at least one 2'-O-methoxyethyl sugar moiety.

15. The compound of claim 1 wherein said modified oligomeric compound comprises at least one phosphorothioate internucleoside linkage.

16. The compound of claim 1 wherein said modified oligomeric compound comprises at least one 5-methylcytosine.

17. The compound of claim 1 wherein the modified oligomeric compound comprises at least an 8-nucleobase portion of SEQ ID NO: 54, 55, or 56.

18. The compound of claim 17 wherein the modified oligomeric compound comprises the nucleobase sequences set forth in SEQ ID NO: 54, 55, or 56.

19. The compound of claim 18, wherein the modified oligomeric compound comprises the nucleobase sequence of SEQ ID NO:54.

20. The compound of claim 18, wherein the modified oligomeric compound comprises the nucleobase sequence of SEQ ID NO:55.

21. The compound of claim 18, wherein the modified oligomeric compound comprises the nucleobase sequence of SEQ ID NO:56.

22. The compound of claim 17, wherein the modified oligomeric compound comprises at least an 8-nucleobase portion of SEQ ID NO:54.

23. The compound of claim 17, wherein the modified oligomeric compound comprises at least an 8-nucleobase portion of SEQ ID NO:55.

24. The compound of claim 17, wherein the modified oligomeric compound comprises at least an 8-nucleobase portion of SEQ ID NO:56.

25. The compound of claim 1 which comprises a first region consisting of at least 5 contiguous 2'-deoxy nucleosides flanked by a second region and a third region, wherein each of the second and third regions, independently, comprises at least one 2'-O-methoxyethyl nucleoside, and wherein the internucleoside linkages of the first region are phosphorothioate linkages and the internucleoside linkages of the second and third regions are phosphodiester linkages.

26. The compound of claim 1, wherein the compound inhibits the expression of SGLT2 mRNA by at least 30%.

27. A method of inhibiting the expression of SGLT2 in a cell or tissue comprising contacting the cell or tissue with the compound of claim 1 so that expression of SGLT2 is inhibited.

28. A kit or assay device comprising the compound of claim 1.

29. A method of treating an animal having a disease or condition associated with SGLT2 comprising administering to the animal a therapeutically effective amount of the compound of claim 1 so that expression of SGLT2 is inhibited.

30. The method of claim 29 wherein the disease or condition is a hyperproliferative or metabolic disorder.

31. A method of inhibiting the expression of SGLT2 in a kidney cell or kidney tissue comprising contacting the kidney cell or kidney tissue with the compound of claim 25.

32. A method of inhibiting expression of SGLT2 in a kidney cell or kidney tissue comprising contacting the kidney cell or kidney tissue with the compound of claim 25 so that expression of SGLT2 is inhibited.

33. The method of claim 32 wherein the compound comprises SEQ ID NO: 54, 55, or 56.

34. A method of delaying the onset of a disease or condition in an animal comprising administering to the animal an effective amount of the compound of claim 25 so that expression of SGLT2 is inhibited, wherein the disease or condition is associated with expression of SGLT2 in the kidney.

35. The method of claim 34 wherein the compound comprises SEQ ID NO: 54, 55, or 56.

36. The method of claim 34 wherein said animal is a human.

37. The method of claim 34 wherein the compound consists of SEQ ID NO: 54, 55, or 56.

38. A method of delaying the onset of type 2 diabetes in an animal comprising administering to the animal the compound of claim 25 so that expression of SGLT2 is inhibited.

39. A method of delaying the onset of an increase in blood glucose level in an animal comprising administering to the animal the compound of claim 25 so that expression of SGLT2 is inhibited.

40. The method of claim 39 wherein the animal is a human.

41. The method of claim 39 wherein the blood glucose level is plasma glucose level or serum glucose level.

42. The method of claim 39 wherein the animal is a diabetic animal.

43. The method of claim 39 wherein the animal is insulin-resistant as compared to a normal animal.

44. The method of claim 39 wherein the compound comprises SEQ ID NO: 54, 55, or 56.

45. A method of decreasing blood glucose level in an animal comprising administering to the animal the compound of claim 25 so that expression of SGLT2 is inhibited.

46. The method of claim 45 wherein the animal is a human.

47. The method of claim 45 wherein the blood glucose level is plasma glucose level or serum glucose level.

48. The method of claim 45 wherein the animal is a diabetic animal.

49. The method of claim 45 wherein the animal is insulin-resistant as compared to a normal animal.

50. The method of claim 45 wherein the compound comprises SEQ ID NO: 54, 55, or 56.

51. A method of inhibiting expression of SGLT2 in a kidney cell or kidney tissue comprising contacting the cell or tissue with the compound of claim 1, wherein the expression of SGLT2 is inhibited.

52. A pharmaceutical composition comprising a modified oligomeric compound, or salt form thereof, wherein the oligomeric compound is 10 to 30 nucleobases in length, specifically hybridizable with SEQ ID NO:4, and 100% complementary to at least an 8 nucleobase portion of nucleotides 1100 to 1170 of SEQ ID NO:4, wherein the oligomeric compound comprises:
    a gap segment consisting of linked deoxynucleosides;
    a 5' wing segment consisting of linked nucleosides; and
    a 3' wing segment consisting of linked nucleosides;
    wherein the gap segment is positioned between the 5' wing segment and the 3' wing segment and wherein each of said nucleosides of each of said wing segments comprises a modified sugar; and a pharmaceutically acceptable carrier or diluent.

53. The pharmaceutical composition of claim 52, wherein the oligomeric compound comprises:
    a gap segment consisting of ten linked deoxynucleosides;
    a 5' wing segment consisting of five linked nucleosides; and
    a 3' wing segment consisting of five linked nucleosides;
    wherein the gap segment is positioned between the 5' wing segment and the 3' wing segment, wherein each of said nucleosides of each of said wing segments comprises a 2'-O-methyoxyethyl sugar; and wherein each internucleoside linkage is a phosphorothioate linkage.

54. A compound comprising a modified oligomeric compound, wherein the modified oligomeric compound is 10 to 30 nucleobases in length, specifically hybridizable with SEQ ID NO: 4, and 100% complementary to at least an 8 nucleobase portion of nucleotides 1122 to 1141 of SEQ ID NO: 4 encoding SGLT2, and wherein said modified oligomeric compound comprises:
    a gap segment consisting of linked deoxynucleosides;
    a 5' wing segment consisting of linked nucleosides; and
    a 3' wing segment consisting of linked nucleosides;
    wherein the gap segment is positioned between the 5' wing segment and the 3' wing segment, wherein each nucleoside of each wing segment comprises a 2'-O-methoxyethyl sugar; and wherein each internucleoside linkage is a phosphorothioate linkage.

* * * * *

SEQUENCE LISTING

<160> NUMBER OF SEQ ID NOS: 275

<210> SEQ ID NO 1
<211> LENGTH: 20
<212> TYPE: DNA
<213> ORGANISM: Artificial Sequence
<220> FEATURE:
<223> OTHER INFORMATION: Antisense Compound

<400> SEQUENCE: 1
tccgtcatcg ctcctcaggg                                              20

<210> SEQ ID NO 2
<211> LENGTH: 20
<212> TYPE: DNA
<213> ORGANISM: Artificial Sequence
<220> FEATURE:
<223> OTHER INFORMATION: Antisense Compound

<400> SEQUENCE: 2
gtgcgcgcga gcccgaaatc                                              20

<210> SEQ ID NO 3
<211> LENGTH: 20
<212> TYPE: DNA
<213> ORGANISM: Artificial Sequence
<220> FEATURE:
<223> OTHER INFORMATION: Antisense Compound

<400> SEQUENCE: 3
atgcattctg cccccaagga                                              20

<210> SEQ ID NO 4
<211> LENGTH: 2273
<212> TYPE: DNA
<213> ORGANISM: H. sapiens
<220> FEATURE:
<221> NAME/KEY: CDS
<222> LOCATION: (21)...(2039)

<400> SEQUENCE: 4

```
gggggcagat cctggggaga atg gag gag cac aca gag gca ggc tcg gca cca      53
                      Met Glu Glu His Thr Glu Ala Gly Ser Ala Pro
                        1               5                  10 gag atg ggg gcc cag aag gcc ctg att gac aat cct gct gac atc cta       101
Glu Met Gly Ala Gln Lys Ala Leu Ile Asp Asn Pro Ala Asp Ile Leu
             15                  20                  25 gtc att gct gca tat ttc ctg ctg gtc att ggc gtt ggc ttg tgg tcc       149
Val Ile Ala Ala Tyr Phe Leu Leu Val Ile Gly Val Gly Leu Trp Ser
         30                  35                  40 atg tgc aga acc aac aga ggc act gtg ggc ggc tac ttc ctg gca gga       197
Met Cys Arg Thr Asn Arg Gly Thr Val Gly Gly Tyr Phe Leu Ala Gly
     45                  50                  55 cgc agc atg gtg tgg tgg ccg gtt ggg gcc tct ctc ttc gcc agc aac       245
Arg Ser Met Val Trp Trp Pro Val Gly Ala Ser Leu Phe Ala Ser Asn
 60                  65                  70                  75 atc ggc agt ggc cac ttt gtg ggc ctg gca ggg act ggc gct gca agt       293
Ile Gly Ser Gly His Phe Val Gly Leu Ala Gly Thr Gly Ala Ala Ser
                 80                  85                  90 ggc ttg gct gtt gct gga ttc gag tgg aat gcg ctc ttc gtg gtg ctg       341
Gly Leu Ala Val Ala Gly Phe Glu Trp Asn Ala Leu Phe Val Val Leu
             95                 100                 105 cta ctg ggc tgg ctg ttt gca ccc gtg tac ctg aca gcg ggg gtc atc       389
```

```
                Leu Leu Gly Trp Leu Phe Ala Pro Val Tyr Leu Thr Ala Gly Val Ile
                        110                 115                 120 acg atg cca cag tac ctg cgc aag cgc ttc ggc ggc cgc cgc atc cgc        437
Thr Met Pro Gln Tyr Leu Arg Lys Arg Phe Gly Gly Arg Arg Ile Arg
        125                 130                 135 ctc tac ctg tct gtc ctc tcc ctt ttc ctg tac atc ttc acc aag atc        485
Leu Tyr Leu Ser Val Leu Ser Leu Phe Leu Tyr Ile Phe Thr Lys Ile
140                 145                 150                 155 tca gtg gac atg ttc tcc gga gct gta ttc atc cag cag gct ctg ggc        533
Ser Val Asp Met Phe Ser Gly Ala Val Phe Ile Gln Gln Ala Leu Gly
                160                 165                 170 tgg aac atc tat gcc tcc gtc atc gcg ctt ctg ggc atc acc atg att        581
Trp Asn Ile Tyr Ala Ser Val Ile Ala Leu Leu Gly Ile Thr Met Ile
            175                 180                 185 tac acg gtg aca gga ggg ctg gcc gcg ctg atg tac acg gac acg gta        629
Tyr Thr Val Thr Gly Gly Leu Ala Ala Leu Met Tyr Thr Asp Thr Val
        190                 195                 200 cag acc ttc gtc att ctg ggg ggc gcc tgc atc ctc atg ggt tac gcc        677
Gln Thr Phe Val Ile Leu Gly Gly Ala Cys Ile Leu Met Gly Tyr Ala
    205                 210                 215 ttc cac gag gtg ggc ggg tat tcg ggt ctc ttc gac aaa tac ctg gga        725
Phe His Glu Val Gly Gly Tyr Ser Gly Leu Phe Asp Lys Tyr Leu Gly
220                 225                 230                 235 gca gcg act tcg ctg acg gtg tcc gag gat cca gcc gtg gga aac atc        773
Ala Ala Thr Ser Leu Thr Val Ser Glu Asp Pro Ala Val Gly Asn Ile
                240                 245                 250 tcc agc ttc tgc tat cga ccc cgg ccc gac tcc tac cac ctg ctc cgg        821
Ser Ser Phe Cys Tyr Arg Pro Arg Pro Asp Ser Tyr His Leu Leu Arg
            255                 260                 265 cac ccc gtg acc ggg gat ctg ccg tgg ccc gcg ctg ctc ctc gga ctc        869
His Pro Val Thr Gly Asp Leu Pro Trp Pro Ala Leu Leu Leu Gly Leu
        270                 275                 280 aca atc gtc tcg ggc tgg tac tgg tgc agc gac cag gtc atc gtg cag        917
Thr Ile Val Ser Gly Trp Tyr Trp Cys Ser Asp Gln Val Ile Val Gln
    285                 290                 295 cgc tgc ctg gcc ggg aag agc ctg acc cac atc aag gcg ggc tgc atc        965
Arg Cys Leu Ala Gly Lys Ser Leu Thr His Ile Lys Ala Gly Cys Ile
300                 305                 310                 315 ctg tgt ggg tac ctg aag ctg acg ccc atg ttt ctc atg gtc atg cca       1013
Leu Cys Gly Tyr Leu Lys Leu Thr Pro Met Phe Leu Met Val Met Pro
                320                 325                 330 ggc atg atc agc cgc att ctg tac cca gac gag gtg gcg tgc gtg gtg       1061
Gly Met Ile Ser Arg Ile Leu Tyr Pro Asp Glu Val Ala Cys Val Val
            335                 340                 345 cct gag gtg tgc agg cgc gtg tgc ggc acg gag gtg ggc tgc tcc aac       1109
Pro Glu Val Cys Arg Arg Val Cys Gly Thr Glu Val Gly Cys Ser Asn
        350                 355                 360 atc gcc tac ccg cgg ctc gtc gtg aag ctc atg ccc aac ggt ctg cgc       1157
Ile Ala Tyr Pro Arg Leu Val Val Lys Leu Met Pro Asn Gly Leu Arg
    365                 370                 375 gga ctc atg ctg gcg gtc atg ctg gcc gcg ctc atg tcc tcg ctg gcc       1205
Gly Leu Met Leu Ala Val Met Leu Ala Ala Leu Met Ser Ser Leu Ala
380                 385                 390                 395 tcc atc ttc aac agc agc agc acg ctc ttc acc atg gac atc tac acg       1253
Ser Ile Phe Asn Ser Ser Ser Thr Leu Phe Thr Met Asp Ile Tyr Thr
                400                 405                 410 cgc ctg cgg cca cgc gcc ggc gac cgc gag ctg ctg ctg gtg gga cgg       1301
Arg Leu Arg Pro Arg Ala Gly Asp Arg Glu Leu Leu Leu Val Gly Arg
            415                 420                 425 ctc tgg gtg gtg ttc atc gtg gta gtg tcg gtg gcc tgg ctt ccc gtg       1349
```

|   |   |   |   |   |   |   |   |   |   |   |   | |
|---|---|---|---|---|---|---|---|---|---|---|---|---|
| Leu | Trp | Val | Val | Phe | Ile | Val | Val | Ser | Val | Ala | Trp | Leu | Pro | Val |
|  |  | 430 |  |  |  | 435 |  |  |  | 440 |  |  |

```
gtg cag gcg gca cag ggc ggg cag ctc ttc gat tac atc cag gca gtc      1397
Val Gln Ala Ala Gln Gly Gly Gln Leu Phe Asp Tyr Ile Gln Ala Val
    445             450             455 tct agc tac ctg gca ccg ccc gtc tcc gcc gtc ttc gtg ctg gcg ctc      1445
Ser Ser Tyr Leu Ala Pro Pro Val Ser Ala Val Phe Val Leu Ala Leu
460             465             470             475 ttc gtg ccg cgc gtt aat gag cag ggc gcc ttc tgg gga ctc atc ggg      1493
Phe Val Pro Arg Val Asn Glu Gln Gly Ala Phe Trp Gly Leu Ile Gly
            480             485             490 ggc ctg ctg atg ggc ctg gca cgc ctg att ccc gag ttc tcc ttc ggc      1541
Gly Leu Leu Met Gly Leu Ala Arg Leu Ile Pro Glu Phe Ser Phe Gly
        495             500             505 tcg ggc agc tgt gtg cag ccc tcg gcg tgc cca gct ttc ctc tgc ggc      1589
Ser Gly Ser Cys Val Gln Pro Ser Ala Cys Pro Ala Phe Leu Cys Gly
    510             515             520 gtg cac tac ctc tac ttc gcc att gtg ctg ttc ttc tgc tct ggc ctc      1637
Val His Tyr Leu Tyr Phe Ala Ile Val Leu Phe Phe Cys Ser Gly Leu
525             530             535 ctc acc ctc acg gtc tcc ctg tgc acc gcg ccc atc ccc aga aag cac      1685
Leu Thr Leu Thr Val Ser Leu Cys Thr Ala Pro Ile Pro Arg Lys His
540             545             550             555 ctc cac cgc ctg gtc ttc agt ctc cgg cat agc aag gag gaa cgg gag      1733
Leu His Arg Leu Val Phe Ser Leu Arg His Ser Lys Glu Glu Arg Glu
            560             565             570 gac ctg gat gct gat gag cag caa ggc tcc tca ctc cct gta cag aat      1781
Asp Leu Asp Ala Asp Glu Gln Gln Gly Ser Ser Leu Pro Val Gln Asn
        575             580             585 ggg tgc cca gag agt gcc atg gag atg aat gag ccc cag gcc ccg gca      1829
Gly Cys Pro Glu Ser Ala Met Glu Met Asn Glu Pro Gln Ala Pro Ala
    590             595             600 cca agc ctc ttc cgc cag tgc ctg ctc tgg ttt tgt gga atg agc aga      1877
Pro Ser Leu Phe Arg Gln Cys Leu Leu Trp Phe Cys Gly Met Ser Arg
605             610             615 ggt ggg gtg ggc agt cct ccg ccc ctt acc cag gag gag gca gcg gca      1925
Gly Gly Val Gly Ser Pro Pro Pro Leu Thr Gln Glu Glu Ala Ala Ala
620             625             630             635 gca gcc agg cgg ctg gag gac atc agc gag gac ccg agc tgg gcc cgt      1973
Ala Ala Arg Arg Leu Glu Asp Ile Ser Glu Asp Pro Ser Trp Ala Arg
            640             645             650 gtc gtc aac ctc aat gcc ctg ctc atg atg gca gtg gcc gtg ttc ctc      2021
Val Val Asn Leu Asn Ala Leu Leu Met Met Ala Val Ala Val Phe Leu
        655             660             665 tgg ggc ttc tat gcc taa gaccaactgc gttggacacc ataagccaca             2069
Trp Gly Phe Tyr Ala *
    670 gcctcacagg aagtgggggt gaggagcctg cggtgctccc cagaaaaggg gaaggggcag    2129 tggggtgaga aggtcctggc tccccttctc ccggccttcc tctgcctggg gcccactgca    2189 tctgattggc agtcacttcc catgagggcc tggcccaccc gctgcagttg ccctaaggaa    2249 aaataaagct gcctttcccc tgta                                          2273

<210> SEQ ID NO 5
<211> LENGTH: 15
<212> TYPE: DNA
<213> ORGANISM: Artificial Sequence
<220> FEATURE:
<223> OTHER INFORMATION: PCR Primer

<400> SEQUENCE: 5
```

```
tcggcgtgcc cagct                                                    15

<210> SEQ ID NO 6
<211> LENGTH: 21
<212> TYPE: DNA
<213> ORGANISM: Artificial Sequence
<220> FEATURE:
<223> OTHER INFORMATION: PCR Primer

<400> SEQUENCE: 6
agaacagcac aatggcgaag t                                             21

<210> SEQ ID NO 7
<211> LENGTH: 23
<212> TYPE: DNA
<213> ORGANISM: Artificial Sequence
<220> FEATURE:
<223> OTHER INFORMATION: PCR Probe

<400> SEQUENCE: 7
tcctctgcgg cgtgcactac ctc                                           23

<210> SEQ ID NO 8
<211> LENGTH: 19
<212> TYPE: DNA
<213> ORGANISM: Artificial Sequence
<220> FEATURE:
<223> OTHER INFORMATION: PCR Primer

<400> SEQUENCE: 8
gaaggtgaag gtcggagtc                                                19

<210> SEQ ID NO 9
<211> LENGTH: 20
<212> TYPE: DNA
<213> ORGANISM: Artificial Sequence
<220> FEATURE:
<223> OTHER INFORMATION: PCR Primer

<400> SEQUENCE: 9
gaagatggtg atgggatttc                                               20

<210> SEQ ID NO 10
<211> LENGTH: 20
<212> TYPE: DNA
<213> ORGANISM: Artificial Sequence
<220> FEATURE:
<223> OTHER INFORMATION: PCR Probe

<400> SEQUENCE: 10
caagcttccc gttctcagcc                                               20

<210> SEQ ID NO 11
<211> LENGTH: 2453
<212> TYPE: DNA
<213> ORGANISM: M. musculus
<220> FEATURE:
<221> NAME/KEY: CDS
<222> LOCATION: (6)...(2018)
<220> FEATURE:
<221> NAME/KEY: misc_feature
<222> LOCATION: 510, 657, 702, 741, 1231, 1370, 1426, 1432, 1677
<223> OTHER INFORMATION: n = A,T,C or G

<400> SEQUENCE: 11 agaga atg gag caa cac gta gag gca ggc tct gaa ctt ggg gag cag aag   50
      Met Glu Gln His Val Glu Ala Gly Ser Glu Leu Gly Glu Gln Lys
```

-continued

```
            1                   5                  10                 15
gtc ctg att gat aat cct gct gac att ctg gtt atc gct gcc tat ttc         98
Val Leu Ile Asp Asn Pro Ala Asp Ile Leu Val Ile Ala Ala Tyr Phe
                    20                 25                 30 ctg ctg gtc att ggt gtt ggc ttg tgg tct atg ttc aga acc aat aga        146
Leu Leu Val Ile Gly Val Gly Leu Trp Ser Met Phe Arg Thr Asn Arg
                    35                 40                 45 ggc aca gtt ggt ggc tac ttc ctg gca gga cgg aac atg gtg tgg tgg        194
Gly Thr Val Gly Gly Tyr Phe Leu Ala Gly Arg Asn Met Val Trp Trp
                    50                 55                 60 ccg gtt gga gcc tct ctg ttc gcc agc aac atc ggc agc ggt cat ttt        242
Pro Val Gly Ala Ser Leu Phe Ala Ser Asn Ile Gly Ser Gly His Phe
                    65                 70                 75 gtg ggc ctg gca ggg act ggt gca gca agt ggc ttg gcg gtg gct gga        290
Val Gly Leu Ala Gly Thr Gly Ala Ala Ser Gly Leu Ala Val Ala Gly
            80                 85                 90                 95 ttt gag tgg aat gcg ctc ttc gtg gtg ctg ctc ctc gga tgg ctt ttt        338
Phe Glu Trp Asn Ala Leu Phe Val Val Leu Leu Leu Gly Trp Leu Phe
                    100                105                110 gtg cca gtg tat ctg acc gct ggc gtg atc aca atg cct cag tac ctc        386
Val Pro Val Tyr Leu Thr Ala Gly Val Ile Thr Met Pro Gln Tyr Leu
                    115                120                125 cgc aag cgc ttt ggt ggg cac cgt att cgc ctc tac ctg tcc gtg ctc        434
Arg Lys Arg Phe Gly Gly His Arg Ile Arg Leu Tyr Leu Ser Val Leu
                    130                135                140 tcg ctt ttt ttg tac att ttc acc aag atc tcg gtg gat atg ttc tct        482
Ser Leu Phe Leu Tyr Ile Phe Thr Lys Ile Ser Val Asp Met Phe Ser
                    145                150                155 ggg gca gta ttc att caa cag gcc ctg ngc tgg aac att tac gct tcg        530
Gly Ala Val Phe Ile Gln Gln Ala Leu Xaa Trp Asn Ile Tyr Ala Ser
160                 165                170                175 gtc atc gct ctc ttg ggc atc acc atg att tat act gtg aca gga ggg        578
Val Ile Ala Leu Leu Gly Ile Thr Met Ile Tyr Thr Val Thr Gly Gly
                    180                185                190 ctg gcg gca ctg atg tac aca gac act gtg cag acc ttc gtc att ctt        626
Leu Ala Ala Leu Met Tyr Thr Asp Thr Val Gln Thr Phe Val Ile Leu
                    195                200                205 gcc ggg gcc tcc atc ctc act ggt tat gct ntc cat gaa gtg ggc ggg        674
Ala Gly Ala Ser Ile Leu Thr Gly Tyr Ala Xaa His Glu Val Gly Gly
                    210                215                220 tac ttc ggt ctc ttc gac aca tac ctg nga gca atg act tca ctg acg        722
Tyr Phe Gly Leu Phe Asp Thr Tyr Leu Xaa Ala Met Thr Ser Leu Thr
                    225                230                235 ggt gtc cag gat cca tct ngt ggg cac atc tcc agc acc tgc tac cag        770
Gly Val Gln Asp Pro Ser Xaa Gly His Ile Ser Ser Thr Cys Tyr Gln
240                 245                250                255 ccg agg cct gac tcc tat cac ctg ctg cgt gac cct gtg aca gga gac        818
Pro Arg Pro Asp Ser Tyr His Leu Leu Arg Asp Pro Val Thr Gly Asp
                    260                265                270 ctg cca tgg cct gcg ctg ctc ctg ggg ctt acc att gtc tcg ggc tgg        866
Leu Pro Trp Pro Ala Leu Leu Leu Gly Leu Thr Ile Val Ser Gly Trp
                    275                280                285 tat tgg tgc agc gat cag gta ata gtg cag cgg tgc ctg gct gga aag        914
Tyr Trp Cys Ser Asp Gln Val Ile Val Gln Arg Cys Leu Ala Gly Lys
                    290                295                300 aat ctg act cac atc aaa gct ggg tgc atc ttg tgt ggc tac ctg aag        962
Asn Leu Thr His Ile Lys Ala Gly Cys Ile Leu Cys Gly Tyr Leu Lys
                    305                310                315 ctg atg ccc atg ttc ctc atg gtc atg cca ggc atg atc agc cgc att       1010
Leu Met Pro Met Phe Leu Met Val Met Pro Gly Met Ile Ser Arg Ile
```

```
              320                 325                 330                 335 ctc tac cca gat gag gtg gca tgt gtg gta cct gag gtg tgt aag cgg          1058
Leu Tyr Pro Asp Glu Val Ala Cys Val Val Pro Glu Val Cys Lys Arg
                    340                 345                 350 gtg tgt ggc act gag gtg ggc tgc tct aac atc gcc tac cca cag ctc          1106
Val Cys Gly Thr Glu Val Gly Cys Ser Asn Ile Ala Tyr Pro Gln Leu
            355                 360                 365 gtg gtg aag ctc atg ccc aat ggt ctg cgc gga ctc atg ctg gca gtc          1154
Val Val Lys Leu Met Pro Asn Gly Leu Arg Gly Leu Met Leu Ala Val
        370                 375                 380 atg ctg gct gcc ctc atg tct tct ctg gca tcc atc ttt aac agc agt          1202
Met Leu Ala Ala Leu Met Ser Ser Leu Ala Ser Ile Phe Asn Ser Ser
    385                 390                 395 agc acg ctc ttc acc atg gat atc tac anc gcg cct gcg gcc cgt gca          1250
Ser Thr Leu Phe Thr Met Asp Ile Tyr Xaa Ala Pro Ala Ala Arg Ala
400                 405                 410                 415 ggt gat aag gag ctg ctg cta gtt gga agg ctc tgg gtg gta ttc atc          1298
Gly Asp Lys Glu Leu Leu Leu Val Gly Arg Leu Trp Val Val Phe Ile
                420                 425                 430 gtg gcg gtg tcc gtg gct cgg ctg cca gtg gtg cag gca gct cag ggt          1346
Val Ala Val Ser Val Ala Arg Leu Pro Val Val Gln Ala Ala Gln Gly
            435                 440                 445 ggg cag ctc ttc gat tac atc agn tct gtc tcc agc tat ctg gca cct          1394
Gly Gln Leu Phe Asp Tyr Ile Xaa Ser Val Ser Ser Tyr Leu Ala Pro
        450                 455                 460 caa gtg tct gcg gtc ttt gtg ctt gca ctc tnt gtg cnc cgt gtt aat          1442
Gln Val Ser Ala Val Phe Val Leu Ala Leu Xaa Val Xaa Arg Val Asn
    465                 470                 475 gag aag gga gcc ttc tgg gga cta gtt ggg ggc ctg ctg atg ggc cta          1490
Glu Lys Gly Ala Phe Trp Gly Leu Val Gly Gly Leu Leu Met Gly Leu
480                 485                 490                 495 gct cgt ctc ata ccc gag ttc ttc ttt ggc tcg ggc agc tgt gtg cga          1538
Ala Arg Leu Ile Pro Glu Phe Phe Phe Gly Ser Gly Ser Cys Val Arg
                500                 505                 510 ccc tca gcg tgc ccg gca ctc ttc tgt cgg gta cac tac ctc tat ttc          1586
Pro Ser Ala Cys Pro Ala Leu Phe Cys Arg Val His Tyr Leu Tyr Phe
            515                 520                 525 gcc atc att ctc ttc atc tgc tct ggc atc ctc aca ctg gga atc tcc          1634
Ala Ile Ile Leu Phe Ile Cys Ser Gly Ile Leu Thr Leu Gly Ile Ser
        530                 535                 540 ctg tgc act ggc cca tcc cct cag aag cat ctc cat cgc tgg ntt ttc          1682
Leu Cys Thr Gly Pro Ser Pro Gln Lys His Leu His Arg Trp Xaa Phe
    545                 550                 555 agt ctc cgg cac agc aag gag gag cgg gag gac ctg gat gct gat gag          1730
Ser Leu Arg His Ser Lys Glu Glu Arg Glu Asp Leu Asp Ala Asp Glu
560                 565                 570                 575 tta gaa ggt cca gcc cct gct cct gtg cag aac ggg ggc cag gaa tgt          1778
Leu Glu Gly Pro Ala Pro Ala Pro Val Gln Asn Gly Gly Gln Glu Cys
                580                 585                 590 gca atg gag atg gaa gag gtc cag tcc ccg gct cca ggc ctg ctc cgc          1826
Ala Met Glu Met Glu Glu Val Gln Ser Pro Ala Pro Gly Leu Leu Arg
            595                 600                 605 cgg tgc ctg ctt tgg ttc tgt ggg atg agc aag agt ggg tca ggg agt          1874
Arg Cys Leu Leu Trp Phe Cys Gly Met Ser Lys Ser Gly Ser Gly Ser
        610                 615                 620 cct ccg ccc act acc gag gag gtg gcg gca acc acc agg cgg ctg gag          1922
Pro Pro Pro Thr Thr Glu Glu Val Ala Ala Thr Thr Arg Arg Leu Glu
    625                 630                 635 gac atc agt gag gat ccc cgc tgg gca cga gta gtc aac ctc aat gcc          1970
Asp Ile Ser Glu Asp Pro Arg Trp Ala Arg Val Val Asn Leu Asn Ala
```

|     | 640 |     |     | 645 |     |     | 650 |     |     | 655 |     |     |      |
|-----|-----|-----|-----|-----|-----|-----|-----|-----|-----|-----|-----|-----|------|
| cta | ctc | atg | atg | acc | gtg | gct | gtg | ttc | ctc | tgg | ggc | ttc | tat gca taa | 2018 |
| Leu | Leu | Met | Met | Thr | Val | Ala | Val | Phe | Leu | Trp | Gly | Phe | Tyr Ala * |
|     |     |     | 660 |     |     |     |     | 665 |     |     |     | 670 |      |

```
agtcgagggt gttggatgcc atgagctaca accaggccat gttggaccct cacaaagagt    2078
aagggtgagc agcttggagt ggatcccaga aaaggaacag ggcaagaata cagcaggaag    2138
gaaccggttc ccttcctctt tacccggggt ccagtccatt tgattggttg tcacttccca    2198
caagatgatg gccaattggt catagaggtt tgcctataca aaataaaaac tgccctccta    2258
acatcctgtt gtggctgaaa catcgttgct ctcggcttca tcctggtctc tgggctcctg    2318
ttctgggtcc tgggcttgga gcacggttgc tcataagacc ttcttttctg gagacaaggg    2378
ccatgtggcc ctccactcat ccacctctag atggtgtttc tccgtcttcc agccagcagc    2438
ctgcagtcct ttcaa                                                     2453
```

<210> SEQ ID NO 12
<211> LENGTH: 24
<212> TYPE: DNA
<213> ORGANISM: Artificial Sequence
<220> FEATURE:
<223> OTHER INFORMATION: PCR Primer

<400> SEQUENCE: 12
tgttggaccc tcacaaagag taag                                            24

<210> SEQ ID NO 13
<211> LENGTH: 22
<212> TYPE: DNA
<213> ORGANISM: Artificial Sequence
<220> FEATURE:
<223> OTHER INFORMATION: PCR Primer

<400> SEQUENCE: 13
gctgtattct tgccctgttc ct                                              22

<210> SEQ ID NO 14
<211> LENGTH: 26
<212> TYPE: DNA
<213> ORGANISM: Artificial Sequence
<220> FEATURE:
<223> OTHER INFORMATION: PCR Probe

<400> SEQUENCE: 14
ttctgggatc cactccaagc tgctca                                          26

<210> SEQ ID NO 15
<211> LENGTH: 20
<212> TYPE: DNA
<213> ORGANISM: Artificial Sequence
<220> FEATURE:
<223> OTHER INFORMATION: PCR Primer

<400> SEQUENCE: 15
ggcaaattca acggcacagt                                                 20

<210> SEQ ID NO 16
<211> LENGTH: 20
<212> TYPE: DNA
<213> ORGANISM: Artificial Sequence
<220> FEATURE:
<223> OTHER INFORMATION: PCR Primer

<400> SEQUENCE: 16

```
gggtctcgct cctggaagat                                              20

<210> SEQ ID NO 17
<211> LENGTH: 27
<212> TYPE: DNA
<213> ORGANISM: Artificial Sequence
<220> FEATURE:
<223> OTHER INFORMATION: PCR Probe

<400> SEQUENCE: 17
aaggccgaga atgggaagct tgtcatc                                      27

<210> SEQ ID NO 18
<211> LENGTH: 20
<212> TYPE: DNA
<213> ORGANISM: Artificial Sequence
<220> FEATURE:
<223> OTHER INFORMATION: Antisense Compound

<400> SEQUENCE: 18
tctccccagg atctgccccc                                              20

<210> SEQ ID NO 19
<211> LENGTH: 20
<212> TYPE: DNA
<213> ORGANISM: Artificial Sequence
<220> FEATURE:
<223> OTHER INFORMATION: Antisense Compound

<400> SEQUENCE: 19
gtgtgctcct ccattctccc                                              20

<210> SEQ ID NO 20
<211> LENGTH: 20
<212> TYPE: DNA
<213> ORGANISM: Artificial Sequence
<220> FEATURE:
<223> OTHER INFORMATION: Antisense Compound

<400> SEQUENCE: 20
cccatctctg gtgccgagcc                                              20

<210> SEQ ID NO 21
<211> LENGTH: 20
<212> TYPE: DNA
<213> ORGANISM: Artificial Sequence
<220> FEATURE:
<223> OTHER INFORMATION: Antisense Compound

<400> SEQUENCE: 21
aggattgtca atcagggcct                                              20

<210> SEQ ID NO 22
<211> LENGTH: 20
<212> TYPE: DNA
<213> ORGANISM: Artificial Sequence
<220> FEATURE:
<223> OTHER INFORMATION: Antisense Compound

<400> SEQUENCE: 22
atgcagcaat gactaggatg                                              20

<210> SEQ ID NO 23
<211> LENGTH: 20
<212> TYPE: DNA
<213> ORGANISM: Artificial Sequence
<220> FEATURE:
```

<223> OTHER INFORMATION: Antisense Compound

<400> SEQUENCE: 23
caagccaacg ccaatgacca                                          20

<210> SEQ ID NO 24
<211> LENGTH: 20
<212> TYPE: DNA
<213> ORGANISM: Artificial Sequence
<220> FEATURE:
<223> OTHER INFORMATION: Antisense Compound

<400> SEQUENCE: 24
cctctgttgg ttctgcacat                                          20

<210> SEQ ID NO 25
<211> LENGTH: 20
<212> TYPE: DNA
<213> ORGANISM: Artificial Sequence
<220> FEATURE:
<223> OTHER INFORMATION: Antisense Compound

<400> SEQUENCE: 25
tgcgtcctgc caggaagtag                                          20

<210> SEQ ID NO 26
<211> LENGTH: 20
<212> TYPE: DNA
<213> ORGANISM: Artificial Sequence
<220> FEATURE:
<223> OTHER INFORMATION: Antisense Compound

<400> SEQUENCE: 26
ccaaccggcc accacaccat                                          20

<210> SEQ ID NO 27
<211> LENGTH: 20
<212> TYPE: DNA
<213> ORGANISM: Artificial Sequence
<220> FEATURE:
<223> OTHER INFORMATION: Antisense Compound

<400> SEQUENCE: 27
agtccctgcc aggcccacaa                                          20

<210> SEQ ID NO 28
<211> LENGTH: 20
<212> TYPE: DNA
<213> ORGANISM: Artificial Sequence
<220> FEATURE:
<223> OTHER INFORMATION: Antisense Compound

<400> SEQUENCE: 28
ccagcaacag ccaagccact                                          20

<210> SEQ ID NO 29
<211> LENGTH: 20
<212> TYPE: DNA
<213> ORGANISM: Artificial Sequence
<220> FEATURE:
<223> OTHER INFORMATION: Antisense Compound

<400> SEQUENCE: 29
aggtacacgg gtgcaaacag                                          20

<210> SEQ ID NO 30

```
<211> LENGTH: 20
<212> TYPE: DNA
<213> ORGANISM: Artificial Sequence
<220> FEATURE:
<223> OTHER INFORMATION: Antisense Compound

<400> SEQUENCE: 30
tactgtggca tcgtgatgac                                            20

<210> SEQ ID NO 31
<211> LENGTH: 20
<212> TYPE: DNA
<213> ORGANISM: Artificial Sequence
<220> FEATURE:
<223> OTHER INFORMATION: Antisense Compound

<400> SEQUENCE: 31
aggtagaggc ggatgcggcg                                            20

<210> SEQ ID NO 32
<211> LENGTH: 20
<212> TYPE: DNA
<213> ORGANISM: Artificial Sequence
<220> FEATURE:
<223> OTHER INFORMATION: Antisense Compound

<400> SEQUENCE: 32
aagggagagc acagacaggt                                            20

<210> SEQ ID NO 33
<211> LENGTH: 20
<212> TYPE: DNA
<213> ORGANISM: Artificial Sequence
<220> FEATURE:
<223> OTHER INFORMATION: Antisense Compound

<400> SEQUENCE: 33
tccactgaga tcttggtgaa                                            20

<210> SEQ ID NO 34
<211> LENGTH: 20
<212> TYPE: DNA
<213> ORGANISM: Artificial Sequence
<220> FEATURE:
<223> OTHER INFORMATION: Antisense Compound

<400> SEQUENCE: 34
tggatgaata cagctccgga                                            20

<210> SEQ ID NO 35
<211> LENGTH: 20
<212> TYPE: DNA
<213> ORGANISM: Artificial Sequence
<220> FEATURE:
<223> OTHER INFORMATION: Antisense Compound

<400> SEQUENCE: 35
ggcatagatg ttccagccca                                            20

<210> SEQ ID NO 36
<211> LENGTH: 20
<212> TYPE: DNA
<213> ORGANISM: Artificial Sequence
<220> FEATURE:
<223> OTHER INFORMATION: Antisense Compound

<400> SEQUENCE: 36
```

```
tcatggtgat gcccagaagc                                               20

<210> SEQ ID NO 37
<211> LENGTH: 20
<212> TYPE: DNA
<213> ORGANISM: Artificial Sequence
<220> FEATURE:
<223> OTHER INFORMATION: Antisense Compound

<400> SEQUENCE: 37
tcctgtcacc gtgtaaatca                                               20

<210> SEQ ID NO 38
<211> LENGTH: 20
<212> TYPE: DNA
<213> ORGANISM: Artificial Sequence
<220> FEATURE:
<223> OTHER INFORMATION: Antisense Compound

<400> SEQUENCE: 38
gtgtacatca gcgcggccag                                               20

<210> SEQ ID NO 39
<211> LENGTH: 20
<212> TYPE: DNA
<213> ORGANISM: Artificial Sequence
<220> FEATURE:
<223> OTHER INFORMATION: Antisense Compound

<400> SEQUENCE: 39
atgacgaagg tctgtaccgt                                               20

<210> SEQ ID NO 40
<211> LENGTH: 20
<212> TYPE: DNA
<213> ORGANISM: Artificial Sequence
<220> FEATURE:
<223> OTHER INFORMATION: Antisense Compound

<400> SEQUENCE: 40
cccatgagga tgcaggcgcc                                               20

<210> SEQ ID NO 41
<211> LENGTH: 20
<212> TYPE: DNA
<213> ORGANISM: Artificial Sequence
<220> FEATURE:
<223> OTHER INFORMATION: Antisense Compound

<400> SEQUENCE: 41
gtcgaagaga cccgaatacc                                               20

<210> SEQ ID NO 42
<211> LENGTH: 20
<212> TYPE: DNA
<213> ORGANISM: Artificial Sequence
<220> FEATURE:
<223> OTHER INFORMATION: Antisense Compound

<400> SEQUENCE: 42
aagtcgctgc tcccaggtat                                               20

<210> SEQ ID NO 43
<211> LENGTH: 20
<212> TYPE: DNA
<213> ORGANISM: Artificial Sequence
<220> FEATURE:
```

<223> OTHER INFORMATION: Antisense Compound

<400> SEQUENCE: 43
tcgatagcag aagctggaga					20

<210> SEQ ID NO 44
<211> LENGTH: 20
<212> TYPE: DNA
<213> ORGANISM: Artificial Sequence
<220> FEATURE:
<223> OTHER INFORMATION: Antisense Compound

<400> SEQUENCE: 44
agtccgagga gcagcgcggg					20

<210> SEQ ID NO 45
<211> LENGTH: 20
<212> TYPE: DNA
<213> ORGANISM: Artificial Sequence
<220> FEATURE:
<223> OTHER INFORMATION: Antisense Compound

<400> SEQUENCE: 45
ggtcgctgca ccagtaccag					20

<210> SEQ ID NO 46
<211> LENGTH: 20
<212> TYPE: DNA
<213> ORGANISM: Artificial Sequence
<220> FEATURE:
<223> OTHER INFORMATION: Antisense Compound

<400> SEQUENCE: 46
gccaggcagc gctgcacgat					20

<210> SEQ ID NO 47
<211> LENGTH: 20
<212> TYPE: DNA
<213> ORGANISM: Artificial Sequence
<220> FEATURE:
<223> OTHER INFORMATION: Antisense Compound

<400> SEQUENCE: 47
tgcagcccgc cttgatgtgg					20

<210> SEQ ID NO 48
<211> LENGTH: 20
<212> TYPE: DNA
<213> ORGANISM: Artificial Sequence
<220> FEATURE:
<223> OTHER INFORMATION: Antisense Compound

<400> SEQUENCE: 48
ccacacagga tgcagcccgc					20

<210> SEQ ID NO 49
<211> LENGTH: 20
<212> TYPE: DNA
<213> ORGANISM: Artificial Sequence
<220> FEATURE:
<223> OTHER INFORMATION: Antisense Compound

<400> SEQUENCE: 49
catgaccatg agaaacatgg					20

<210> SEQ ID NO 50

```
<211> LENGTH: 20
<212> TYPE: DNA
<213> ORGANISM: Artificial Sequence
<220> FEATURE:
<223> OTHER INFORMATION: Antisense Compound

<400> SEQUENCE: 50
gctgatcatg cctggcatga                                                    20

<210> SEQ ID NO 51
<211> LENGTH: 20
<212> TYPE: DNA
<213> ORGANISM: Artificial Sequence
<220> FEATURE:
<223> OTHER INFORMATION: Antisense Compound

<400> SEQUENCE: 51
cgccacctcg tctgggtaca                                                    20

<210> SEQ ID NO 52
<211> LENGTH: 20
<212> TYPE: DNA
<213> ORGANISM: Artificial Sequence
<220> FEATURE:
<223> OTHER INFORMATION: Antisense Compound

<400> SEQUENCE: 52
cacctcaggc accacgcacg                                                    20

<210> SEQ ID NO 53
<211> LENGTH: 20
<212> TYPE: DNA
<213> ORGANISM: Artificial Sequence
<220> FEATURE:
<223> OTHER INFORMATION: Antisense Compound

<400> SEQUENCE: 53
ccgtgccgca cacgcgcctg                                                    20

<210> SEQ ID NO 54
<211> LENGTH: 20
<212> TYPE: DNA
<213> ORGANISM: Artificial Sequence
<220> FEATURE:
<223> OTHER INFORMATION: Antisense Compound

<400> SEQUENCE: 54
ggtaggcgat gttggagcag                                                    20

<210> SEQ ID NO 55
<211> LENGTH: 20
<212> TYPE: DNA
<213> ORGANISM: Artificial Sequence
<220> FEATURE:
<223> OTHER INFORMATION: Antisense Compound

<400> SEQUENCE: 55
atgagcttca cgacgagccg                                                    20

<210> SEQ ID NO 56
<211> LENGTH: 20
<212> TYPE: DNA
<213> ORGANISM: Artificial Sequence
<220> FEATURE:
<223> OTHER INFORMATION: Antisense Compound

<400> SEQUENCE: 56
```
ccagcatgag tccgcgcaga                                                   20

<210> SEQ ID NO 57
<211> LENGTH: 20
<212> TYPE: DNA
<213> ORGANISM: Artificial Sequence
<220> FEATURE:
<223> OTHER INFORMATION: Antisense Compound

<400> SEQUENCE: 57
cgaggacatg agcgcggcca                                                   20

<210> SEQ ID NO 58
<211> LENGTH: 20
<212> TYPE: DNA
<213> ORGANISM: Artificial Sequence
<220> FEATURE:
<223> OTHER INFORMATION: Antisense Compound

<400> SEQUENCE: 58
gcgtgctgct gctgttgaag                                                   20

<210> SEQ ID NO 59
<211> LENGTH: 20
<212> TYPE: DNA
<213> ORGANISM: Artificial Sequence
<220> FEATURE:
<223> OTHER INFORMATION: Antisense Compound

<400> SEQUENCE: 59
tgtagatgtc catggtgaag                                                   20

<210> SEQ ID NO 60
<211> LENGTH: 20
<212> TYPE: DNA
<213> ORGANISM: Artificial Sequence
<220> FEATURE:
<223> OTHER INFORMATION: Antisense Compound

<400> SEQUENCE: 60
agcagcagct cgcggtcgcc                                                   20

<210> SEQ ID NO 61
<211> LENGTH: 20
<212> TYPE: DNA
<213> ORGANISM: Artificial Sequence
<220> FEATURE:
<223> OTHER INFORMATION: Antisense Compound

<400> SEQUENCE: 61
ccacccagag ccgtcccacc                                                   20

<210> SEQ ID NO 62
<211> LENGTH: 20
<212> TYPE: DNA
<213> ORGANISM: Artificial Sequence
<220> FEATURE:
<223> OTHER INFORMATION: Antisense Compound

<400> SEQUENCE: 62
aggccaccga cactaccacg                                                   20

<210> SEQ ID NO 63
<211> LENGTH: 20
<212> TYPE: DNA
<213> ORGANISM: Artificial Sequence
<220> FEATURE:

```
<223> OTHER INFORMATION: Antisense Compound

<400> SEQUENCE: 63
gaagagctgc ccgccctgtg                                           20

<210> SEQ ID NO 64
<211> LENGTH: 20
<212> TYPE: DNA
<213> ORGANISM: Artificial Sequence
<220> FEATURE:
<223> OTHER INFORMATION: Antisense Compound

<400> SEQUENCE: 64
ctggatgtaa tcgaagagct                                           20

<210> SEQ ID NO 65
<211> LENGTH: 20
<212> TYPE: DNA
<213> ORGANISM: Artificial Sequence
<220> FEATURE:
<223> OTHER INFORMATION: Antisense Compound

<400> SEQUENCE: 65
cgaagacggc ggacacgggc                                           20

<210> SEQ ID NO 66
<211> LENGTH: 20
<212> TYPE: DNA
<213> ORGANISM: Artificial Sequence
<220> FEATURE:
<223> OTHER INFORMATION: Antisense Compound

<400> SEQUENCE: 66
gcacgaagag cgccagcacg                                           20

<210> SEQ ID NO 67
<211> LENGTH: 20
<212> TYPE: DNA
<213> ORGANISM: Artificial Sequence
<220> FEATURE:
<223> OTHER INFORMATION: Antisense Compound

<400> SEQUENCE: 67
gccctgctca ttaacgcgcg                                           20

<210> SEQ ID NO 68
<211> LENGTH: 20
<212> TYPE: DNA
<213> ORGANISM: Artificial Sequence
<220> FEATURE:
<223> OTHER INFORMATION: Antisense Compound

<400> SEQUENCE: 68
aggcccccga tgagtcccca                                           20

<210> SEQ ID NO 69
<211> LENGTH: 20
<212> TYPE: DNA
<213> ORGANISM: Artificial Sequence
<220> FEATURE:
<223> OTHER INFORMATION: Antisense Compound

<400> SEQUENCE: 69
cgtgccaggc ccatcagcag                                           20

<210> SEQ ID NO 70
```

```
<211> LENGTH: 20
<212> TYPE: DNA
<213> ORGANISM: Artificial Sequence
<220> FEATURE:
<223> OTHER INFORMATION: Antisense Compound

<400> SEQUENCE: 70
ccgagccgaa ggagaactcg                                             20

<210> SEQ ID NO 71
<211> LENGTH: 20
<212> TYPE: DNA
<213> ORGANISM: Artificial Sequence
<220> FEATURE:
<223> OTHER INFORMATION: Antisense Compound

<400> SEQUENCE: 71
agggctgcac acagctgccc                                             20

<210> SEQ ID NO 72
<211> LENGTH: 20
<212> TYPE: DNA
<213> ORGANISM: Artificial Sequence
<220> FEATURE:
<223> OTHER INFORMATION: Antisense Compound

<400> SEQUENCE: 72
gccgcagagg aaagctgggc                                             20

<210> SEQ ID NO 73
<211> LENGTH: 20
<212> TYPE: DNA
<213> ORGANISM: Artificial Sequence
<220> FEATURE:
<223> OTHER INFORMATION: Antisense Compound

<400> SEQUENCE: 73
caatggcgaa gtagaggtag                                             20

<210> SEQ ID NO 74
<211> LENGTH: 20
<212> TYPE: DNA
<213> ORGANISM: Artificial Sequence
<220> FEATURE:
<223> OTHER INFORMATION: Antisense Compound

<400> SEQUENCE: 74
gccagagcag aagaacagca                                             20

<210> SEQ ID NO 75
<211> LENGTH: 20
<212> TYPE: DNA
<213> ORGANISM: Artificial Sequence
<220> FEATURE:
<223> OTHER INFORMATION: Antisense Compound

<400> SEQUENCE: 75
cacagggaga ccgtgagggt                                             20

<210> SEQ ID NO 76
<211> LENGTH: 20
<212> TYPE: DNA
<213> ORGANISM: Artificial Sequence
<220> FEATURE:
<223> OTHER INFORMATION: Antisense Compound

<400> SEQUENCE: 76
```
aggcggtgga ggtgctttct                                                20

<210> SEQ ID NO 77
<211> LENGTH: 20
<212> TYPE: DNA
<213> ORGANISM: Artificial Sequence
<220> FEATURE:
<223> OTHER INFORMATION: Antisense Compound

<400> SEQUENCE: 77
cctccttgct atgccggaga                                                20

<210> SEQ ID NO 78
<211> LENGTH: 20
<212> TYPE: DNA
<213> ORGANISM: Artificial Sequence
<220> FEATURE:
<223> OTHER INFORMATION: Antisense Compound

<400> SEQUENCE: 78
atcagcatcc aggtcctccc                                                20

<210> SEQ ID NO 79
<211> LENGTH: 20
<212> TYPE: DNA
<213> ORGANISM: Artificial Sequence
<220> FEATURE:
<223> OTHER INFORMATION: Antisense Compound

<400> SEQUENCE: 79
cattctgtac agggagtgag                                                20

<210> SEQ ID NO 80
<211> LENGTH: 20
<212> TYPE: DNA
<213> ORGANISM: Artificial Sequence
<220> FEATURE:
<223> OTHER INFORMATION: Antisense Compound

<400> SEQUENCE: 80
atctccatgg cactctctgg                                                20

<210> SEQ ID NO 81
<211> LENGTH: 20
<212> TYPE: DNA
<213> ORGANISM: Artificial Sequence
<220> FEATURE:
<223> OTHER INFORMATION: Antisense Compound

<400> SEQUENCE: 81
gcaggcactg gcggaagagg                                                20

<210> SEQ ID NO 82
<211> LENGTH: 20
<212> TYPE: DNA
<213> ORGANISM: Artificial Sequence
<220> FEATURE:
<223> OTHER INFORMATION: Antisense Compound

<400> SEQUENCE: 82
acctctgctc attccacaaa                                                20

<210> SEQ ID NO 83
<211> LENGTH: 20
<212> TYPE: DNA
<213> ORGANISM: Artificial Sequence
<220> FEATURE:

<223> OTHER INFORMATION: Antisense Compound

<400> SEQUENCE: 83
ggcggaggac tgcccacccc                                               20

<210> SEQ ID NO 84
<211> LENGTH: 20
<212> TYPE: DNA
<213> ORGANISM: Artificial Sequence
<220> FEATURE:
<223> OTHER INFORMATION: Antisense Compound

<400> SEQUENCE: 84
cgcctggctg ctgccgctgc                                               20

<210> SEQ ID NO 85
<211> LENGTH: 20
<212> TYPE: DNA
<213> ORGANISM: Artificial Sequence
<220> FEATURE:
<223> OTHER INFORMATION: Antisense Compound

<400> SEQUENCE: 85
gtcctcgctg atgtcctcca                                               20

<210> SEQ ID NO 86
<211> LENGTH: 20
<212> TYPE: DNA
<213> ORGANISM: Artificial Sequence
<220> FEATURE:
<223> OTHER INFORMATION: Antisense Compound

<400> SEQUENCE: 86
ggcattgagg ttgaccacac                                               20

<210> SEQ ID NO 87
<211> LENGTH: 20
<212> TYPE: DNA
<213> ORGANISM: Artificial Sequence
<220> FEATURE:
<223> OTHER INFORMATION: Antisense Compound

<400> SEQUENCE: 87
agaggaacac ggccactgcc                                               20

<210> SEQ ID NO 88
<211> LENGTH: 20
<212> TYPE: DNA
<213> ORGANISM: Artificial Sequence
<220> FEATURE:
<223> OTHER INFORMATION: Antisense Compound

<400> SEQUENCE: 88
atagaagccc cagaggaaca                                               20

<210> SEQ ID NO 89
<211> LENGTH: 20
<212> TYPE: DNA
<213> ORGANISM: Artificial Sequence
<220> FEATURE:
<223> OTHER INFORMATION: Antisense Compound

<400> SEQUENCE: 89
tggtcttagg catagaagcc                                               20

<210> SEQ ID NO 90

-continued

```
<211> LENGTH: 20
<212> TYPE: DNA
<213> ORGANISM: Artificial Sequence
<220> FEATURE:
<223> OTHER INFORMATION: Antisense Compound

<400> SEQUENCE: 90
tggcttatgg tgtccaacgc                                                  20

<210> SEQ ID NO 91
<211> LENGTH: 20
<212> TYPE: DNA
<213> ORGANISM: Artificial Sequence
<220> FEATURE:
<223> OTHER INFORMATION: Antisense Compound

<400> SEQUENCE: 91
tcacccccac ttcctgtgag                                                  20

<210> SEQ ID NO 92
<211> LENGTH: 20
<212> TYPE: DNA
<213> ORGANISM: Artificial Sequence
<220> FEATURE:
<223> OTHER INFORMATION: Antisense Compound

<400> SEQUENCE: 92
tctcacccca ctgccccttc                                                  20

<210> SEQ ID NO 93
<211> LENGTH: 20
<212> TYPE: DNA
<213> ORGANISM: Artificial Sequence
<220> FEATURE:
<223> OTHER INFORMATION: Antisense Compound

<400> SEQUENCE: 93
caggcagagg aaggccggga                                                  20

<210> SEQ ID NO 94
<211> LENGTH: 20
<212> TYPE: DNA
<213> ORGANISM: Artificial Sequence
<220> FEATURE:
<223> OTHER INFORMATION: Antisense Compound

<400> SEQUENCE: 94
cctcatggga agtgactgcc                                                  20

<210> SEQ ID NO 95
<211> LENGTH: 20
<212> TYPE: DNA
<213> ORGANISM: Artificial Sequence
<220> FEATURE:
<223> OTHER INFORMATION: Antisense Compound

<400> SEQUENCE: 95
ttccttaggg caactgcagc                                                  20

<210> SEQ ID NO 96
<211> LENGTH: 3300
<212> TYPE: DNA
<213> ORGANISM: M. musculus
<220> FEATURE:

<400> SEQUENCE: 96
tacatcaatg gaatttaaat agagtcgtca tataataagg gaaacaatgt cccaactgga      60
```

```
catcacatgg taccaaacaa aagacccagt accaggaatg agttaccatc ttatgaagtc      120
attaaccata gagagctaat ggtagcctca atcattacaa aagctgttgc caaggttact      180
gggtgctctc atacctgat ggtaagaccc tatggctgaa gatggaactt attgatatcc       240
ttgaacattg agaaattgag ctgtgtgact agaagcttca ccccatcgac gatggtcaca      300
gtgctgcaaa gtgctatgtt caggaggaag gtatccagcc gcctccctca gccacactct      360
gagactcaca ccagagacct gctcaaaggg catgcccact ggcccacaaa tattatggga      420
gcaactgacc acttttggg ggtgtattta aggtccactt catgaaatgg gacccatccc       480
tgacactgct aaaatgcctg agaacctgaa actagataga gcaagggctc taggggaaag      540
ctcactccag ttattctaag ggcacagggt tatgacgcct aatgacatat cgctggctac      600
atcccttggc cagcacatca ctgaaacctc accagaggag cttcttggag tagaaggtga      660
ttaacagaac tgtccgtgac tggatgactt gcagagagtg agagacttgg gagcactcag      720
acttcaatgg gatgcttgta tctcacccct ctgctaaaga tgcaggttct atacaggagg      780
tgcaaagatt gtaagagtca gagttggagg ttgtcttcag gaaagcagag ttttgcagac      840
acaacaaagc tgatgaaaat ctgaactcac agacagtgat agcatgcaca agacagatat      900
ctgaactcac agaccgtgat aacatggcac aaagacctgc acaagttcg aaccaaataa       960 aatctgagca tggaaaatga ggtgtgggca caagtccca ctcctaagta agaaactact      1020
tgcagttgac agctactagg agagagaaat gggttttctt caatggagag acactgggtg     1080
tatcaactgc accccaaggc aggccacacg ctcaggaaga gttggccaac acaaaacaca     1140
ctccgtgttt ggttttctgt ttgcttgggt ttgttttgt gcttttattc ttccttcctt      1200
tctttctttg tttctttgtt tctctctctc tttctctctt tttctctctc cctcctcctc     1260
ttcttctttc ttcttttctt tcttcttctt cttcttcttc ttttcttct tcttcttctt      1320 cttttcttc ttcttcttct tcttcttctt cttcttcttc ttcttcttct tcttcttctt      1380
cttcttcttc ttcttcttct tctgatcaga gaggggaggg gatctgggaa aagtttgggg     1440
agaggaaaga atttgcccaa aatatattgc ataaaaactt tttaaaaata aatttaaaac     1500 aattttttagg atagagcaaa gagaaagtag aaaatatttg ggttgggaag ggcaggagaa    1560
tgagggaaat gtgatttttt tctccctagg ttttgtatgg cagaagtcag ggcatggcat     1620
gcgtgacagt caggctgagg aacatgtatg tcctgctgac tgtcagggggg tgctatggag    1680 gacttgtgcg gaggacactg tcagagttgg attcggacct tcctaatcaa agttagaggg     1740
tgtattttca gagaacgcag gaaggaactt tgcttggaac actgggtata ggatggatcc     1800
taaacccagg aaggagtgct cttgaattcc aaatggtcca gcgccccagg accagccttc     1860
ggccttgata gatcctgatt cagataaata aagctggaga aggaggctga gacctggggg     1920
acttgtcggg tcagtgctcc tgaggtaacc attaatcctt ccccagggg aatccaggga     1980 ctagcccctt gagggacaga tggtggagag aatggagcaa cacgtagagg caggctctga    2040 acttgggag cagaaggtcc tgattgataa tcctgctgac attctggtta tcgctgccta     2100
tttcctgctg gtcattggtg ttggcttgtg ggtgagacat tgaggggggt tggatagggga    2160 aatgcttctg gggcttgagg gtaaagattt agggagacct cagagaggag tgggagaaaa    2220
gggtgcttgg atataatgag ggagaaacct agatttagta ggcaagccaa ttttaattct    2280
ttgtcttcgt accttctgga ttgtgcaaaa gagactgggg gtatcaatag gttttttttt    2340
aattcaagtg ttctaacaag tgctctaaga gatgtatcga ttcccacgtc tgtattatgg    2400
ctgagcagca gcctatattt aaggtcacca ggcaagttag gctgaatcta ggcatatcta    2460
```

```
ggttccagta gttgcgctag gattagggcc tgggttgttc tgagtgtcgg ggaaggttgg      2520
gggtaaggag gtgcagtctg gggagtccag ggctggttaa tcttcagcct gaaacaaggc      2580
tgaggaatgt gttgaggaag ctaaggaagt ccaaagatgt gccccaatcc cagtttcccc      2640
ccacttctgt ttcccagtct atgttcagaa ccaatagagg cacagttggt ggctacttcc      2700
tggcaggacg gaacatggtg tggtggccgg tgagaggggc tggggatgg gatgggaggg       2760 accctggagg agcaccctac ctcaccccca tttctggcca cccaggttgg agcctctctg      2820
ttcgccagca acatcggcag cggtcatttt gtgggcctgg cagggactgg tgcagcaagt      2880
ggcttggcgg tggctggatt tgagtggaat gtgaggtctt cttttctata ataatccacc      2940
ccagtggaaa ctcctggaaa gatcacaact tggggaagct cctggcgtgg ggatatgaac      3000
aagttgggac agcacagttt gctgagggtg ggtgggtgtt aggttgggct gggagcaagg      3060
atcgcgtgct agcttacagc agtagggttc aggcaggtcc tgctcctgac tttctgtata      3120
cgccagcatc agtcctcgtg ggccttgacc actctgaaat ggggccggca cctcactgat      3180
gaagtacctg tctccatgtt ctttgatgct gtagtctgtg agcaactcta ggctgaactg      3240
aagttctttg caaaaacaag gatgggttgg aaagatgagg gtttgagcct tcctgtaaga      3300

<210> SEQ ID NO 97
<211> LENGTH: 769
<212> TYPE: DNA
<213> ORGANISM: M. musculus
<220> FEATURE:
<221> NAME/KEY: misc_feature
<222> LOCATION: 598
<223> OTHER INFORMATION: n = A, T, C or G

<400> SEQUENCE: 97
aaagatgagg gtttgagcct tcctgtaaga ggccttagaa ctgagactat gagggtaaaa       60
ttcttgggcc aggtggagga ggggaggcag ccctgcctgg cagatgctga ggtcagtctg      120
aagagtctgt gcacacaggt tcatttgctg gagagacagg gaggggccat aacgaccttg      180
gaggagacta gttagaggtg atggtctgta cgcgcaaaaa gggctctctc tatatagtta      240
aggtgccggg aagatgtcaa gattctttcc cttcctgtcc agggcccagg cacttccgct      300
gtgtcttctg ggtcctgggt gtgaggacta ggacaggcct gctcaggatg ctgtcccggg      360
ccgtcatttg ttcccacagg cgctcttcgt ggtgctgctc ctcggatggc tttttgtgcc      420
agtgtatctg accgctggtg tgatcacaat gcctcagtac ctccgcaagc gctttggtgg      480
gcaccgtatt cgcctctacc tgtccgtgct ctcgcttttt ttgtacattt tcaccaagat      540
ctcggtggat atgttctctg gggcagtatt cattcaacag gccctgggct ggaacatnta      600
cgcttcggtc atcgctctct tgggcatcac catgatttat actgtgacag ggaggctggc      660
ggcactgatg tacacagaca ctgtgcagac cttcgtcatt cttttgccggg ccttcatcct      720 cactggtatg ctttccatga agtgggcggg tactcggtct cttcgacaa                  769

<210> SEQ ID NO 98
<211> LENGTH: 20
<212> TYPE: DNA
<213> ORGANISM: Artificial Sequence
<220> FEATURE:
<223> OTHER INFORMATION: Antisense Compound

<400> SEQUENCE: 98 tgctcccaa gttcagagcc                                                    20
```

```
<210> SEQ ID NO 99
<211> LENGTH: 20
<212> TYPE: DNA
<213> ORGANISM: Artificial Sequence
<220> FEATURE:
<223> OTHER INFORMATION: Antisense Compound

<400> SEQUENCE: 99
atcaggacct tctgctcccc                                               20

<210> SEQ ID NO 100
<211> LENGTH: 20
<212> TYPE: DNA
<213> ORGANISM: Artificial Sequence
<220> FEATURE:
<223> OTHER INFORMATION: Antisense Compound

<400> SEQUENCE: 100
caggattatc aatcaggacc                                               20

<210> SEQ ID NO 101
<211> LENGTH: 20
<212> TYPE: DNA
<213> ORGANISM: Artificial Sequence
<220> FEATURE:
<223> OTHER INFORMATION: Antisense Compound

<400> SEQUENCE: 101
ccagaatgtc agcaggatta                                               20

<210> SEQ ID NO 102
<211> LENGTH: 20
<212> TYPE: DNA
<213> ORGANISM: Artificial Sequence
<220> FEATURE:
<223> OTHER INFORMATION: Antisense Compound

<400> SEQUENCE: 102
ccaatgacca gcaggaaata                                               20

<210> SEQ ID NO 103
<211> LENGTH: 20
<212> TYPE: DNA
<213> ORGANISM: Artificial Sequence
<220> FEATURE:
<223> OTHER INFORMATION: Antisense Compound

<400> SEQUENCE: 103
ctgaacatag accacaagcc                                               20

<210> SEQ ID NO 104
<211> LENGTH: 20
<212> TYPE: DNA
<213> ORGANISM: Artificial Sequence
<220> FEATURE:
<223> OTHER INFORMATION: Antisense Compound

<400> SEQUENCE: 104
tctattggtt ctgaacatag                                               20

<210> SEQ ID NO 105
<211> LENGTH: 20
<212> TYPE: DNA
<213> ORGANISM: Artificial Sequence
<220> FEATURE:
<223> OTHER INFORMATION: Antisense Compound

<400> SEQUENCE: 105
```
ccaactgtgc ctctattggt                                               20

<210> SEQ ID NO 106
<211> LENGTH: 20
<212> TYPE: DNA
<213> ORGANISM: Artificial Sequence
<220> FEATURE:
<223> OTHER INFORMATION: Antisense Compound

<400> SEQUENCE: 106
gaagtagcca ccaactgtgc                                               20

<210> SEQ ID NO 107
<211> LENGTH: 20
<212> TYPE: DNA
<213> ORGANISM: Artificial Sequence
<220> FEATURE:
<223> OTHER INFORMATION: Antisense Compound

<400> SEQUENCE: 107
gaggctccaa ccggccacca                                               20

<210> SEQ ID NO 108
<211> LENGTH: 20
<212> TYPE: DNA
<213> ORGANISM: Artificial Sequence
<220> FEATURE:
<223> OTHER INFORMATION: Antisense Compound

<400> SEQUENCE: 108
ctgccgatgt tgctggcgaa                                               20

<210> SEQ ID NO 109
<211> LENGTH: 20
<212> TYPE: DNA
<213> ORGANISM: Artificial Sequence
<220> FEATURE:
<223> OTHER INFORMATION: Antisense Compound

<400> SEQUENCE: 109
ggcccacaaa atgaccgctg                                               20

<210> SEQ ID NO 110
<211> LENGTH: 20
<212> TYPE: DNA
<213> ORGANISM: Artificial Sequence
<220> FEATURE:
<223> OTHER INFORMATION: Antisense Compound

<400> SEQUENCE: 110
gccaagccac ttgctgcacc                                               20

<210> SEQ ID NO 111
<211> LENGTH: 20
<212> TYPE: DNA
<213> ORGANISM: Artificial Sequence
<220> FEATURE:
<223> OTHER INFORMATION: Antisense Compound

<400> SEQUENCE: 111
acgaagagcg cattccactc                                               20

<210> SEQ ID NO 112
<211> LENGTH: 20
<212> TYPE: DNA
<213> ORGANISM: Artificial Sequence

```
<220> FEATURE:
<223> OTHER INFORMATION: Antisense Compound

<400> SEQUENCE: 112
gcaccacgaa gagcgcattc                                               20

<210> SEQ ID NO 113
<211> LENGTH: 20
<212> TYPE: DNA
<213> ORGANISM: Artificial Sequence
<220> FEATURE:
<223> OTHER INFORMATION: Antisense Compound

<400> SEQUENCE: 113
cgcttgcgga ggtactgagg                                               20

<210> SEQ ID NO 114
<211> LENGTH: 20
<212> TYPE: DNA
<213> ORGANISM: Artificial Sequence
<220> FEATURE:
<223> OTHER INFORMATION: Antisense Compound

<400> SEQUENCE: 114
agcgagagca cggacaggta                                               20

<210> SEQ ID NO 115
<211> LENGTH: 20
<212> TYPE: DNA
<213> ORGANISM: Artificial Sequence
<220> FEATURE:
<223> OTHER INFORMATION: Antisense Compound

<400> SEQUENCE: 115
gagaacatat ccaccgagat                                               20

<210> SEQ ID NO 116
<211> LENGTH: 20
<212> TYPE: DNA
<213> ORGANISM: Artificial Sequence
<220> FEATURE:
<223> OTHER INFORMATION: Antisense Compound

<400> SEQUENCE: 116
cagggcctgt tgaatgaata                                               20

<210> SEQ ID NO 117
<211> LENGTH: 20
<212> TYPE: DNA
<213> ORGANISM: Artificial Sequence
<220> FEATURE:
<223> OTHER INFORMATION: Antisense Compound

<400> SEQUENCE: 117
cacagtataa atcatggtga                                               20

<210> SEQ ID NO 118
<211> LENGTH: 20
<212> TYPE: DNA
<213> ORGANISM: Artificial Sequence
<220> FEATURE:
<223> OTHER INFORMATION: Antisense Compound

<400> SEQUENCE: 118
ctgtgtacat cagtgccgcc                                               20
```

-continued

```
<210> SEQ ID NO 119
<211> LENGTH: 20
<212> TYPE: DNA
<213> ORGANISM: Artificial Sequence
<220> FEATURE:
<223> OTHER INFORMATION: Antisense Compound

<400> SEQUENCE: 119
ctgcacagtg tctgtgtaca                                            20

<210> SEQ ID NO 120
<211> LENGTH: 20
<212> TYPE: DNA
<213> ORGANISM: Artificial Sequence
<220> FEATURE:
<223> OTHER INFORMATION: Antisense Compound

<400> SEQUENCE: 120
gaatgacgaa ggtctgcaca                                            20

<210> SEQ ID NO 121
<211> LENGTH: 20
<212> TYPE: DNA
<213> ORGANISM: Artificial Sequence
<220> FEATURE:
<223> OTHER INFORMATION: Antisense Compound

<400> SEQUENCE: 121
ggccccggca agaatgacga                                            20

<210> SEQ ID NO 122
<211> LENGTH: 20
<212> TYPE: DNA
<213> ORGANISM: Artificial Sequence
<220> FEATURE:
<223> OTHER INFORMATION: Antisense Compound

<400> SEQUENCE: 122
agtacccgcc cacttcatgg                                            20

<210> SEQ ID NO 123
<211> LENGTH: 20
<212> TYPE: DNA
<213> ORGANISM: Artificial Sequence
<220> FEATURE:
<223> OTHER INFORMATION: Antisense Compound

<400> SEQUENCE: 123
acccgtcagt gaagtcattg                                            20

<210> SEQ ID NO 124
<211> LENGTH: 20
<212> TYPE: DNA
<213> ORGANISM: Artificial Sequence
<220> FEATURE:
<223> OTHER INFORMATION: Antisense Compound

<400> SEQUENCE: 124
gtcacgcagc aggtgatagg                                            20

<210> SEQ ID NO 125
<211> LENGTH: 20
<212> TYPE: DNA
<213> ORGANISM: Artificial Sequence
<220> FEATURE:
<223> OTHER INFORMATION: Antisense Compound

<400> SEQUENCE: 125
```
cctgtcacag ggtcacgcag                                                      20

<210> SEQ ID NO 126
<211> LENGTH: 20
<212> TYPE: DNA
<213> ORGANISM: Artificial Sequence
<220> FEATURE:
<223> OTHER INFORMATION: Antisense Compound

<400> SEQUENCE: 126
gagacaatgg taagccccag                                                      20

<210> SEQ ID NO 127
<211> LENGTH: 20
<212> TYPE: DNA
<213> ORGANISM: Artificial Sequence
<220> FEATURE:
<223> OTHER INFORMATION: Antisense Compound

<400> SEQUENCE: 127
tcagattctt tccagccagg                                                      20

<210> SEQ ID NO 128
<211> LENGTH: 20
<212> TYPE: DNA
<213> ORGANISM: Artificial Sequence
<220> FEATURE:
<223> OTHER INFORMATION: Antisense Compound

<400> SEQUENCE: 128
ttgatgtgag tcagattctt                                                      20

<210> SEQ ID NO 129
<211> LENGTH: 20
<212> TYPE: DNA
<213> ORGANISM: Artificial Sequence
<220> FEATURE:
<223> OTHER INFORMATION: Antisense Compound

<400> SEQUENCE: 129
ggtagagaat gcggctgatc                                                      20

<210> SEQ ID NO 130
<211> LENGTH: 20
<212> TYPE: DNA
<213> ORGANISM: Artificial Sequence
<220> FEATURE:
<223> OTHER INFORMATION: Antisense Compound

<400> SEQUENCE: 130
ccgcttacac acctcaggta                                                      20

<210> SEQ ID NO 131
<211> LENGTH: 20
<212> TYPE: DNA
<213> ORGANISM: Artificial Sequence
<220> FEATURE:
<223> OTHER INFORMATION: Antisense Compound

<400> SEQUENCE: 131
gtgccacaca cccgcttaca                                                      20

<210> SEQ ID NO 132
<211> LENGTH: 20
<212> TYPE: DNA
<213> ORGANISM: Artificial Sequence

```
<220> FEATURE:
<223> OTHER INFORMATION: Antisense Compound

<400> SEQUENCE: 132
ttagagcagc ccacctcagt                                               20

<210> SEQ ID NO 133
<211> LENGTH: 20
<212> TYPE: DNA
<213> ORGANISM: Artificial Sequence
<220> FEATURE:
<223> OTHER INFORMATION: Antisense Compound

<400> SEQUENCE: 133
tgggtaggcg atgttagagc                                               20

<210> SEQ ID NO 134
<211> LENGTH: 20
<212> TYPE: DNA
<213> ORGANISM: Artificial Sequence
<220> FEATURE:
<223> OTHER INFORMATION: Antisense Compound

<400> SEQUENCE: 134
agaccattgg gcatgagctt                                               20

<210> SEQ ID NO 135
<211> LENGTH: 20
<212> TYPE: DNA
<213> ORGANISM: Artificial Sequence
<220> FEATURE:
<223> OTHER INFORMATION: Antisense Compound

<400> SEQUENCE: 135
agcatgagtc cgcgcagacc                                               20

<210> SEQ ID NO 136
<211> LENGTH: 20
<212> TYPE: DNA
<213> ORGANISM: Artificial Sequence
<220> FEATURE:
<223> OTHER INFORMATION: Antisense Compound

<400> SEQUENCE: 136
ccagcatgac tgccagcatg                                               20

<210> SEQ ID NO 137
<211> LENGTH: 20
<212> TYPE: DNA
<213> ORGANISM: Artificial Sequence
<220> FEATURE:
<223> OTHER INFORMATION: Antisense Compound

<400> SEQUENCE: 137
gttaaagatg gatgccagag                                               20

<210> SEQ ID NO 138
<211> LENGTH: 20
<212> TYPE: DNA
<213> ORGANISM: Artificial Sequence
<220> FEATURE:
<223> OTHER INFORMATION: Antisense Compound

<400> SEQUENCE: 138
cagctcctta tcacctgcac                                               20
```

```
<210> SEQ ID NO 139
<211> LENGTH: 20
<212> TYPE: DNA
<213> ORGANISM: Artificial Sequence
<220> FEATURE:
<223> OTHER INFORMATION: Antisense Compound

<400> SEQUENCE: 139
gctgcctgca ccactggcag                                              20

<210> SEQ ID NO 140
<211> LENGTH: 20
<212> TYPE: DNA
<213> ORGANISM: Artificial Sequence
<220> FEATURE:
<223> OTHER INFORMATION: Antisense Compound

<400> SEQUENCE: 140
aaagaccgca gacacttgag                                              20

<210> SEQ ID NO 141
<211> LENGTH: 20
<212> TYPE: DNA
<213> ORGANISM: Artificial Sequence
<220> FEATURE:
<223> OTHER INFORMATION: Antisense Compound

<400> SEQUENCE: 141
gtgcaagcac aaagaccgca                                              20

<210> SEQ ID NO 142
<211> LENGTH: 20
<212> TYPE: DNA
<213> ORGANISM: Artificial Sequence
<220> FEATURE:
<223> OTHER INFORMATION: Antisense Compound

<400> SEQUENCE: 142
gagctaggcc catcagcagg                                              20

<210> SEQ ID NO 143
<211> LENGTH: 20
<212> TYPE: DNA
<213> ORGANISM: Artificial Sequence
<220> FEATURE:
<223> OTHER INFORMATION: Antisense Compound

<400> SEQUENCE: 143
ggtatgagac gagctaggcc                                              20

<210> SEQ ID NO 144
<211> LENGTH: 20
<212> TYPE: DNA
<213> ORGANISM: Artificial Sequence
<220> FEATURE:
<223> OTHER INFORMATION: Antisense Compound

<400> SEQUENCE: 144
agaagaactc gggtatgaga                                              20

<210> SEQ ID NO 145
<211> LENGTH: 20
<212> TYPE: DNA
<213> ORGANISM: Artificial Sequence
<220> FEATURE:
<223> OTHER INFORMATION: Antisense Compound

<400> SEQUENCE: 145
```

```
gagggtcgca cacagctgcc                                                    20

<210> SEQ ID NO 146
<211> LENGTH: 20
<212> TYPE: DNA
<213> ORGANISM: Artificial Sequence
<220> FEATURE:
<223> OTHER INFORMATION: Antisense Compound

<400> SEQUENCE: 146
tagaggtagt gtacccgaca                                                    20

<210> SEQ ID NO 147
<211> LENGTH: 20
<212> TYPE: DNA
<213> ORGANISM: Artificial Sequence
<220> FEATURE:
<223> OTHER INFORMATION: Antisense Compound

<400> SEQUENCE: 147
ccttgctgtg ccggagactg                                                    20

<210> SEQ ID NO 148
<211> LENGTH: 20
<212> TYPE: DNA
<213> ORGANISM: Artificial Sequence
<220> FEATURE:
<223> OTHER INFORMATION: Antisense Compound

<400> SEQUENCE: 148
tcagcatcca ggtcctcccg                                                    20

<210> SEQ ID NO 149
<211> LENGTH: 20
<212> TYPE: DNA
<213> ORGANISM: Artificial Sequence
<220> FEATURE:
<223> OTHER INFORMATION: Antisense Compound

<400> SEQUENCE: 149
ggaccttcta actcatcagc                                                    20

<210> SEQ ID NO 150
<211> LENGTH: 20
<212> TYPE: DNA
<213> ORGANISM: Artificial Sequence
<220> FEATURE:
<223> OTHER INFORMATION: Antisense Compound

<400> SEQUENCE: 150
cattgcacat tcctggcccc                                                    20

<210> SEQ ID NO 151
<211> LENGTH: 20
<212> TYPE: DNA
<213> ORGANISM: Artificial Sequence
<220> FEATURE:
<223> OTHER INFORMATION: Antisense Compound

<400> SEQUENCE: 151
ttgctcatcc cacagaacca                                                    20

<210> SEQ ID NO 152
<211> LENGTH: 20
<212> TYPE: DNA
<213> ORGANISM: Artificial Sequence
```

-continued

<220> FEATURE:
<223> OTHER INFORMATION: Antisense Compound

<400> SEQUENCE: 152
cctgacccac tcttgctcat                                          20

<210> SEQ ID NO 153
<211> LENGTH: 20
<212> TYPE: DNA
<213> ORGANISM: Artificial Sequence
<220> FEATURE:
<223> OTHER INFORMATION: Antisense Compound

<400> SEQUENCE: 153
gccacctcct cggtagtggg                                          20

<210> SEQ ID NO 154
<211> LENGTH: 20
<212> TYPE: DNA
<213> ORGANISM: Artificial Sequence
<220> FEATURE:
<223> OTHER INFORMATION: Antisense Compound

<400> SEQUENCE: 154
gatgtcctcc agccgcctgg                                          20

<210> SEQ ID NO 155
<211> LENGTH: 20
<212> TYPE: DNA
<213> ORGANISM: Artificial Sequence
<220> FEATURE:
<223> OTHER INFORMATION: Antisense Compound

<400> SEQUENCE: 155
gggatcctca ctgatgtcct                                          20

<210> SEQ ID NO 156
<211> LENGTH: 20
<212> TYPE: DNA
<213> ORGANISM: Artificial Sequence
<220> FEATURE:
<223> OTHER INFORMATION: Antisense Compound

<400> SEQUENCE: 156
agggcattga ggttgactac                                          20

<210> SEQ ID NO 157
<211> LENGTH: 20
<212> TYPE: DNA
<213> ORGANISM: Artificial Sequence
<220> FEATURE:
<223> OTHER INFORMATION: Antisense Compound

<400> SEQUENCE: 157
tagaagcccc agaggaacac                                          20

<210> SEQ ID NO 158
<211> LENGTH: 20
<212> TYPE: DNA
<213> ORGANISM: Artificial Sequence
<220> FEATURE:
<223> OTHER INFORMATION: Antisense Compound

<400> SEQUENCE: 158
aatcaaatgg actggacccc                                          20

```
<210> SEQ ID NO 159
<211> LENGTH: 20
<212> TYPE: DNA
<213> ORGANISM: Artificial Sequence
<220> FEATURE:
<223> OTHER INFORMATION: Antisense Compound

<400> SEQUENCE: 159
agtgacaacc aatcaaatgg                                               20

<210> SEQ ID NO 160
<211> LENGTH: 20
<212> TYPE: DNA
<213> ORGANISM: Artificial Sequence
<220> FEATURE:
<223> OTHER INFORMATION: Antisense Compound

<400> SEQUENCE: 160
catcttgtgg gaagtgacaa                                               20

<210> SEQ ID NO 161
<211> LENGTH: 20
<212> TYPE: DNA
<213> ORGANISM: Artificial Sequence
<220> FEATURE:
<223> OTHER INFORMATION: Antisense Compound

<400> SEQUENCE: 161
accaattggc catcatcttg                                               20

<210> SEQ ID NO 162
<211> LENGTH: 20
<212> TYPE: DNA
<213> ORGANISM: Artificial Sequence
<220> FEATURE:
<223> OTHER INFORMATION: Antisense Compound

<400> SEQUENCE: 162
ggagggcagt tttatttttg                                               20

<210> SEQ ID NO 163
<211> LENGTH: 20
<212> TYPE: DNA
<213> ORGANISM: Artificial Sequence
<220> FEATURE:
<223> OTHER INFORMATION: Antisense Compound

<400> SEQUENCE: 163
caatgtctca cccacaagcc                                               20

<210> SEQ ID NO 164
<211> LENGTH: 20
<212> TYPE: DNA
<213> ORGANISM: Artificial Sequence
<220> FEATURE:
<223> OTHER INFORMATION: Antisense Compound

<400> SEQUENCE: 164
ctaaatctag gtttctccct                                               20

<210> SEQ ID NO 165
<211> LENGTH: 20
<212> TYPE: DNA
<213> ORGANISM: Artificial Sequence
<220> FEATURE:
<223> OTHER INFORMATION: Antisense Compound

<400> SEQUENCE: 165
```
ttttgcacaa tccagaaggt                                               20

<210> SEQ ID NO 166
<211> LENGTH: 20
<212> TYPE: DNA
<213> ORGANISM: Artificial Sequence
<220> FEATURE:
<223> OTHER INFORMATION: Antisense Compound

<400> SEQUENCE: 166
gaccttaaat ataggctgct                                               20

<210> SEQ ID NO 167
<211> LENGTH: 20
<212> TYPE: DNA
<213> ORGANISM: Artificial Sequence
<220> FEATURE:
<223> OTHER INFORMATION: Antisense Compound

<400> SEQUENCE: 167
aacccaggcc ctaatcctag                                               20

<210> SEQ ID NO 168
<211> LENGTH: 20
<212> TYPE: DNA
<213> ORGANISM: Artificial Sequence
<220> FEATURE:
<223> OTHER INFORMATION: Antisense Compound

<400> SEQUENCE: 168
aggctgaaga ttaaccagcc                                               20

<210> SEQ ID NO 169
<211> LENGTH: 20
<212> TYPE: DNA
<213> ORGANISM: Artificial Sequence
<220> FEATURE:
<223> OTHER INFORMATION: Antisense Compound

<400> SEQUENCE: 169
ttggacttcc ttagcttcct                                               20

<210> SEQ ID NO 170
<211> LENGTH: 20
<212> TYPE: DNA
<213> ORGANISM: Artificial Sequence
<220> FEATURE:
<223> OTHER INFORMATION: Antisense Compound

<400> SEQUENCE: 170
gaacatagac tgggaaacag                                               20

<210> SEQ ID NO 171
<211> LENGTH: 20
<212> TYPE: DNA
<213> ORGANISM: Artificial Sequence
<220> FEATURE:
<223> OTHER INFORMATION: Antisense Compound

<400> SEQUENCE: 171
gaggctccaa cctgggtggc                                               20

<210> SEQ ID NO 172
<211> LENGTH: 20
<212> TYPE: DNA
<213> ORGANISM: Artificial Sequence

```
<220> FEATURE:
<223> OTHER INFORMATION: Antisense Compound

<400> SEQUENCE: 172
tccagcaaat gaacctgtgt                                               20

<210> SEQ ID NO 173
<211> LENGTH: 20
<212> TYPE: DNA
<213> ORGANISM: Artificial Sequence
<220> FEATURE:
<223> OTHER INFORMATION: Antisense Compound

<400> SEQUENCE: 173
cacagcggaa gtgcctgggc                                               20

<210> SEQ ID NO 174
<211> LENGTH: 20
<212> TYPE: DNA
<213> ORGANISM: Artificial Sequence
<220> FEATURE:
<223> OTHER INFORMATION: Antisense Compound

<400> SEQUENCE: 174
tgtcctagtc ctcacaccca                                               20

<210> SEQ ID NO 175
<211> LENGTH: 20
<212> TYPE: DNA
<213> ORGANISM: Artificial Sequence
<220> FEATURE:
<223> OTHER INFORMATION: Antisense Compound

<400> SEQUENCE: 175
gggacagcat cctgagcagg                                               20

<210> SEQ ID NO 176
<211> LENGTH: 20
<212> TYPE: DNA
<213> ORGANISM: H. sapiens
<220> FEATURE:

<400> SEQUENCE: 176
gggagaatgg aggagcacac                                               20

<210> SEQ ID NO 177
<211> LENGTH: 20
<212> TYPE: DNA
<213> ORGANISM: H. sapiens
<220> FEATURE:

<400> SEQUENCE: 177
ggctcggcac cagagatggg                                               20

<210> SEQ ID NO 178
<211> LENGTH: 20
<212> TYPE: DNA
<213> ORGANISM: H. sapiens
<220> FEATURE:

<400> SEQUENCE: 178
aggccctgat tgacaatcct                                               20

<210> SEQ ID NO 179
<211> LENGTH: 20
<212> TYPE: DNA
```

```
<213> ORGANISM: H. sapiens
<220> FEATURE:

<400> SEQUENCE: 179
catcctagtc attgctgcat                                              20

<210> SEQ ID NO 180
<211> LENGTH: 20
<212> TYPE: DNA
<213> ORGANISM: H. sapiens
<220> FEATURE:

<400> SEQUENCE: 180
tggtcattgg cgttggcttg                                              20

<210> SEQ ID NO 181
<211> LENGTH: 20
<212> TYPE: DNA
<213> ORGANISM: H. sapiens
<220> FEATURE:

<400> SEQUENCE: 181
atggtgtggt ggccggttgg                                              20

<210> SEQ ID NO 182
<211> LENGTH: 20
<212> TYPE: DNA
<213> ORGANISM: H. sapiens
<220> FEATURE:

<400> SEQUENCE: 182
ttgtgggcct ggcagggact                                              20

<210> SEQ ID NO 183
<211> LENGTH: 20
<212> TYPE: DNA
<213> ORGANISM: H. sapiens
<220> FEATURE:

<400> SEQUENCE: 183
agtggcttgg ctgttgctgg                                              20

<210> SEQ ID NO 184
<211> LENGTH: 20
<212> TYPE: DNA
<213> ORGANISM: H. sapiens
<220> FEATURE:

<400> SEQUENCE: 184
ctgtttgcac ccgtgtacct                                              20

<210> SEQ ID NO 185
<211> LENGTH: 20
<212> TYPE: DNA
<213> ORGANISM: H. sapiens
<220> FEATURE:

<400> SEQUENCE: 185
acctgtctgt gctctccctt                                              20

<210> SEQ ID NO 186
<211> LENGTH: 20
<212> TYPE: DNA
<213> ORGANISM: H. sapiens
<220> FEATURE:
```

```
<400> SEQUENCE: 186
ttcaccaaga tctcagtgga                                           20

<210> SEQ ID NO 187
<211> LENGTH: 20
<212> TYPE: DNA
<213> ORGANISM: H. sapiens
<220> FEATURE:

<400> SEQUENCE: 187
tccggagctg tattcatcca                                           20

<210> SEQ ID NO 188
<211> LENGTH: 20
<212> TYPE: DNA
<213> ORGANISM: H. sapiens
<220> FEATURE:

<400> SEQUENCE: 188
tgggctggaa catctatgcc                                           20

<210> SEQ ID NO 189
<211> LENGTH: 20
<212> TYPE: DNA
<213> ORGANISM: H. sapiens
<220> FEATURE:

<400> SEQUENCE: 189
tgatttacac ggtgacagga                                           20

<210> SEQ ID NO 190
<211> LENGTH: 20
<212> TYPE: DNA
<213> ORGANISM: H. sapiens
<220> FEATURE:

<400> SEQUENCE: 190
ctggccgcgc tgatgtacac                                           20

<210> SEQ ID NO 191
<211> LENGTH: 20
<212> TYPE: DNA
<213> ORGANISM: H. sapiens
<220> FEATURE:

<400> SEQUENCE: 191
acggtacaga ccttcgtcat                                           20

<210> SEQ ID NO 192
<211> LENGTH: 20
<212> TYPE: DNA
<213> ORGANISM: H. sapiens
<220> FEATURE:

<400> SEQUENCE: 192
ggcgcctgca tcctcatggg                                           20

<210> SEQ ID NO 193
<211> LENGTH: 20
<212> TYPE: DNA
<213> ORGANISM: H. sapiens
<220> FEATURE:

<400> SEQUENCE: 193
ggtattcggg tctcttcgac                                           20
```

```
<210> SEQ ID NO 194
<211> LENGTH: 20
<212> TYPE: DNA
<213> ORGANISM: H. sapiens
<220> FEATURE:

<400> SEQUENCE: 194
tctccagctt ctgctatcga                                          20

<210> SEQ ID NO 195
<211> LENGTH: 20
<212> TYPE: DNA
<213> ORGANISM: H. sapiens
<220> FEATURE:

<400> SEQUENCE: 195
ccacatcaag gcgggctgca                                          20

<210> SEQ ID NO 196
<211> LENGTH: 20
<212> TYPE: DNA
<213> ORGANISM: H. sapiens
<220> FEATURE:

<400> SEQUENCE: 196
gcgggctgca tcctgtgtgg                                          20

<210> SEQ ID NO 197
<211> LENGTH: 20
<212> TYPE: DNA
<213> ORGANISM: H. sapiens
<220> FEATURE:

<400> SEQUENCE: 197
ccatgtttct catggtcatg                                          20

<210> SEQ ID NO 198
<211> LENGTH: 20
<212> TYPE: DNA
<213> ORGANISM: H. sapiens
<220> FEATURE:

<400> SEQUENCE: 198
tcatgccagg catgatcagc                                          20

<210> SEQ ID NO 199
<211> LENGTH: 20
<212> TYPE: DNA
<213> ORGANISM: H. sapiens
<220> FEATURE:

<400> SEQUENCE: 199
tgtacccaga cgaggtggcg                                          20

<210> SEQ ID NO 200
<211> LENGTH: 20
<212> TYPE: DNA
<213> ORGANISM: H. sapiens
<220> FEATURE:

<400> SEQUENCE: 200
cgtgcgtggt gcctgaggtg                                          20

<210> SEQ ID NO 201
```

```
<211> LENGTH: 20
<212> TYPE: DNA
<213> ORGANISM: H. sapiens
<220> FEATURE:

<400> SEQUENCE: 201
caggcgcgtg tgcggcacgg                                                    20

<210> SEQ ID NO 202
<211> LENGTH: 20
<212> TYPE: DNA
<213> ORGANISM: H. sapiens
<220> FEATURE:

<400> SEQUENCE: 202
ctgctccaac atcgcctacc                                                    20

<210> SEQ ID NO 203
<211> LENGTH: 20
<212> TYPE: DNA
<213> ORGANISM: H. sapiens
<220> FEATURE:

<400> SEQUENCE: 203
cggctcgtcg tgaagctcat                                                    20

<210> SEQ ID NO 204
<211> LENGTH: 20
<212> TYPE: DNA
<213> ORGANISM: H. sapiens
<220> FEATURE:

<400> SEQUENCE: 204
tctgcgcgga ctcatgctgg                                                    20

<210> SEQ ID NO 205
<211> LENGTH: 20
<212> TYPE: DNA
<213> ORGANISM: H. sapiens
<220> FEATURE:

<400> SEQUENCE: 205
tggccgcgct catgtcctcg                                                    20

<210> SEQ ID NO 206
<211> LENGTH: 20
<212> TYPE: DNA
<213> ORGANISM: H. sapiens
<220> FEATURE:

<400> SEQUENCE: 206
cttcaacagc agcagcacgc                                                    20

<210> SEQ ID NO 207
<211> LENGTH: 20
<212> TYPE: DNA
<213> ORGANISM: H. sapiens
<220> FEATURE:

<400> SEQUENCE: 207
cttcaccatg gacatctaca                                                    20

<210> SEQ ID NO 208
<211> LENGTH: 20
<212> TYPE: DNA
<213> ORGANISM: H. sapiens
```

```
<220> FEATURE:

<400> SEQUENCE: 208
ggtgggacgg ctctgggtgg                                            20

<210> SEQ ID NO 209
<211> LENGTH: 20
<212> TYPE: DNA
<213> ORGANISM: H. sapiens
<220> FEATURE:

<400> SEQUENCE: 209
cgtggtagtg tcggtggcct                                            20

<210> SEQ ID NO 210
<211> LENGTH: 20
<212> TYPE: DNA
<213> ORGANISM: H. sapiens
<220> FEATURE:

<400> SEQUENCE: 210
cacagggcgg gcagctcttc                                            20

<210> SEQ ID NO 211
<211> LENGTH: 20
<212> TYPE: DNA
<213> ORGANISM: H. sapiens
<220> FEATURE:

<400> SEQUENCE: 211
agctcttcga ttacatccag                                            20

<210> SEQ ID NO 212
<211> LENGTH: 20
<212> TYPE: DNA
<213> ORGANISM: H. sapiens
<220> FEATURE:

<400> SEQUENCE: 212
cgtgctggcg ctcttcgtgc                                            20

<210> SEQ ID NO 213
<211> LENGTH: 20
<212> TYPE: DNA
<213> ORGANISM: H. sapiens
<220> FEATURE:

<400> SEQUENCE: 213
cgcgcgttaa tgagcagggc                                            20

<210> SEQ ID NO 214
<211> LENGTH: 20
<212> TYPE: DNA
<213> ORGANISM: H. sapiens
<220> FEATURE:

<400> SEQUENCE: 214
tggggactca tcgggggcct                                            20

<210> SEQ ID NO 215
<211> LENGTH: 20
<212> TYPE: DNA
<213> ORGANISM: H. sapiens
<220> FEATURE:

<400> SEQUENCE: 215
```
ctgctgatgg gcctggcacg                                          20

<210> SEQ ID NO 216
<211> LENGTH: 20
<212> TYPE: DNA
<213> ORGANISM: H. sapiens
<220> FEATURE:

<400> SEQUENCE: 216
cgagttctcc ttcggctcgg                                          20

<210> SEQ ID NO 217
<211> LENGTH: 20
<212> TYPE: DNA
<213> ORGANISM: H. sapiens
<220> FEATURE:

<400> SEQUENCE: 217
ctacctctac ttcgccattg                                          20

<210> SEQ ID NO 218
<211> LENGTH: 20
<212> TYPE: DNA
<213> ORGANISM: H. sapiens
<220> FEATURE:

<400> SEQUENCE: 218
tgctgttctt ctgctctggc                                          20

<210> SEQ ID NO 219
<211> LENGTH: 20
<212> TYPE: DNA
<213> ORGANISM: H. sapiens
<220> FEATURE:

<400> SEQUENCE: 219
tctccggcat agcaaggagg                                          20

<210> SEQ ID NO 220
<211> LENGTH: 20
<212> TYPE: DNA
<213> ORGANISM: H. sapiens
<220> FEATURE:

<400> SEQUENCE: 220
ctcactccct gtacagaatg                                          20

<210> SEQ ID NO 221
<211> LENGTH: 20
<212> TYPE: DNA
<213> ORGANISM: H. sapiens
<220> FEATURE:

<400> SEQUENCE: 221
ccagagagtg ccatggagat                                          20

<210> SEQ ID NO 222
<211> LENGTH: 20
<212> TYPE: DNA
<213> ORGANISM: H. sapiens
<220> FEATURE:

<400> SEQUENCE: 222
tttgtggaat gagcagaggt                                          20

```
<210> SEQ ID NO 223
<211> LENGTH: 20
<212> TYPE: DNA
<213> ORGANISM: H. sapiens
<220> FEATURE:

<400> SEQUENCE: 223
tggaggacat cagcgaggac                                                    20

<210> SEQ ID NO 224
<211> LENGTH: 20
<212> TYPE: DNA
<213> ORGANISM: H. sapiens
<220> FEATURE:

<400> SEQUENCE: 224
tgttcctctg gggcttctat                                                    20

<210> SEQ ID NO 225
<211> LENGTH: 20
<212> TYPE: DNA
<213> ORGANISM: H. sapiens
<220> FEATURE:

<400> SEQUENCE: 225
gcgttggaca ccataagcca                                                    20

<210> SEQ ID NO 226
<211> LENGTH: 20
<212> TYPE: DNA
<213> ORGANISM: H. sapiens
<220> FEATURE:

<400> SEQUENCE: 226
ctcacaggaa gtgggggtga                                                    20

<210> SEQ ID NO 227
<211> LENGTH: 20
<212> TYPE: DNA
<213> ORGANISM: H. sapiens
<220> FEATURE:

<400> SEQUENCE: 227
gaaggggcag tggggtgaga                                                    20

<210> SEQ ID NO 228
<211> LENGTH: 20
<212> TYPE: DNA
<213> ORGANISM: H. sapiens
<220> FEATURE:

<400> SEQUENCE: 228
tcccggcctt cctctgcctg                                                    20

<210> SEQ ID NO 229
<211> LENGTH: 20
<212> TYPE: DNA
<213> ORGANISM: H. sapiens
<220> FEATURE:

<400> SEQUENCE: 229
ggcagtcact tcccatgagg                                                    20

<210> SEQ ID NO 230
<211> LENGTH: 20
```

-continued

```
<212> TYPE: DNA
<213> ORGANISM: H. sapiens
<220> FEATURE:

<400> SEQUENCE: 230
gctgcagttg ccctaaggaa                                          20

<210> SEQ ID NO 231
<211> LENGTH: 20
<212> TYPE: DNA
<213> ORGANISM: M. musculus
<220> FEATURE:

<400> SEQUENCE: 231
ggggagcaga aggtcctgat                                          20

<210> SEQ ID NO 232
<211> LENGTH: 20
<212> TYPE: DNA
<213> ORGANISM: M. musculus
<220> FEATURE:

<400> SEQUENCE: 232
accaatagag gcacagttgg                                          20

<210> SEQ ID NO 233
<211> LENGTH: 20
<212> TYPE: DNA
<213> ORGANISM: M. musculus
<220> FEATURE:

<400> SEQUENCE: 233
tggtggccgg ttggagcctc                                          20

<210> SEQ ID NO 234
<211> LENGTH: 20
<212> TYPE: DNA
<213> ORGANISM: M. musculus
<220> FEATURE:

<400> SEQUENCE: 234
cagcggtcat tttgtgggcc                                          20

<210> SEQ ID NO 235
<211> LENGTH: 20
<212> TYPE: DNA
<213> ORGANISM: M. musculus
<220> FEATURE:

<400> SEQUENCE: 235
ggtgcagcaa gtggcttggc                                          20

<210> SEQ ID NO 236
<211> LENGTH: 20
<212> TYPE: DNA
<213> ORGANISM: M. musculus
<220> FEATURE:

<400> SEQUENCE: 236
tcaccatgat ttatactgtg                                          20

<210> SEQ ID NO 237
<211> LENGTH: 20
<212> TYPE: DNA
<213> ORGANISM: M. musculus
<220> FEATURE:
```

```
<400> SEQUENCE: 237
tcgtcattct tgccggggcc                                           20

<210> SEQ ID NO 238
<211> LENGTH: 20
<212> TYPE: DNA
<213> ORGANISM: M. musculus
<220> FEATURE:

<400> SEQUENCE: 238
cctatcacct gctgcgtgac                                           20

<210> SEQ ID NO 239
<211> LENGTH: 20
<212> TYPE: DNA
<213> ORGANISM: M. musculus
<220> FEATURE:

<400> SEQUENCE: 239
ctgcgtgacc ctgtgacagg                                           20

<210> SEQ ID NO 240
<211> LENGTH: 20
<212> TYPE: DNA
<213> ORGANISM: M. musculus
<220> FEATURE:

<400> SEQUENCE: 240
ctggggctta ccattgtctc                                           20

<210> SEQ ID NO 241
<211> LENGTH: 20
<212> TYPE: DNA
<213> ORGANISM: M. musculus
<220> FEATURE:

<400> SEQUENCE: 241
tacctgaggt gtgtaagcgg                                           20

<210> SEQ ID NO 242
<211> LENGTH: 20
<212> TYPE: DNA
<213> ORGANISM: M. musculus
<220> FEATURE:

<400> SEQUENCE: 242
tgtaagcggg tgtgtggcac                                           20

<210> SEQ ID NO 243
<211> LENGTH: 20
<212> TYPE: DNA
<213> ORGANISM: M. musculus
<220> FEATURE:

<400> SEQUENCE: 243
actgaggtgg gctgctctaa                                           20

<210> SEQ ID NO 244
<211> LENGTH: 20
<212> TYPE: DNA
<213> ORGANISM: M. musculus
<220> FEATURE:

<400> SEQUENCE: 244
```

```
catgctggca gtcatgctgg                                         20

<210> SEQ ID NO 245
<211> LENGTH: 20
<212> TYPE: DNA
<213> ORGANISM: M. musculus
<220> FEATURE:

<400> SEQUENCE: 245
gtgcaggtga taaggagctg                                         20

<210> SEQ ID NO 246
<211> LENGTH: 20
<212> TYPE: DNA
<213> ORGANISM: M. musculus
<220> FEATURE:

<400> SEQUENCE: 246
ctgccagtgg tgcaggcagc                                         20

<210> SEQ ID NO 247
<211> LENGTH: 20
<212> TYPE: DNA
<213> ORGANISM: M. musculus
<220> FEATURE:

<400> SEQUENCE: 247
cctgctgatg ggcctagctc                                         20

<210> SEQ ID NO 248
<211> LENGTH: 20
<212> TYPE: DNA
<213> ORGANISM: M. musculus
<220> FEATURE:

<400> SEQUENCE: 248
cagtctccgg cacagcaagg                                         20

<210> SEQ ID NO 249
<211> LENGTH: 20
<212> TYPE: DNA
<213> ORGANISM: M. musculus
<220> FEATURE:

<400> SEQUENCE: 249
cgggaggacc tggatgctga                                         20

<210> SEQ ID NO 250
<211> LENGTH: 20
<212> TYPE: DNA
<213> ORGANISM: M. musculus
<220> FEATURE:

<400> SEQUENCE: 250
ggggccagga atgtgcaatg                                         20

<210> SEQ ID NO 251
<211> LENGTH: 20
<212> TYPE: DNA
<213> ORGANISM: M. musculus
<220> FEATURE:

<400> SEQUENCE: 251
cccactaccg aggaggtggc                                         20
```

-continued

```
<210> SEQ ID NO 252
<211> LENGTH: 20
<212> TYPE: DNA
<213> ORGANISM: M. musculus
<220> FEATURE:

<400> SEQUENCE: 252
aggacatcag tgaggatccc                                            20

<210> SEQ ID NO 253
<211> LENGTH: 20
<212> TYPE: DNA
<213> ORGANISM: M. musculus
<220> FEATURE:

<400> SEQUENCE: 253
caaaaataaa actgccctcc                                            20

<210> SEQ ID NO 254
<211> LENGTH: 20
<212> TYPE: DNA
<213> ORGANISM: M. musculus
<220> FEATURE:

<400> SEQUENCE: 254
gcccaggcac ttccgctgtg                                            20

<210> SEQ ID NO 255
<211> LENGTH: 20
<212> TYPE: DNA
<213> ORGANISM: M. musculus
<220> FEATURE:

<400> SEQUENCE: 255
cctgctcagg atgctgtccc                                            20

<210> SEQ ID NO 256
<211> LENGTH: 20
<212> TYPE: DNA
<213> ORGANISM: Artificial Sequence
<220> FEATURE:
<223> OTHER INFORMATION: Antisense Compound

<400> SEQUENCE: 256
tcgatctcct tttatgcccg                                            20

<210> SEQ ID NO 257
<211> LENGTH: 24
<212> TYPE: DNA
<213> ORGANISM: Artificial Sequence
<220> FEATURE:
<223> OTHER INFORMATION: PCR Primer

<400> SEQUENCE: 257
ctcgtctcat acccgagttc ttct                                       24

<210> SEQ ID NO 258
<211> LENGTH: 27
<212> TYPE: DNA
<213> ORGANISM: Artificial Sequence
<220> FEATURE:
<223> OTHER INFORMATION: PCR Primer

<400> SEQUENCE: 258
aatgatggcg aaatagaggt agtgtac                                    27
```

```
<210> SEQ ID NO 259
<211> LENGTH: 19
<212> TYPE: DNA
<213> ORGANISM: Artificial Sequence
<220> FEATURE:
<223> OTHER INFORMATION: PCR Probe

<400> SEQUENCE: 259
tgcgaccctc agcgtgccc                                                       19

<210> SEQ ID NO 260
<211> LENGTH: 15
<212> TYPE: DNA
<213> ORGANISM: Artificial Sequence
<220> FEATURE:
<223> OTHER INFORMATION: PCR Primer

<400> SEQUENCE: 260
tcgccgcttg ctgca                                                           15

<210> SEQ ID NO 261
<211> LENGTH: 17
<212> TYPE: DNA
<213> ORGANISM: Artificial Sequence
<220> FEATURE:
<223> OTHER INFORMATION: PCR Primer

<400> SEQUENCE: 261
atcggccgtg atgtcga                                                         17

<210> SEQ ID NO 262
<211> LENGTH: 23
<212> TYPE: DNA
<213> ORGANISM: Artificial Sequence
<220> FEATURE:
<223> OTHER INFORMATION: PCR Probe

<400> SEQUENCE: 262
ccatggtcaa ccccaccgtg ttc                                                  23

<210> SEQ ID NO 263
<211> LENGTH: 25
<212> TYPE: DNA
<213> ORGANISM: Artificial Sequence
<220> FEATURE:
<223> OTHER INFORMATION: PCR Primer

<400> SEQUENCE: 263
atggagcaac acgtagaggc aggct                                                25

<210> SEQ ID NO 264
<211> LENGTH: 25
<212> TYPE: DNA
<213> ORGANISM: Artificial Sequence
<220> FEATURE:
<223> OTHER INFORMATION: PCR Primer

<400> SEQUENCE: 264
gagtgccgcc agccctcctg tcaca                                                25

<210> SEQ ID NO 265
<211> LENGTH: 20
<212> TYPE: DNA
<213> ORGANISM: Artificial Sequence
<220> FEATURE:
<223> OTHER INFORMATION: Antisense Compound

<400> SEQUENCE: 265
```
gagaacatat ccaccgagat                                                  20

<210> SEQ ID NO 266
<211> LENGTH: 20
<212> TYPE: DNA
<213> ORGANISM: Artificial Sequence
<220> FEATURE:
<223> OTHER INFORMATION: Antisense Compound

<400> SEQUENCE: 266
ctgcacagtg tctgtgtaca                                                  20

<210> SEQ ID NO 267
<211> LENGTH: 20
<212> TYPE: DNA
<213> ORGANISM: Artificial Sequence
<220> FEATURE:
<223> OTHER INFORMATION: Antisense Compound

<400> SEQUENCE: 267
ccttccctga aggttcctcc                                                  20

<210> SEQ ID NO 268
<211> LENGTH: 19
<212> TYPE: DNA
<213> ORGANISM: Artificial Sequence
<220> FEATURE:
<223> OTHER INFORMATION: Antisense Compound

<400> SEQUENCE: 268
cgagaggcgg acgggaccg                                                   19

<210> SEQ ID NO 269
<211> LENGTH: 21
<212> TYPE: DNA
<213> ORGANISM: Artificial Sequence
<220> FEATURE:
<223> OTHER INFORMATION: Antisense Compound

<400> SEQUENCE: 269
cgagaggcgg acgggaccgt t                                                21

<210> SEQ ID NO 270
<211> LENGTH: 21
<212> TYPE: DNA
<213> ORGANISM: Artificial Sequence
<220> FEATURE:
<223> OTHER INFORMATION: Complement of Antisense Compound

<400> SEQUENCE: 270
cggtcccgtc cgcctctcgt t                                                21

<210> SEQ ID NO 271
<211> LENGTH: 19
<212> TYPE: DNA
<213> ORGANISM: Artificial Sequence
<220> FEATURE:
<223> OTHER INFORMATION: Antisense Compound

<400> SEQUENCE: 271
cggtcccgtc cgcctctcg                                                   19

<210> SEQ ID NO 272
<211> LENGTH: 19
<212> TYPE: DNA
<213> ORGANISM: Artificial Sequence

```
<220> FEATURE:
<223> OTHER INFORMATION: Antisense compound

<400> SEQUENCE: 272
gaagtagcca ccaactgtg                                              19

<210> SEQ ID NO 273
<211> LENGTH: 18
<212> TYPE: DNA
<213> ORGANISM: Artificial Sequence
<220> FEATURE:
<223> OTHER INFORMATION: Antisense compound

<400> SEQUENCE: 273
gaagtagcca ccaactgt                                               18

<210> SEQ ID NO 274
<211> LENGTH: 17
<212> TYPE: DNA
<213> ORGANISM: Artificial Sequence
<220> FEATURE:
<223> OTHER INFORMATION: Antisense compound

<400> SEQUENCE: 274
gaagtagcca ccaactg                                                17

<210> SEQ ID NO 275
<211> LENGTH: 16
<212> TYPE: DNA
<213> ORGANISM: Artificial Sequence
<220> FEATURE:
<223> OTHER INFORMATION: Antisense compound

<400> SEQUENCE: 275
gaagtagcca ccaact                                                 16
```